United States Patent
Borloz et al.

(10) Patent No.: US 12,313,211 B2
(45) Date of Patent: *May 27, 2025

(54) JOINT ROTATION STOP STRUCTURES FOR ARTICULATED SUPPORT ARMS

(71) Applicant: GCX Corporation, Petaluma, CA (US)

(72) Inventors: Paul Rene Borloz, Petaluma, CA (US); Joshua Kawarii Littlefield, Santa Rosa, CA (US); Robert Peter Glaser, Corte Madera, CA (US)

(73) Assignee: GCX Corporation, Petaluna, CA (US)

( * ) Notice: Subject to any disclaimer, the term of this patent is extended or adjusted under 35 U.S.C. 154(b) by 14 days.

This patent is subject to a terminal disclaimer.

(21) Appl. No.: 18/052,068

(22) Filed: Nov. 2, 2022

(65) Prior Publication Data

US 2024/0125426 A1 Apr. 18, 2024

Related U.S. Application Data

(63) Continuation of application No. 16/803,905, filed on Feb. 27, 2020, now Pat. No. 11,530,774.

(Continued)

(51) Int. Cl.
*F16M 13/02* (2006.01)
*E04B 9/00* (2006.01)
(Continued)

(52) U.S. Cl.
CPC ........... *F16M 11/08* (2013.01); *F16M 11/105* (2013.01); *F16M 11/2035* (2013.01);
(Continued)

(58) Field of Classification Search
CPC .... F16M 11/20; F16M 11/2035; F16M 11/05; F16M 11/10; F16M 11/105; F16M 11/24;
(Continued)

(56) References Cited

U.S. PATENT DOCUMENTS

| 4,304,385 A | 12/1981 | Farouche et al. |
| 4,880,193 A | 11/1989 | Warshawsky |

(Continued)

FOREIGN PATENT DOCUMENTS

| CN | 20605517 U | 3/2017 | |
| DE | 202006012145 U1 * | 12/2006 | ............. F16M 11/04 |
| EP | 2813731 B1 | 5/2018 | |

OTHER PUBLICATIONS

European Search Report mailed Feb. 15, 2021 for EP Application No. 20202716.5-1009, 9 pages.

(Continued)

*Primary Examiner* — Eret C McNichols
(74) *Attorney, Agent, or Firm* — Perkins Coie LLP

(57) ABSTRACT

Improved support structures and systems are disclosed for installing tablet devices, display screens, flat screen monitors, or medical devices within a wide variety of environments. A core arm extends from a rear end, toward a front end, in which the rear end is configured to be pivotably mounted either directly to a mount structure, or to an extension arm that in turn is mounted to a mount structure. The front end is configured to be pivotably mounted to a front-end panel mount structure. The structures and systems can be configured for light or heavy configurations, with or without the use of an extension arm, and can provide fully concealed cable routing, in which one or more cables are readily accessible, via snap fit covers, for easy installation and maintenance, which can provide a clean structure that can readily be serviced and cleaned as desired.

20 Claims, 70 Drawing Sheets

Related U.S. Application Data

(60) Provisional application No. 62/812,893, filed on Mar. 1, 2019.

(51) Int. Cl.
*F16M 11/08* (2006.01)
*F16M 11/10* (2006.01)
*F16M 11/20* (2006.01)
*F16M 11/24* (2006.01)
*F21V 21/00* (2006.01)
*A61B 90/50* (2016.01)

(52) U.S. Cl.
CPC ............ *F16M 11/24* (2013.01); *F16M 13/02* (2013.01); *A61B 90/50* (2016.02); *E04B 9/00* (2013.01); *F16M 11/10* (2013.01); *F16M 11/20* (2013.01); *F16M 2200/06* (2013.01); *F21V 21/00* (2013.01)

(58) Field of Classification Search
CPC .. F16M 13/02; F16M 2200/06; F16M 11/046; F16M 11/2021; F16M 11/08; F16M 11/2014; F16M 11/2064; F16M 2200/063; F16M 2200/068
See application file for complete search history.

(56) References Cited

U.S. PATENT DOCUMENTS

| | | | |
|---|---|---|---|
| 5,123,621 A | 6/1992 | Gates | |
| 5,743,503 A | 4/1998 | Voeller et al. | |
| 5,975,472 A | 11/1999 | Hung | |
| 6,409,134 B1 | 6/2002 | Oddsen | |
| 6,478,274 B1 | 11/2002 | Oddsen | |
| 6,478,275 B1 | 11/2002 | Huang | |
| 6,609,691 B2 | 8/2003 | Oddsen | |
| 7,207,537 B2* | 4/2007 | Hung | F16M 13/02 248/920 |
| 7,264,212 B2* | 9/2007 | Hung | F16M 11/10 D14/452 |
| 7,395,995 B2 | 7/2008 | Chen | |
| 7,997,211 B2 | 8/2011 | Peterson et al. | |
| 8,469,323 B1 | 6/2013 | Deros et al. | |
| 8,794,579 B2 | 8/2014 | Sturman et al. | |
| 8,960,632 B2 | 2/2015 | Fallows | |
| 9,228,696 B2 | 1/2016 | Borloz et al. | |
| 9,239,127 B2* | 1/2016 | Krönung | F16M 11/06 |
| 9,277,812 B2 | 3/2016 | Bennett et al. | |
| 9,746,125 B2 | 8/2017 | Bowman et al. | |
| 9,945,498 B2* | 4/2018 | Timoszyk | A61B 90/30 |
| 10,274,131 B2 | 4/2019 | Petts et al. | |
| 10,851,938 B2 | 12/2020 | Glickstein | |
| 10,948,946 B2 | 3/2021 | Borloz et al. | |
| 11,530,774 B2* | 12/2022 | Borloz | F16M 11/105 |
| 11,662,055 B2* | 5/2023 | Vlaar | F16M 11/24 248/125.7 |
| 2001/0023914 A1 | 9/2001 | Oddsen | |
| 2002/0190180 A1 | 12/2002 | Cotterill | |
| 2003/0161159 A1* | 8/2003 | Kupfer | F16M 11/2064 362/402 |
| 2005/0230585 A1 | 10/2005 | Hung | |
| 2007/0089648 A1 | 4/2007 | Harrison et al. | |
| 2007/0295878 A1* | 12/2007 | Smed | F16M 11/2014 248/413 |
| 2010/0327129 A1 | 12/2010 | Chen | |
| 2011/0147546 A1 | 6/2011 | Monsalve et al. | |
| 2011/0260017 A1* | 10/2011 | Monsalve | F16M 13/022 248/201 |
| 2012/0235000 A1 | 9/2012 | Borloz et al. | |
| 2013/0112828 A1* | 5/2013 | Sapper | F16M 11/2092 248/274.1 |
| 2014/0367137 A1 | 12/2014 | Leung | |
| 2015/0308611 A1 | 10/2015 | Oginski et al. | |
| 2015/0366627 A1* | 12/2015 | Oginski | F16M 13/027 403/112 |
| 2016/0091117 A1 | 3/2016 | Boccoleri et al. | |
| 2017/0314731 A1 | 11/2017 | Glaser et al. | |
| 2018/0340644 A1 | 11/2018 | Bowman et al. | |
| 2018/0356031 A1 | 12/2018 | Zebarjad et al. | |
| 2018/0372268 A1 | 12/2018 | Hung | |
| 2019/0086022 A1 | 3/2019 | Anderson et al. | |
| 2020/0278074 A1 | 9/2020 | Borloz et al. | |

OTHER PUBLICATIONS

European Communication dated Dec. 23, 2024 for EP Application No. 20765800.6-1009, 8 pages.

* cited by examiner

10 ⬈

20 ⬈

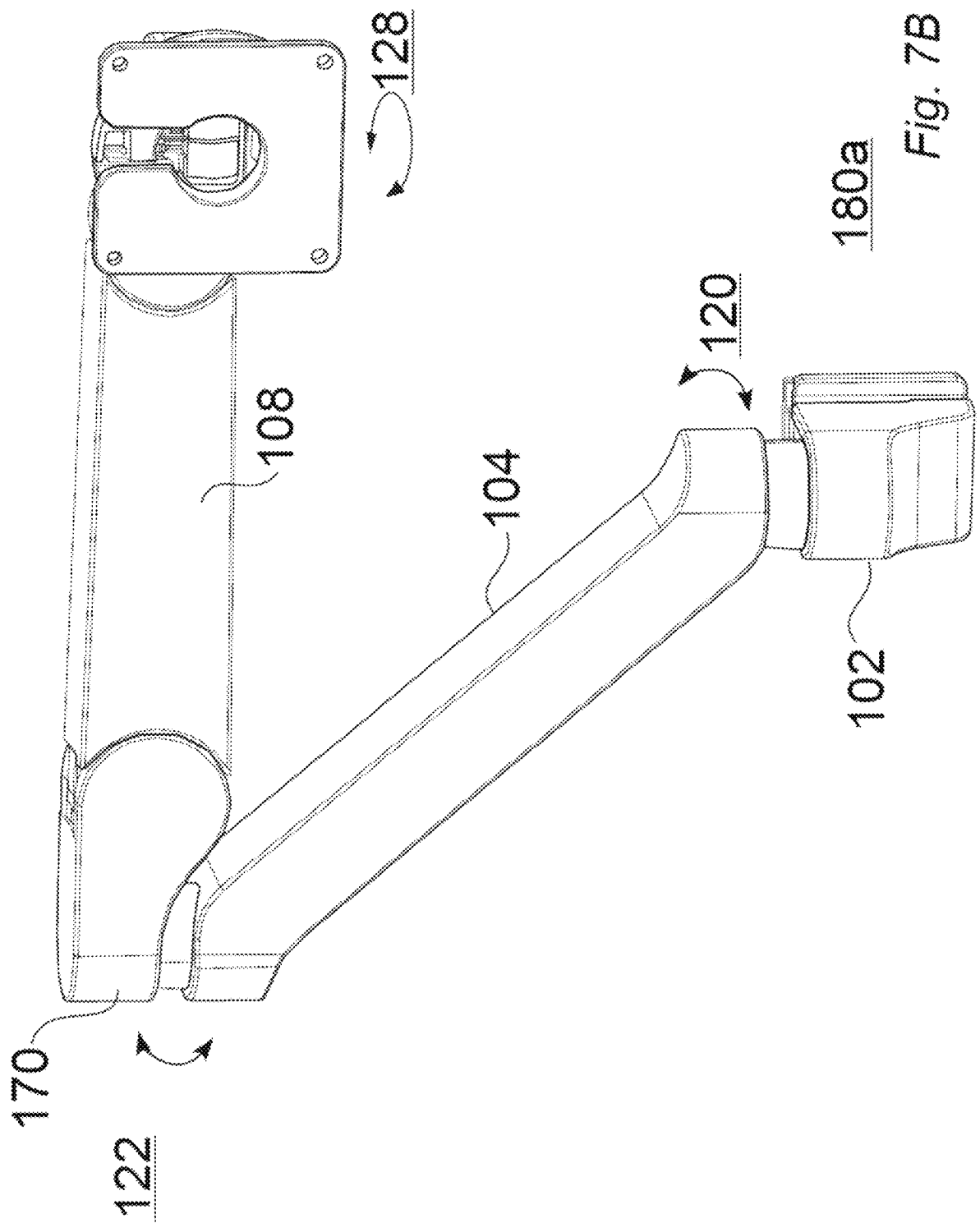

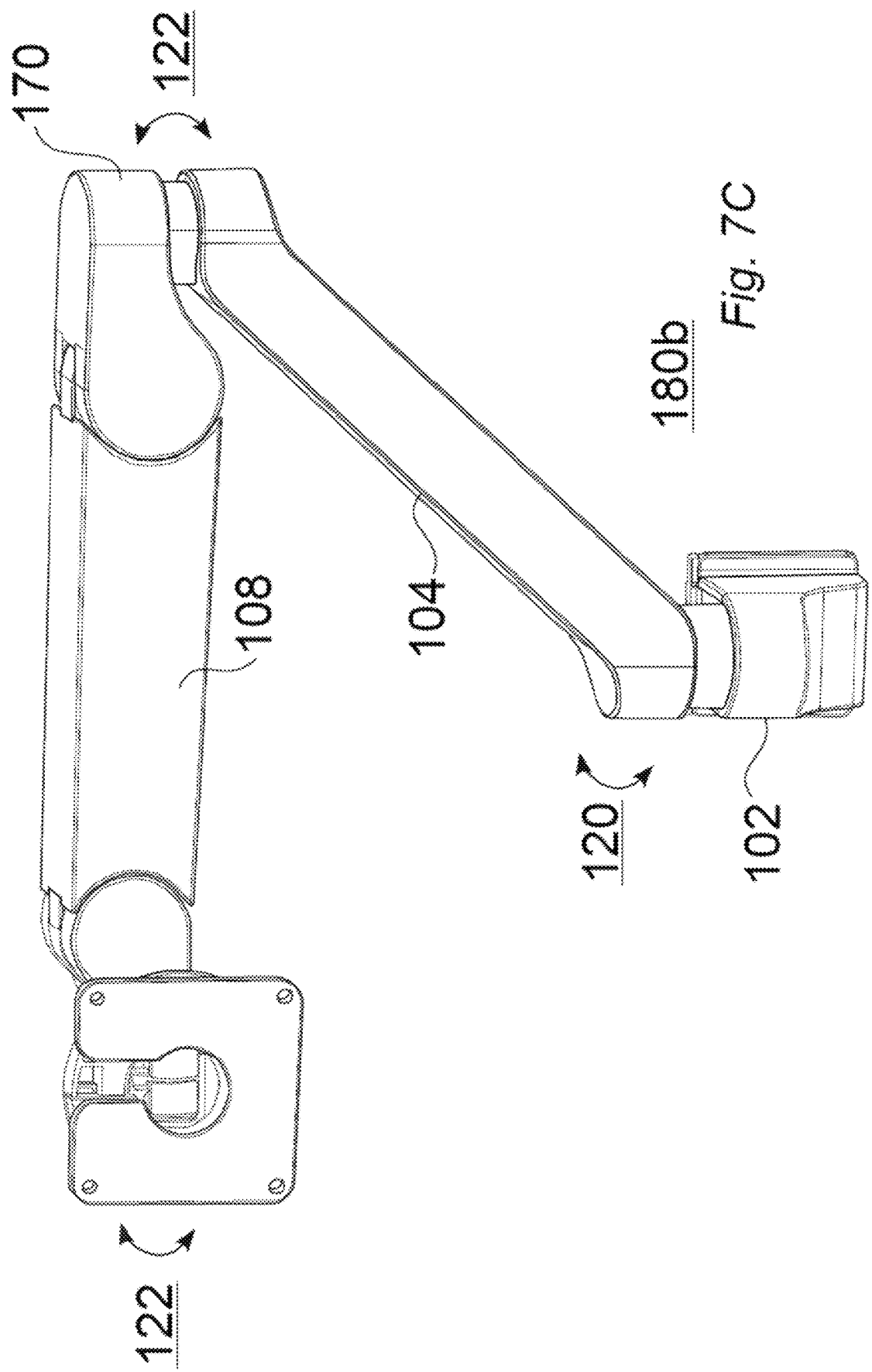

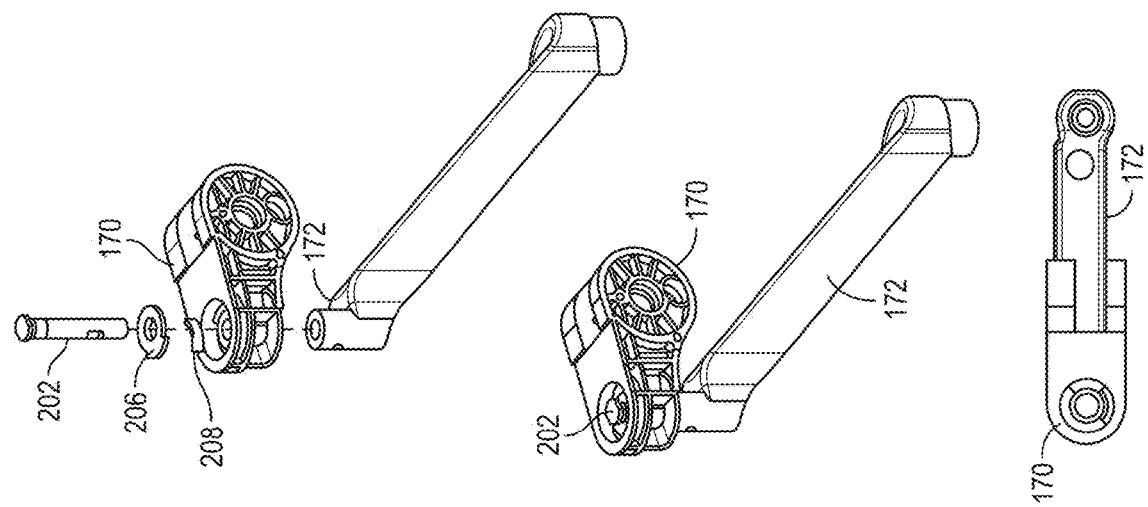
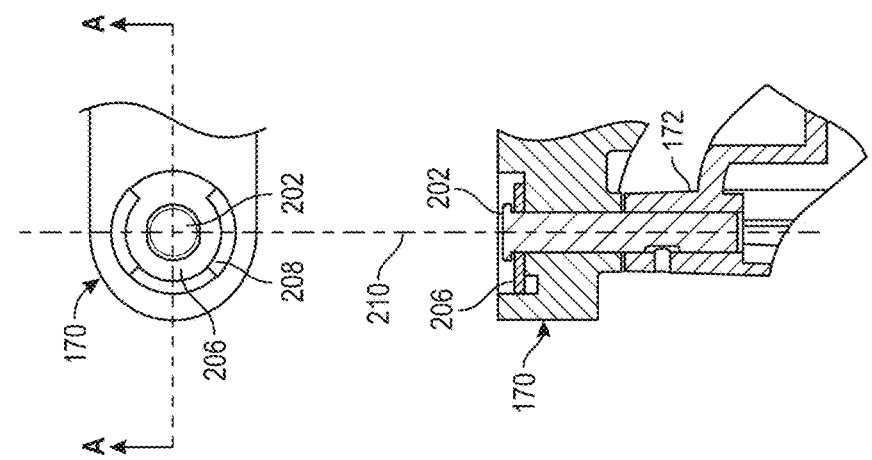
FIG. 7E

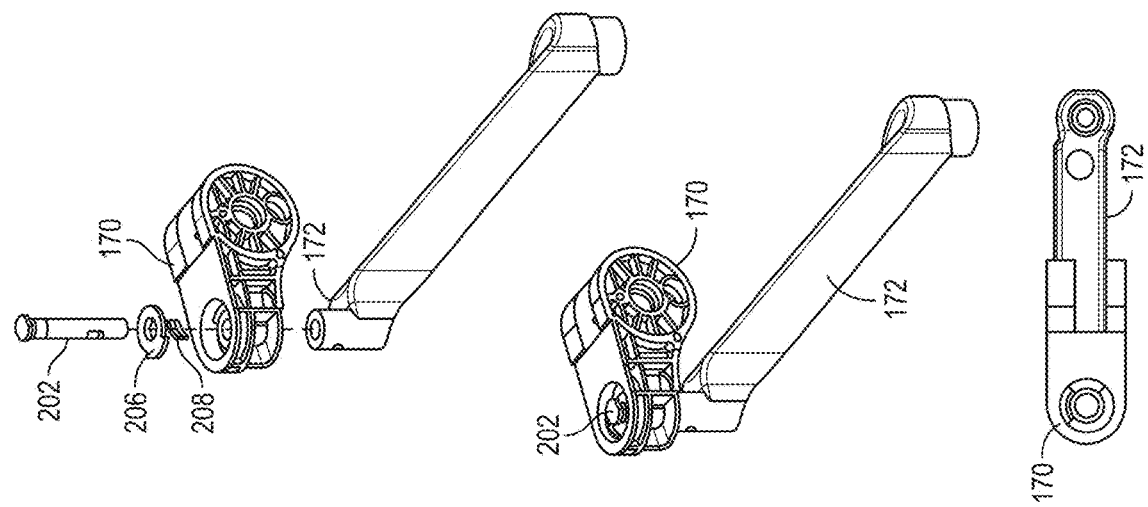
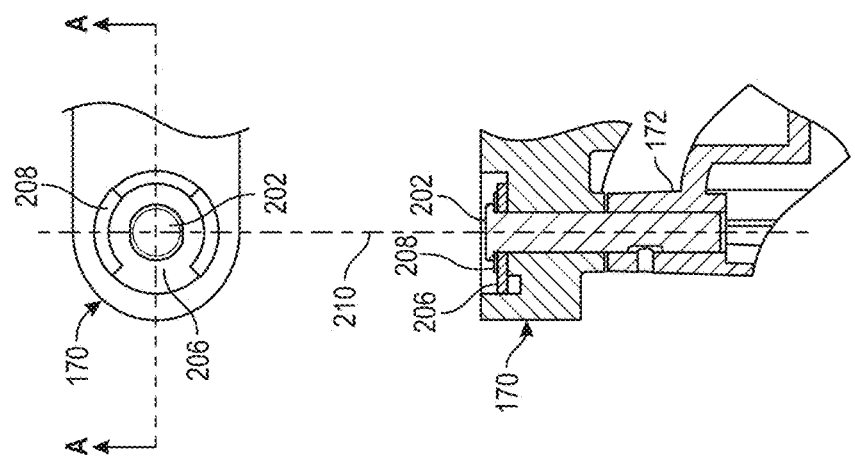
FIG. 7G

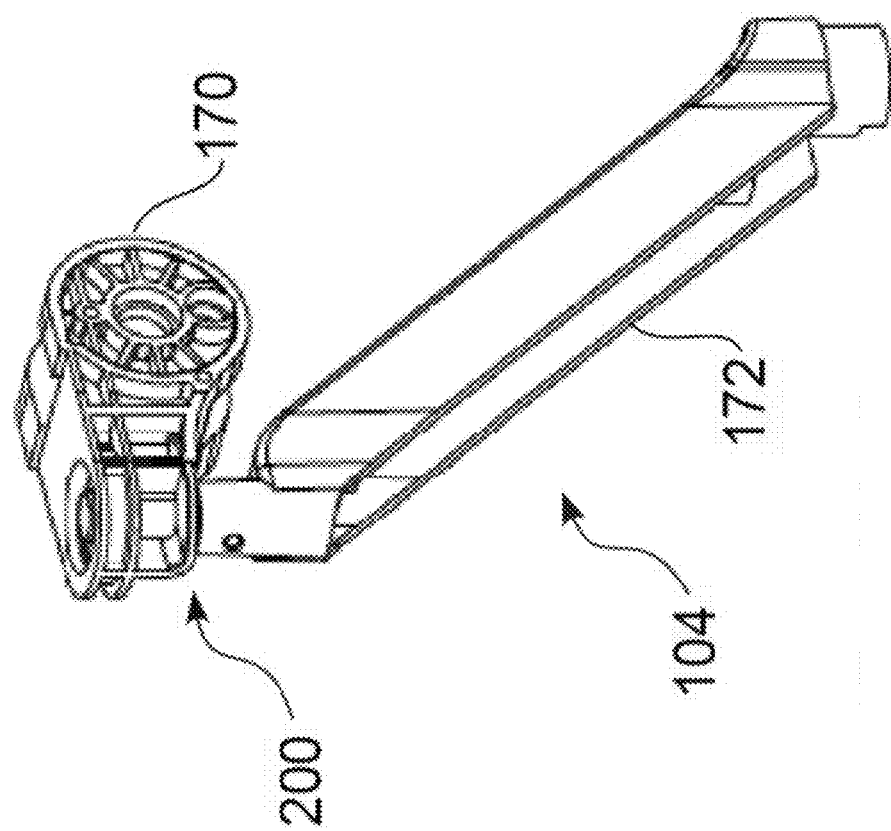
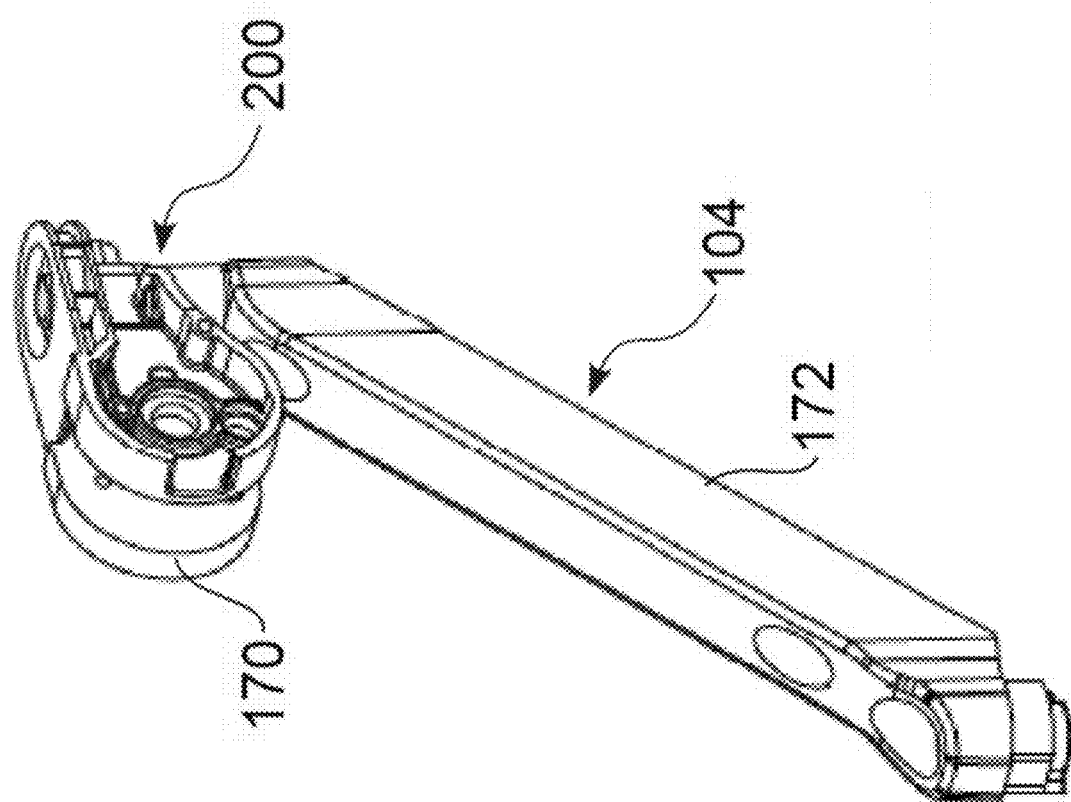
Fig. 7H

2200

2900

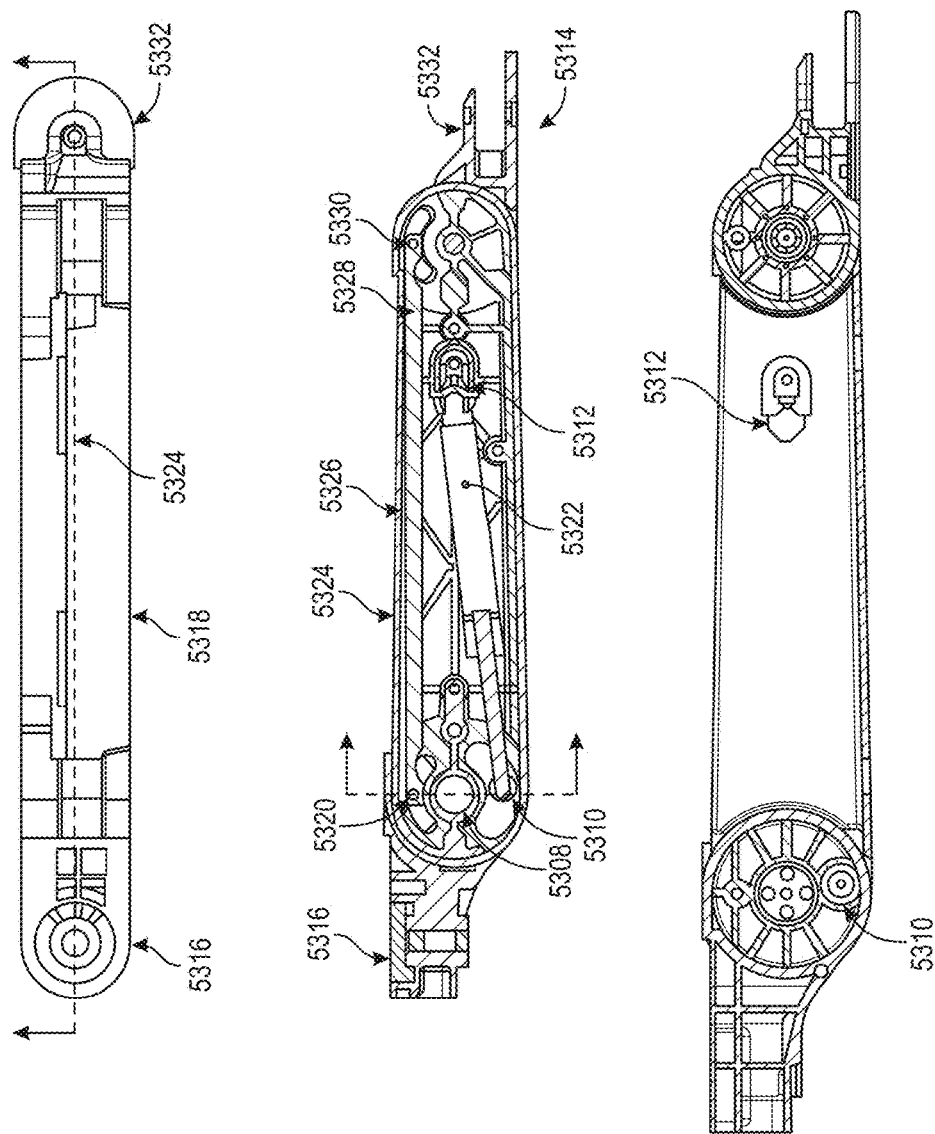
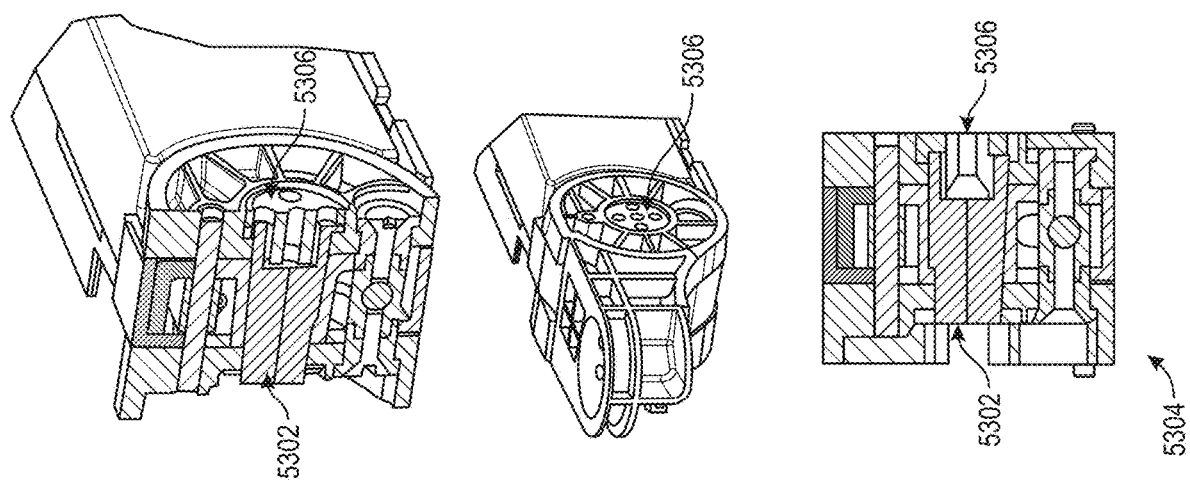
FIG. 53

JOINT ROTATION STOP STRUCTURES FOR ARTICULATED SUPPORT ARMS

CROSS-REFERENCE TO RELATED APPLICATIONS

This application is a continuation of U.S. patent application Ser. No. 16/803,905, titled "Joint Rotation Stop Structures for Articulated Support Arms" and filed Feb. 27, 2020, which claims the benefit of U.S. provisional patent application No. 62/812,893, titled "Joint Rotation Stop Structures for Articulated Support Arms, and Associated Methods" and filed Mar. 1, 2019, is the disclosures of which are incorporated herein by reference in their entireties.

FIELD OF THE INVENTION

At least one embodiment of the present invention pertains to tablet support structures, systems and methods of assembly, operation, and service.

BACKGROUND

Display screens are utilized to display information in various contexts. For example, a computer screen in a hospital can display medical data to an individual. In many environments, the screen may need to be positioned and moved between various positions as needed. This may be implemented using a support that can support the weight of the screen and allow for the screen to be moved between various positions and/or heights.

While many mounting arm structures can support screens, such as display screens and computer screens, it is often difficult to support different loads and position the screen at different heights. Further, in many cases, it can be difficult to rotate or pivot the supported screen at a desired position.

Furthermore, such screens are often used within work environments, such as within hospitals or other medical or dental facilities. In such environments, cleanliness is a priority, and a sterile work environment may be required. In many cases, support structures may be unable to engage with various cabling associated with the screen so as to maintain a sterile environment.

BRIEF DESCRIPTION OF THE DRAWINGS

Various features and characteristics of the technology will become more apparent to those skilled in the art from a study of the Detailed Description in conjunction with the drawings. Embodiments of the technology are illustrated by way of example and not limitation in the drawings, in which like references may indicate similar elements.

FIG. 7B is a perspective view of a tablet arm including a core support arm 108 pivotably connected to an extension arm in a first rotated position, in accordance with various embodiments.

FIG. 7C is an illustrative view of a tablet arm including a core support arm pivotably connected to an extension arm, in a second rotated position, in accordance with various embodiments.

FIG. 7E provides detailed views of an illustrative joint rotation stop structure that includes a pivot stop structure, in accordance with various embodiments.

FIG. 7G provides detailed views of an illustrative joint rotation stop structure 200 that includes a pivot stop structure, in accordance with various embodiments.

FIG. 7H provides assembly views of an illustrative tablet arm that includes an extension structure, and a joint rotation stop structure that includes a pivot stop structure, in accordance with various embodiments.

FIG. 53 shows core support arm details related to counterbalance and friction, in accordance with various embodiments.

Figure 1A:
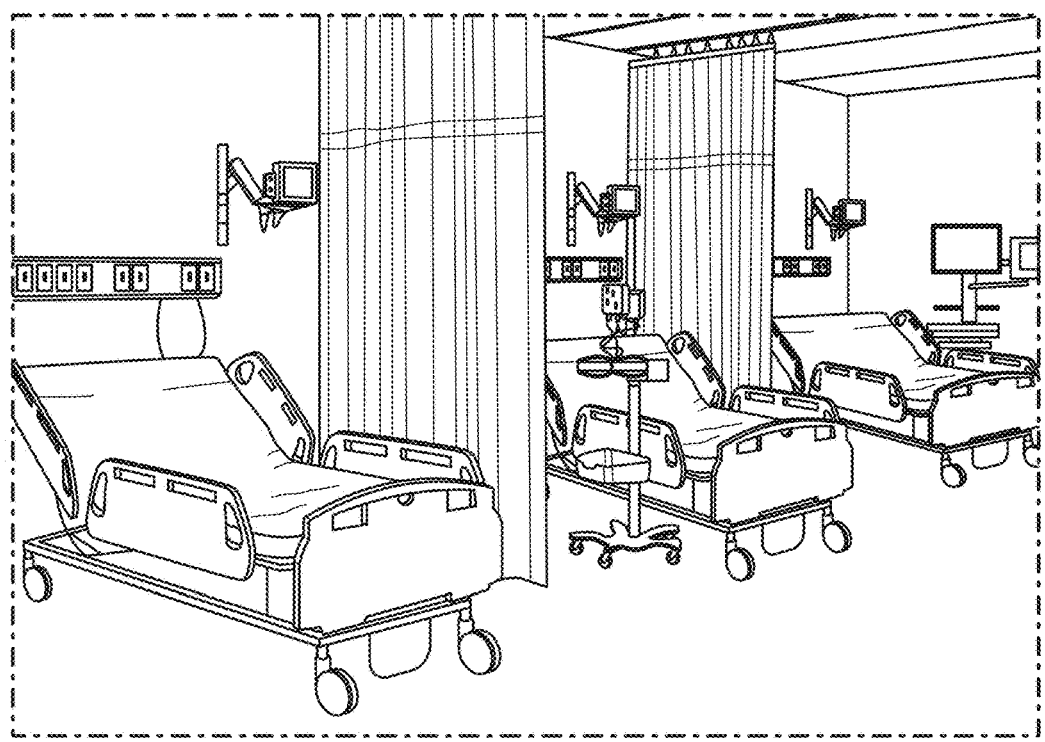
FIGS. 1A and 1B show illustrative environments in which a tablet arm apparatus and system as described herein can be utilized, in accordance with various embodiments.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

The present embodiments relate to devices, structures, systems and associated methods for supporting a tablet display within an environment, such as within a hospital or other medical, dental or testing facility. The mounting structures and systems can be mounted in a variety of manners, such as a fixed mounting to a wall, a mounting through an intermediate channel, and/or mounting to a stationary or moveable equipment or structures.

In one exemplary aspect, a support arm can include a core arm body extending from a first end to a second end opposing the first end. The first end can be pivotably mounted directly to a mount structure or mounted to an extension arm that is mounted to the mount structure. The second end can be pivotably mounted to a front-end panel mount structure. The support arm can include a rear axle disposed on the first end. The support arm can also include a front axle disposed on the second end. The support arm can also include a linkage assembly that includes a spring element extending from the first end to the second end.

In some embodiments, the front-end panel mount structure is configured to engage with a display device, and wherein the front-end panel mount structure is configured to rotate about a vertical axis.

In some embodiments, the spring element provides a gas spring counterbalance force.

In some embodiments, the gas spring counterbalance force is non-adjustable, and wherein the gas spring counterbalance is configured to be set for any counterbalance value that is within a payload range.

In some embodiments, the method can include a friction pack element disposed within the second end of the core arm body, the friction pack element providing both a level of upward resistance and a level of downward resistance.

In some embodiments, the friction pack element is non-adjustable, and wherein the friction pack element supports any payload that is within a range of payloads.

In some embodiments, the extension arm mounts to the mount structure at the first end and extends to a rear mount configured to engage to an environmental support structure.

In some embodiments, the extension arm is disposed subjacent to the core arm body, wherein the mount structure facilitates rotation of the core arm body about a vertical axis, and wherein the rear mount facilitates rotation of the extension arm about the vertical axis.

In some embodiments, the core arm body forms an opening interior of the core arm body, the opening configured to receive cabling for a display device, wherein the cabling is configured to exposed at the front-end panel mount structure.

In some embodiments, a rotation range of the front-end panel mount structure relative to a vertical axis prevents binding of the cabling for the display device disposed in the core arm body through the front-end panel mount structure.

In some embodiments, the mount structure engaged to the first end includes a joint rotation stop structure configured to limit rotation of the mount structure to a defined rotation range relative to a vertical axis.

In some embodiments, the joint rotation stop structure can include any of a pivot stop floating key configured to facilitate rotating of the joint rotation stop structure about a pivot stop rotation range relative to the vertical axis, a pivot stop disc disposed interior of the pivot stop floating key, wherein the pivot stop disc includes a protruded surface that, when engaged with the pivot stop floating key at a position at an end of the pivot stop rotation range, prevents rotation of the pivot stop floating key, and a pivot post disposed interior to the pivot stop disc and engaged to both the pivot stop floating key and the pivot stop disc.

In another exemplary embodiment, an apparatus to provide support and rotational movement to a display device can include a support arm extending from a rear end to a front end opposing the rear end.

The support arm can include a mount structure disposed at the rear end. The support arm can include a front-end panel mount structure disposed at the front end configured to engage with the display device and rotate about a vertical axis. The support arm can include a rear axle disposed on the rear end. The support arm can include a front axle disposed on the front end. The support arm can include a linkage assembly that includes a spring element extending from the rear end to the front end.

The apparatus can also include an extension arm engaged to the support arm at the mount structure. The extension arm can include a rear mount configured to engage to an environmental support structure and rotate the extension arm about the vertical axis.

In some embodiments, the spring element provides a gas spring counterbalance force that is non-adjustable and configured to be set for any counterbalance value that is within a payload range.

In some embodiments, the method includes a friction pack element disposed within the front end of the core arm, wherein the friction pack element provides both a level of upward resistance and a level of downward resistance.

In some embodiments, the core arm forms an opening interior of the core arm, the opening configured to receive cabling for a display device, wherein the cabling is configured to exposed at the front-end panel mount structure.

In some embodiments, the mount structure engaged to the first end includes a joint rotation stop structure configured to limit rotation of the mount structure to a defined rotation range relative to the vertical axis. The joint rotation stop structure can include any of a pivot stop floating key configured to facilitate rotating of the joint rotation stop structure about a pivot stop rotation range relative to the vertical axis, a pivot stop disc disposed interior of the pivot stop floating key, wherein the pivot stop disc includes a protruded surface that, when engaged with the pivot stop floating key at a position at an end of the pivot stop rotation range, prevents rotation of the pivot stop floating key, and a pivot post disposed interior to the pivot stop disc and engaged to both the pivot stop floating key and the pivot stop disc.

References in this description to "an embodiment", "one embodiment", or the like, mean that the particular feature, function, structure or characteristic being described is included in at least one embodiment of the present invention. Occurrences of such phrases in this specification do not necessarily all refer to the same embodiment. On the other hand, the embodiments referred to also are not necessarily mutually exclusive.

Figure 1B:
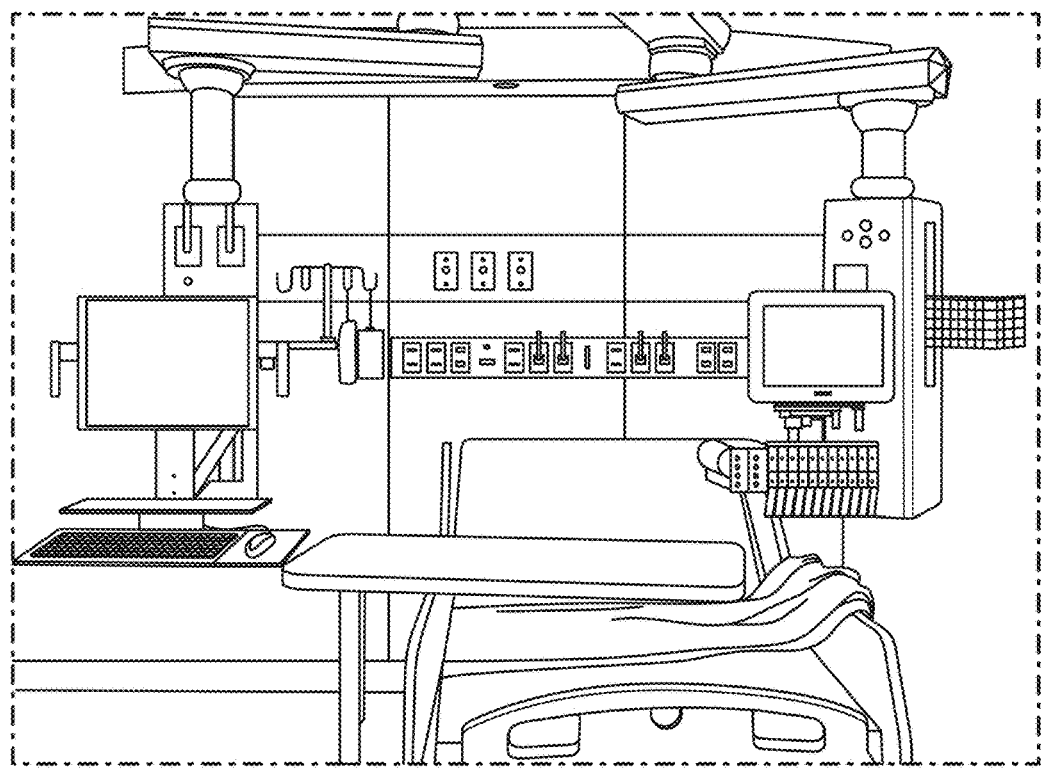
Figure 2:
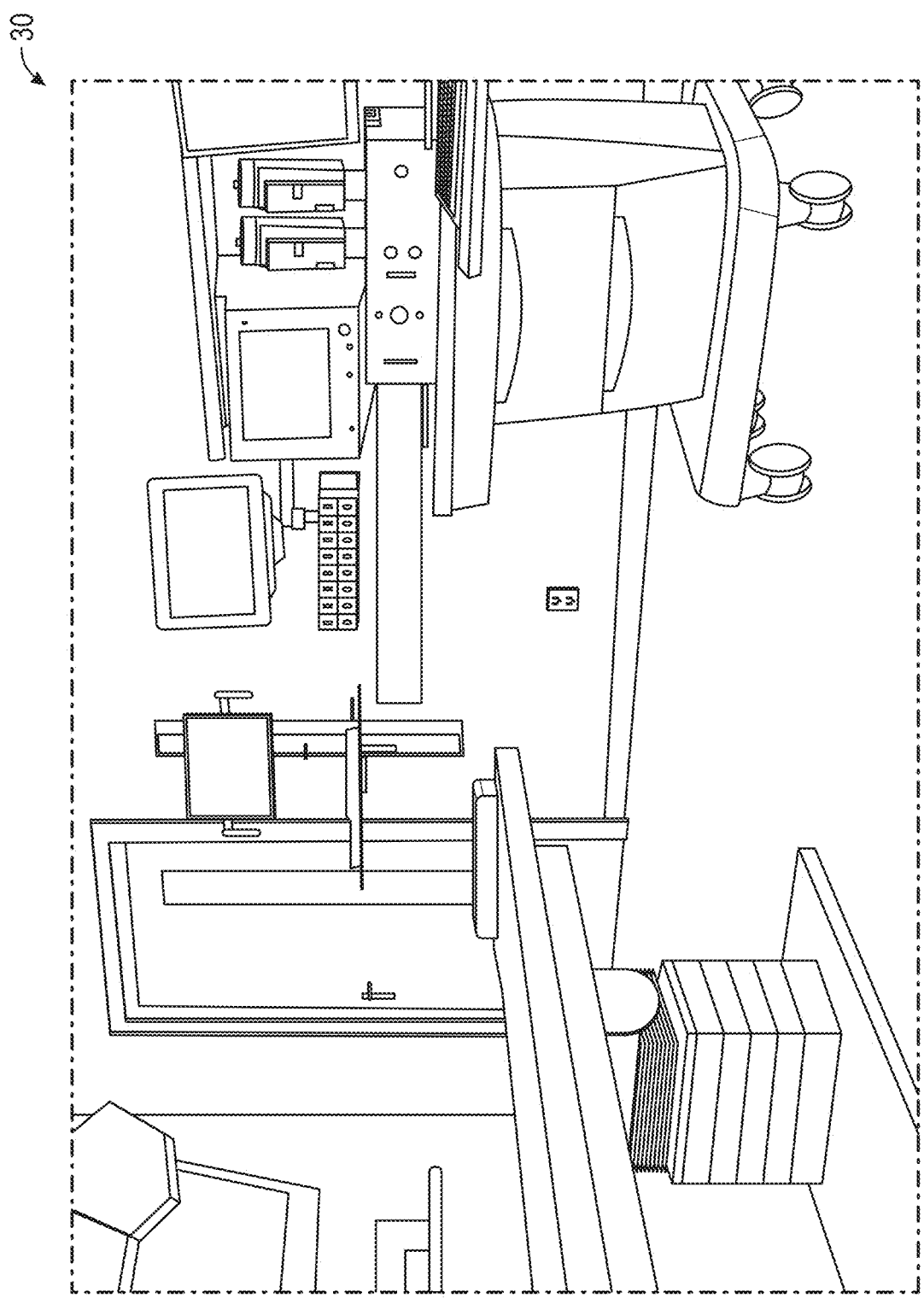
FIG. 2 shows an illustrative work environment, in accordance with various embodiments.

FIGS. 1A and 1B show illustrative environments (e.g., environment 10, environment 20) in which a tablet arm apparatus and system as described herein can be utilized, in accordance with various embodiments. FIG. 2 shows an illustrative work environment 30, in accordance with various embodiments. The work environment 30 can include a medical facility, for example. A tablet arm apparatus as described herein can be affixed in the environment in any of a variety of ways, such as direct mounting to a wall, mounting to a modular wall structure, or mounting to stationary or movable structures, for example.

As shown in FIGS. 1A, 1B, and/or 2, a work environment can include an environment in which one or more individuals perform various tasks across various positions in the environment. For instance, as shown in FIG. 1A, the environment 10 can include a series of hospital bed stations, and an individual (e.g., doctor, nurse) can move between hospital bed stations to perform various tasks (e.g., interact with patients, perform tests). As the individual moves between various stations and/or performs different tasks, the position/height of display screens may be moved to a desired position that can be unique to each individual.

Figure 3:
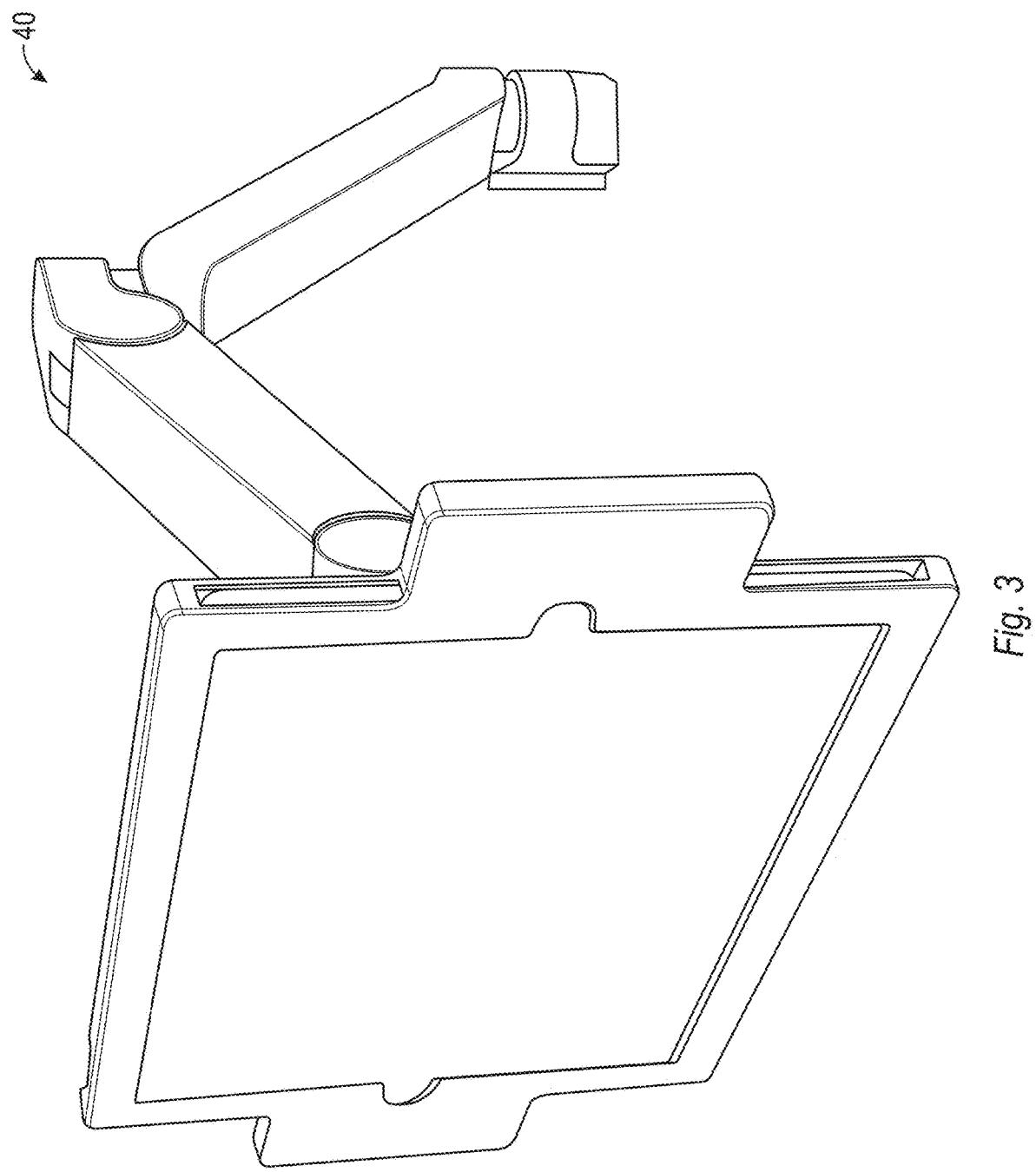
FIG. 3 is a front view of a tablet or screen mounted to an illustrative tablet arm 42, in accordance with various embodiments.

FIG. 3 is a front view of a tablet or screen 40 mounted to an illustrative tablet arm, in accordance with various embodiments. As seen in FIG. 3, the tablet arm can include an intermediate mounting frame that can be configured to contain and surround a tablet display device 40 while providing a secure connection to the mounting arm. In some embodiments, the tablet arm can be configured with a combination of friction and spring forces, such that the tablet arm does not require a counterbalance adjustment.

Figure 4:
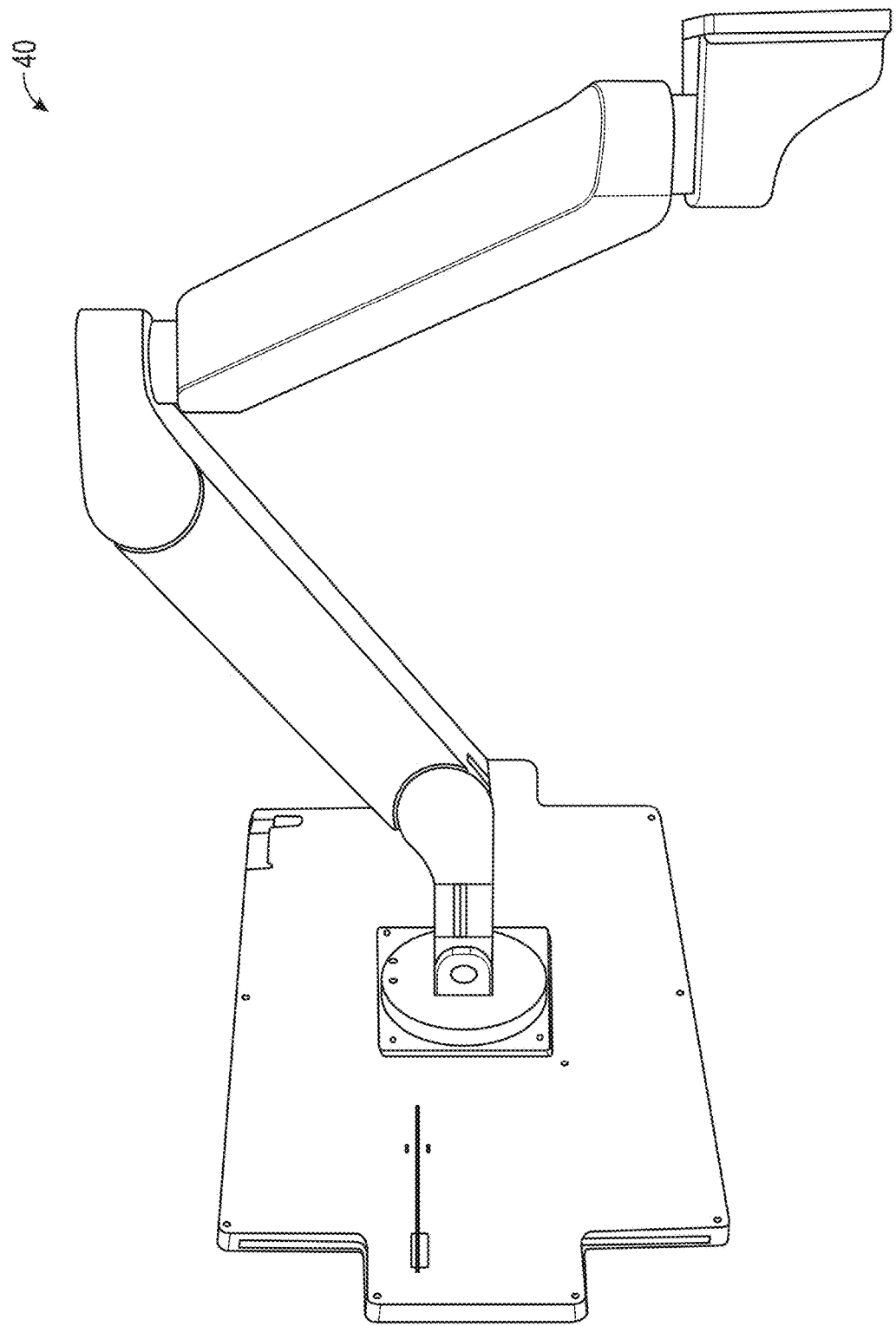
FIG. 4 is a rear view of a tablet or screen mounted to an illustrative tablet arm 4, in accordance with various embodiments.

FIG. 4 is a rear view of a tablet or screen 40 mounted to an illustrative tablet arm, in accordance with various embodiments. As shown in FIG. 4, the tablet arm can include an extension arm, which is discussed in greater detail with respect to FIG. 5.

Figure 5:
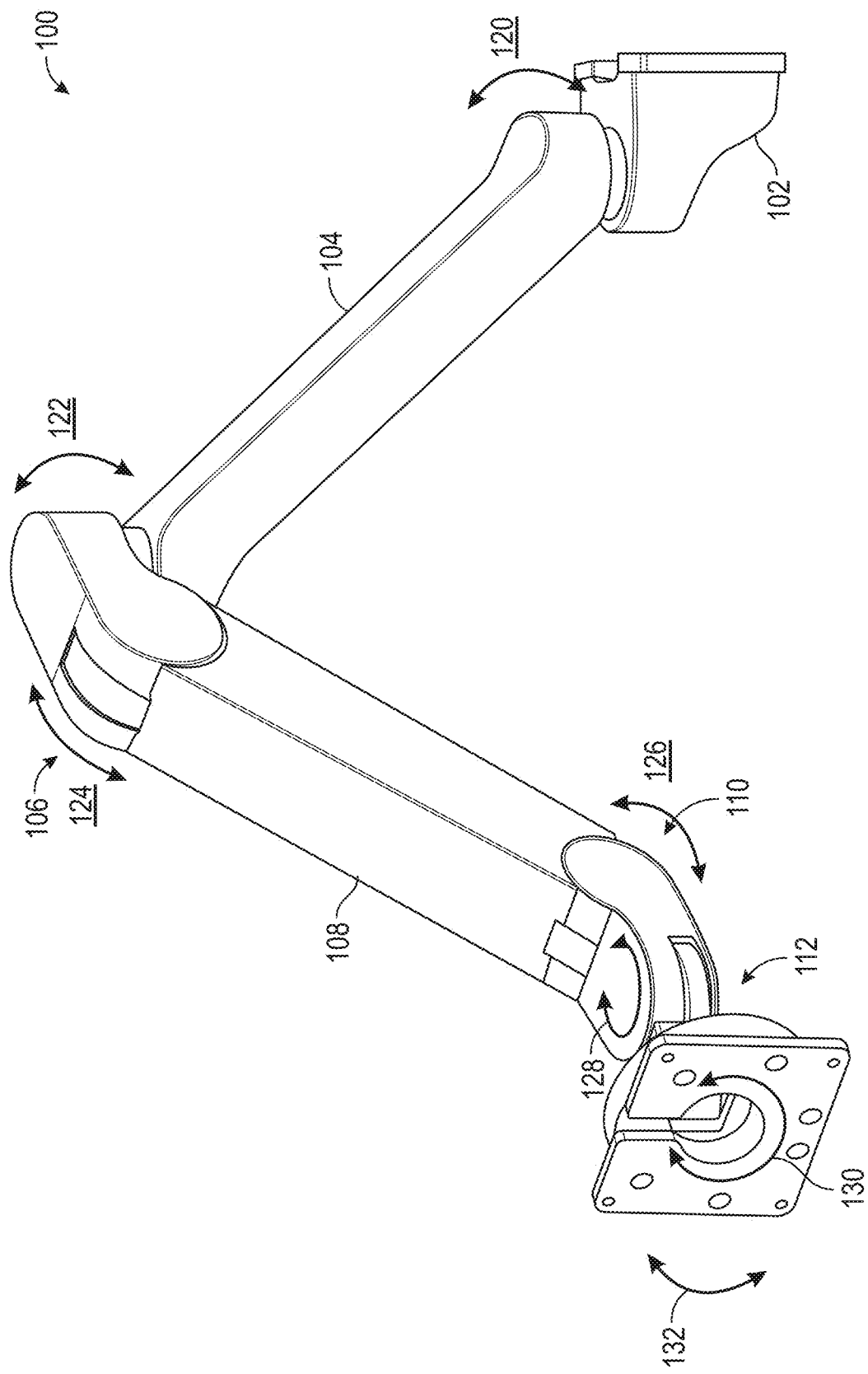
FIG. 5 is a front view of a base configuration of an illustrative tablet arm 100, in accordance with various embodiments.

FIG. 5 is a front view of a base configuration of an illustrative tablet arm 100, in accordance with various embodiments. The tablet arm 100 can include an extension 104, which can be implemented for light or heavy applications.

The tablet arm 100 can include a core arm 108 engaged to an extension arm 104. The core arm 108 can include a front mount 112 that is configured to engage with a screen (e.g., tablet, computer screen) via one or more fasteners. The extension arm 104 can allow for extension of the tablet arm 100 between various positions and can include a rear mount 102 configured to engage with an environmental structure, such as a wall, pole, work station, etc.

The tablet arm 100 can be positioned into various positions. For example, the extension arm 104 can be rotated horizontally 120 about the rear mount 102. As another example, the rear end 106 of the core arm 108 can be rotated horizontally 122 about the extension arm 104. As another example, the core arm 108 can be rotated vertically 124 in relation to the extension arm 104. As another example, the front mount 112 can be rotated generally horizontally 128 from the front end 110 of the core arm 108. As another example, the front mount 112 and attached tablet can be vertically tilted 132, such as to improve line of sight and/or to reduce reflection, at a desired elevation.

In another example, the orientation of the attached tablet display can be rotated 130, such as from landscape to portrait or from 0 degrees plus or minus a range (such as 0 plus or minus 90 or 135 degrees). In some embodiments, the orientation can be locked, such as by a screw or detent.

Figure 6:
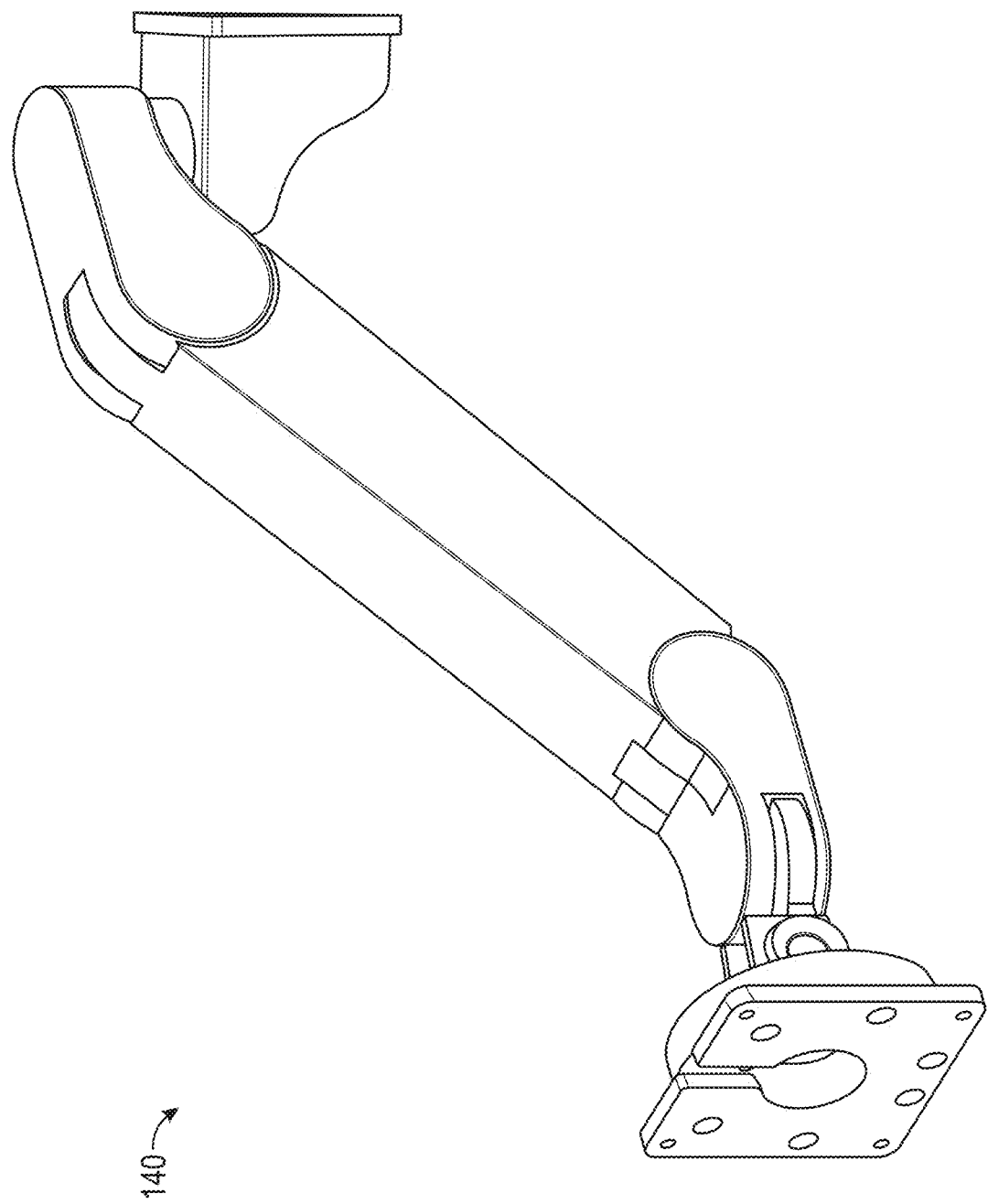
FIG. 6 is a front view of a base configuration of an illustrative tablet arm 140, in accordance with various embodiments.

FIG. 6 is a front view of a base configuration of an illustrative tablet arm 140, in accordance with various embodiments. As shown in FIG. 6, the tablet arm 140 can include only a core arm without an extension arm. The illustrative tablet arm 140 seen in FIG. 6 can also be positioned in a variety of positions as desired, such as including any of horizontal rotation vertical rotation, and tablet display tilting.

Figure 7A:
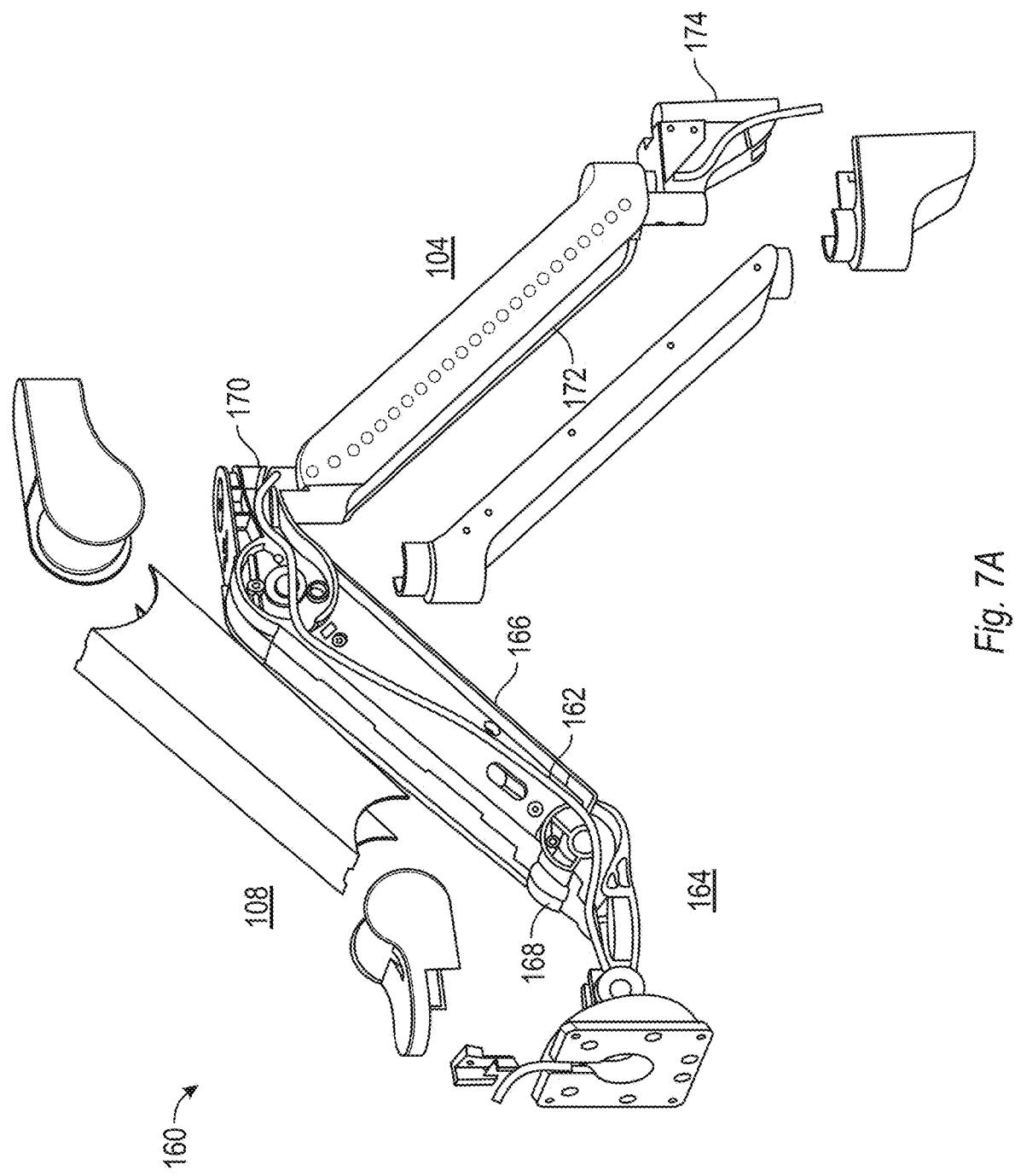
FIG. 7A is an exploded assembly view of a tablet arm, in accordance with various embodiments.

FIG. 7A is an exploded assembly view of a tablet arm 160, in accordance with various embodiments. As shown in FIG. 7A, the tablet arm 160 can include cabling 162 disposed within the core arm 166. The cables 162 can be routed 164 through the support arm structure, wherein the cabling 162 can be used to transfer power and/or send and receive data. The tablet arm 160 can include the core arm 166 extending from a front end to a rear end and configured to balance a mounted device, e.g., a tablet, within designed force-to-move limits.

FIG. 7B is a perspective view of a tablet arm 180a including a core support arm 108 pivotably connected to an extension arm 104 in a first rotated position, in accordance with various embodiments. FIG. 7C is an illustrative view of a tablet arm 180b including a core support arm pivotably connected to an extension arm 104, in a second rotated position, in accordance with various embodiments. The extension arm 104 as seen in FIG. 7B and FIG. 7C can be rotated 120 from the far left to the far right, while the rear hinge 170 can also be rotated 122 from a far left position to a far right position with respect to the extension arm 104. Similarly, the front tablet mount 112 can also be rotated 128 clockwise or counterclockwise with respect to the front hinge 110. In some embodiments, the rotation 120, 122, and/or 128 can provide a predetermined range, such as up to 360 deg (+/−180 degrees) rotation. In addition to enabling mechanical rotation of the one or more components of the arm throughout a wide range of motion, the arm 104 can be configured to provide robust internal routing of cabling 162, without binding or pinching within the predetermined range, which would otherwise limit cable life and/or break the cables. For example, in some embodiments, 360 degrees (+/−180 degrees) rotation allows the arm to reach these preferable positions while also limiting over-rotation. Over-rotation can be generally detrimental to cable life or can break cables.

In some embodiments, the tablet arm 180a, 180b can include a joint rotation stop structure that provide rotation within such a defined or predetermined range. For instance, some embodiments of the tablet arm can include joint rotation stop structures 200 that include a floating stop key 206, including stop faces that are movable within a predetermined range, using stop key stop faces that can float.

Figure 7D:
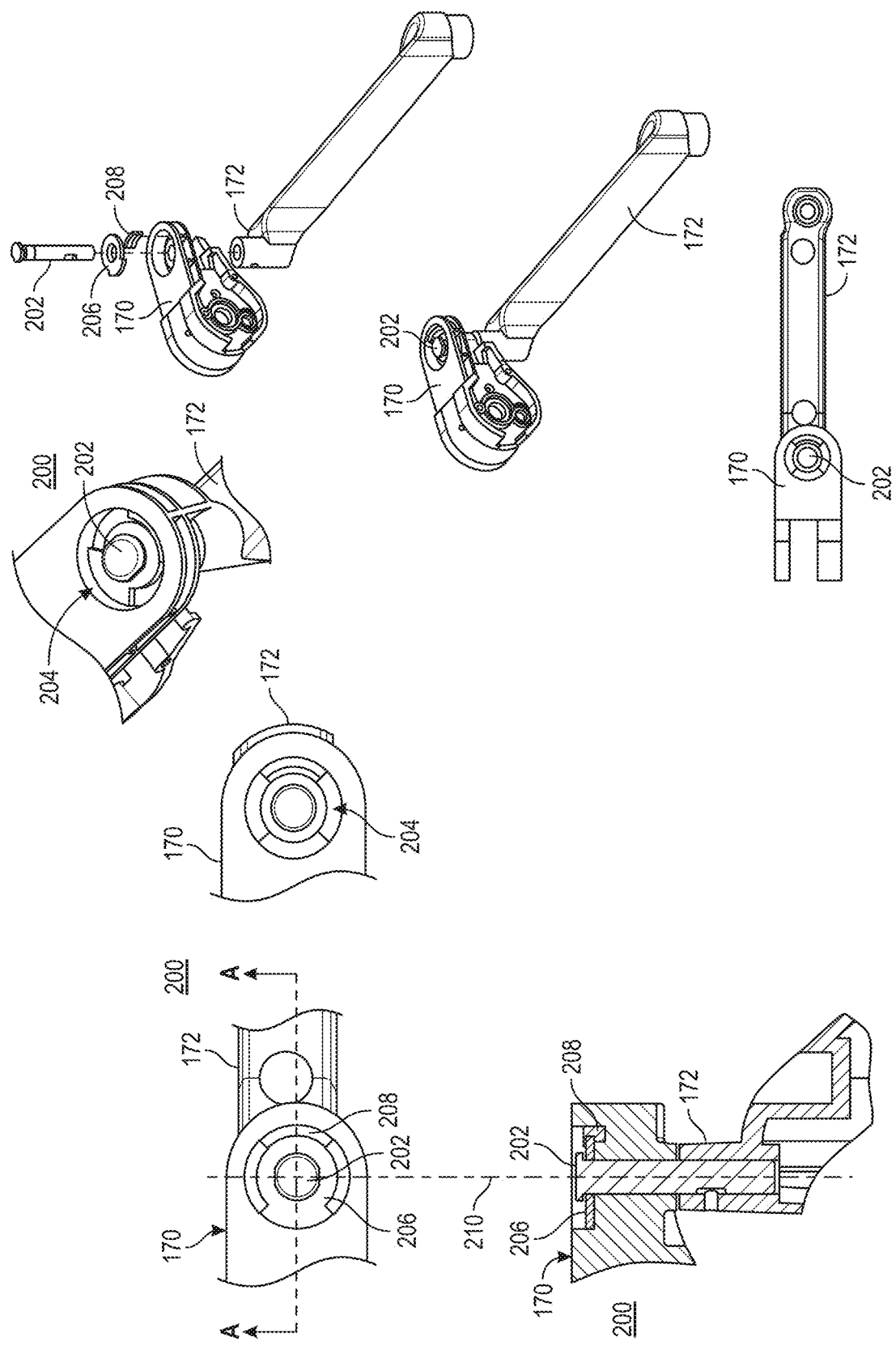
FIG. 7D provides detailed views of an illustrative joint rotation stop structure that includes a pivot stop structure, in accordance with various embodiments.

FIG. 7D provides detailed views of an illustrative joint rotation stop structure 200 that includes a pivot stop structure 200, in accordance with various embodiments. The pivot stop structure 200 can include a pivot stop disc 206 and a pivot stop floating key 208 located within a defined pivot region 204 of a rear hinge 170. At the zero-degree position shown in FIG. 7D, the key 208 can be within a defined range of rotation, and as such, is considered to be a floating key.

As seen in the partial cutaway view of FIG. 7D, the pivot stop disc 206 can be rotationally fixed to the core arm rear pivot post 202 about the pivot axis 210, while the pivot stop floating key 208 can be captured in the space defined between the pivot stop disc 206 and the rear hinge 170. The pivot stop floating key 208 can be free to rotate about the pivot axis 210 within the float space between the pivot stop disc 206 and the rear hinge 170, within the defined pivot region 204. The core arm rear pivot post 202 can be rotationally fixed to the extension structure 172 about the pivot axis 210.

FIG. 7E provides detailed views of an illustrative joint rotation stop structure that includes a pivot stop structure, in accordance with various embodiments. The joint rotation stop structure that includes a pivot stop structure can include a pivot stop disc 206 and a pivot stop floating key 208 located within a defined pivot region 204 of a rear hinge 170. The pivot stop structure can be rotated to a 180-degree counter-clockwise (CCW) position. In the illustrative 180-degree CCW position seen in FIG. 7E, the floating stop key 208 may have been moved (or pushed) by a counter-clockwise pivot rotation motion of the rear hinge 170 with respect to the rest of the assembly. In this position, the floating stop key 208 can be in a fully captured position, wherein a set of stop faces, as shown, can be active in preventing further counter-clockwise rotation of the rear hinge 170 with respect to the rest of the assembly. In this illustrative case, the rear hinge 170 can be rotated 180 degrees counter-clockwise to a stopped position, with respect to the extension structure 172.

Figure 7F:
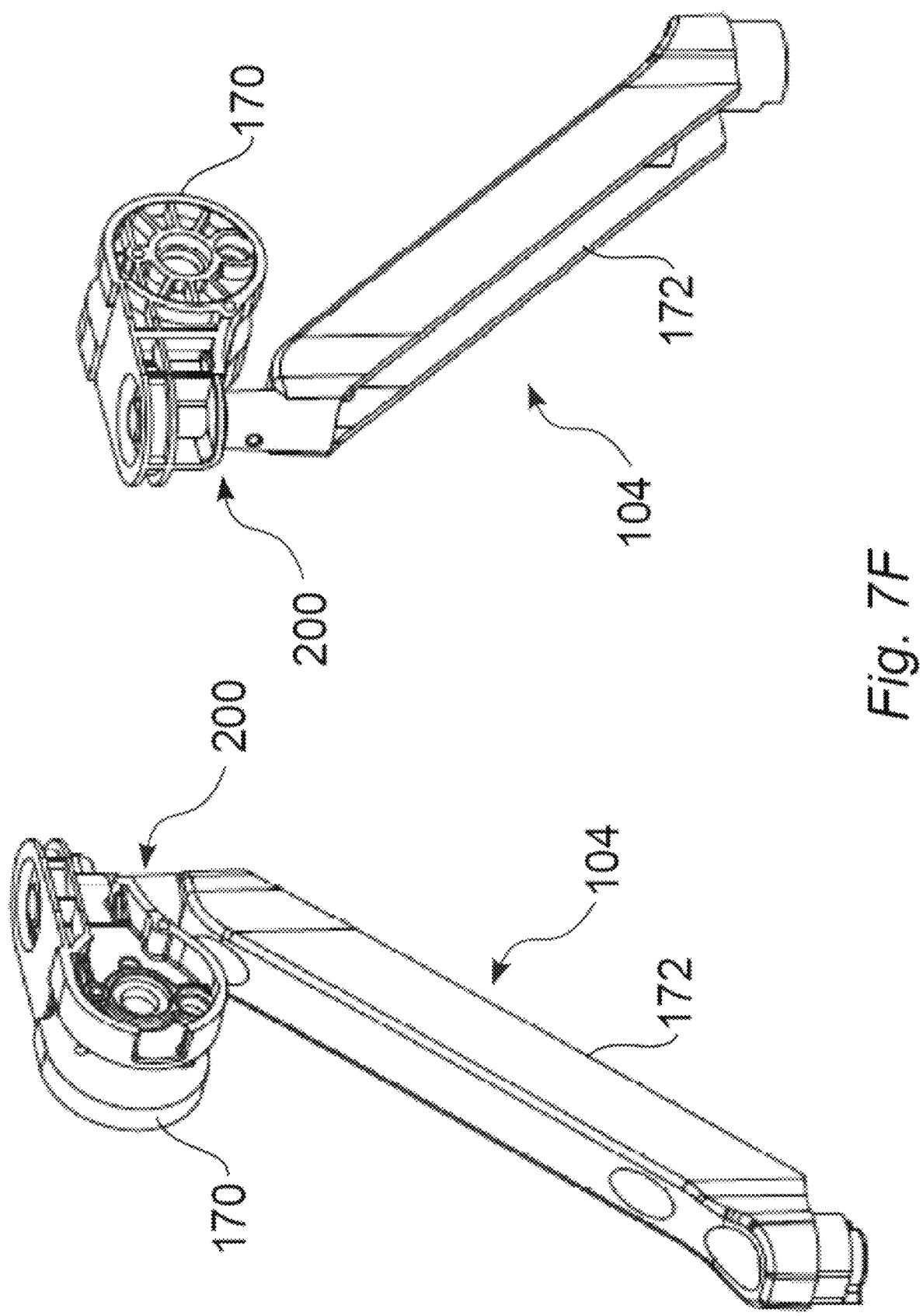
FIG. 7F provides assembly views of an illustrative tablet arm that includes an extension structure, and a joint rotation stop structure, in accordance with various embodiments.

FIG. 7F provides assembly views of an illustrative tablet arm that includes an extension structure 172, and a joint rotation stop structure 200, in accordance with various embodiments. The joint rotation stop structure 200 can include a pivot stop disc 206 and a pivot stop floating key 208 located within a defined pivot region 204 of a rear hinge 170, in which the pivot stop structure is rotated to a 180-degree counter-clockwise (CCW) position.

FIG. 7G provides detailed views of an illustrative joint rotation stop structure that includes a pivot stop structure, in accordance with various embodiments. The pivot stop structure can include a pivot stop disc 206 and a pivot stop floating key 208 located within a defined pivot region 204 of a rear hinge 170. The pivot stop structure can be rotated to a 180 degree clockwise (CW) position. In the illustrative 180 degree CW position seen in FIG. 7G, the floating stop key 208 may have been moved, i.e., pushed, by a clockwise pivot rotation motion of the rear hinge 170 with respect to the rest of the assembly, i.e., with respect to the extension structure 172 In this position, the floating stop key 208 can be in a fully captured position, wherein a set of stop faces, as shown, are active in preventing further clockwise rotation of the rear hinge 170 with respect to the rest of the assembly. In this illustrative case, the rear hinge 170 may have rotated 180 degrees clockwise to a stopped position, with respect to the extension structure 172.

FIG. 7H provides assembly views of an illustrative tablet arm that includes an extension structure 172, and a joint rotation stop structure 200 that includes a pivot stop structure 200, in accordance with various embodiments. The pivot stop structure 200 can include a pivot stop disc 206 and a pivot stop floating key 208 located within a defined pivot region 204 of a rear hinge 170, in which the pivot stop structure is rotated to a 180 degree clockwise (CW) position.

In some embodiments, the floating stop key 208 is movable, such as within a track or tunnel that is dynamically formed by the pivoting components.

While the illustrative joint rotation stop structures 200 are described with respect to rotation between a core arm 108 and an extension arm 104, the joint rotation stop structures 200 can readily be implemented for other rotatable joints or interfaces, such as between an extension arm 104 and a rear mount 102, or between the front end 110 of a core arm 108 and a connected component, e.g., a from mount 112. Additionally, the joint rotation stop structures 200 can be configured to be used for other applications, such as for any mechanical pivot having specific rotational requirements and/or that includes cabling that would otherwise be prone to wear or damage.

In some embodiments, the joint rotation stop structures 200 can be implemented to limit unwanted rotation of an articulated support arm 42, such as to reduce the risk of collisions with other objects. In embodiments that are implemented for support arm structures having integrated power and/or signal cables 162, the joint rotation stop structures 200 can be implemented to prevent cables 162 from winding up around the joints, and breaking. In some embodiments, the joint rotation stop structure can be configured to allow the core arm 108 to pivot a full 360 degrees (+/−180 degrees).

The floating stop key 208 can include stop faces that can move within a design range, because the stop key stop faces can float. Essentially, a key 208 can be configured to move within a dynamically formed track or tunnel created by the pivoting pieces.

Embodiments of the illustrative joint rotation stop structures 200 can be configured to prevent cables 162 from winding up around the joints and breaking. While the joint rotation stop structure 200 can be configured to provide rotational movement within other defined ranges, some current embodiments allow the core arm to pivot a full +/−180 degrees (yielding a defined range of 360 degrees).

While some illustrative embodiments of the tablet arm 42 are specifically configured for use an overbed table, the tablet arm 42 and corresponding defined range of rotation can readily be configured for a wide variety of uses, with one or more design constraints, such as including any of specified ranges of motion, forces to move, mounting type, stationary, mobile operation, and/or mounted devices.

As discussed above, embodiments of the joint rotation stop structures 200 can be configured to prevent cables 162 from winding up around the joints and breaking, and/or can be configured to limit unwanted rotation, for example to reduce the risk of collisions with other objects.

In an illustrative embodiment, the joint rotation stop structure 200 can allow for a full 360 degrees (+/−180 degrees) range of rotation, which is often preferred when the main function is to prevent cable winding. In an illustrative embodiment to be used between a rear hinge 170 and an extension structure 172, the design rotation range can be defined as: Rotation range=(angle length of path in rear hinge 170)+(angle length of path in the stop disc 206)−2* (angle length of the floating key 208).

In the case of the illustrative configuration that FIGS. 7D, 7E and 7G represent, the rotation range=(270)+(270)−2*(90)=360 degrees (+/−180 deg). In some embodiments, the rotation range can be set, up to limits of physical possibility, to be more or less than the illustrative rotation range described with respect to the embodiments shown in FIGS. 7D, 7E and 7G.

For instance, for some embodiments of the tablet arm that do not include an extension structure 172, such as for a direct connection to a wall mount 102, the range of motion can be 180 degrees (+/−90). For such an embodiment, the joint rotation stop structure 200 can be configured with 180 degrees of floating key length, such as by including two floating keys 208 in the assembly 200 (e.g., 90 degrees+90 degrees=180).

Figure 8:
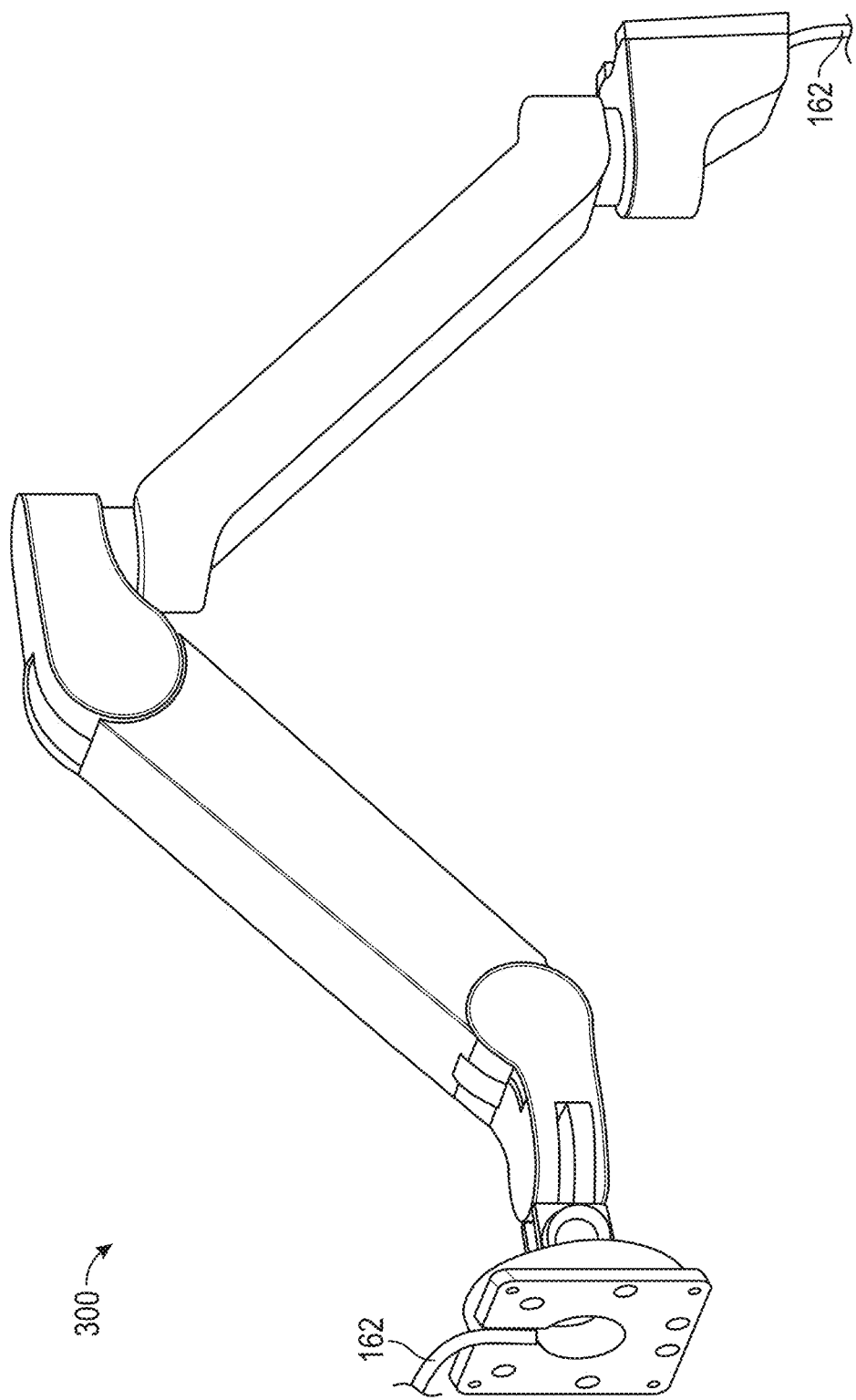
FIG. 8 is an assembled view of an illustrative tablet arm that includes an extension 104, in accordance with various embodiments.

FIG. 8 is an assembled view of an illustrative tablet arm 300 that includes an extension, in accordance with various embodiments. As seen in FIG. 8, the core arm can include a core arm structure, a front hinge 162, and a rear hinge, as well as covers. As also seen in FIG. 8, the extension arm can include an extension structure, as well as one or more covers, and the rear mount includes a rear mount structure. One or more cables 162 can be exposed from the rear mount structure.

As discussed above, illustrative embodiments of the tablet arm can be positioned in a variety of positions as desired, such as including any of horizontal rotation 120, 122, or 128, vertical rotation 124, 126, and tablet display tilting 130. Some embodiments can be rotated about one or more axes, e.g., pivot axis 210, within a defined or predetermined range, such as to allow controlled movement within an environment, while avoiding undesired positioning with respect to the environment or other equipment, and/or to prevent damage or binding to internal cables 162.

Some stop designs are typically, for example, a stop tooth on the rear hinge and a stop tooth on the extension structure that engage at the limit of rotation. These tooth features (or pins, walls) can take up space, each on each component. Therefore, rotation may be limited to less than 360 degrees, because the features may be unable to, by design, overlap and occupy the same space. In some embodiments, such stops can be used, e.g., between a rear channel mount 102 and an extension arm 104, which can readily be configured to provide about +/−90 degrees of rotation.

In some embodiments, the tablet arm can be implemented to provide fully concealed routing of cables 162 between opposing ends of the tablet arm. The cables 162 can be accessible via snap fit covers, for easy installation and maintenance. As such, the exterior as well as the interior can is readily cleanable. Some embodiments of the tablet arm include asymmetric construction, whereby one or more cables 162 can be routed to the side of the structural componentry, such as to aid in any of manufacturing, maintenance, and cleaning. At the front end of the tablet arm, the cable 162 can be routed to avoid kinking or binding, throughout the range of rotation 130 and tilt 132 of the tablet screen.

Figure 9:
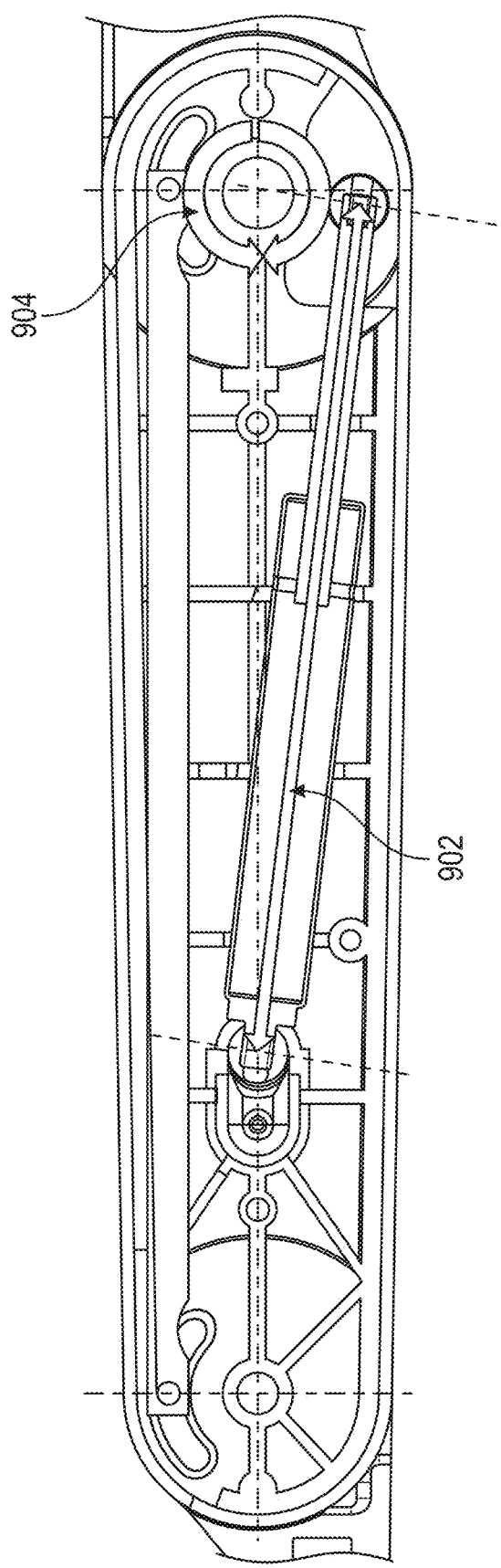
FIG. 9 is a partial cutaway view of an adjustable core arm structure for an illustrative tablet arm, in accordance with various embodiments.

FIG. 9 is a partial cutaway view of an adjustable core arm structure for an illustrative tablet arm 320, in accordance with various embodiments. The adjustable support arm can include both a gas spring 902, as well as a friction element 904, in which the friction element 904 can provide resistance and torque.

Figure 10:
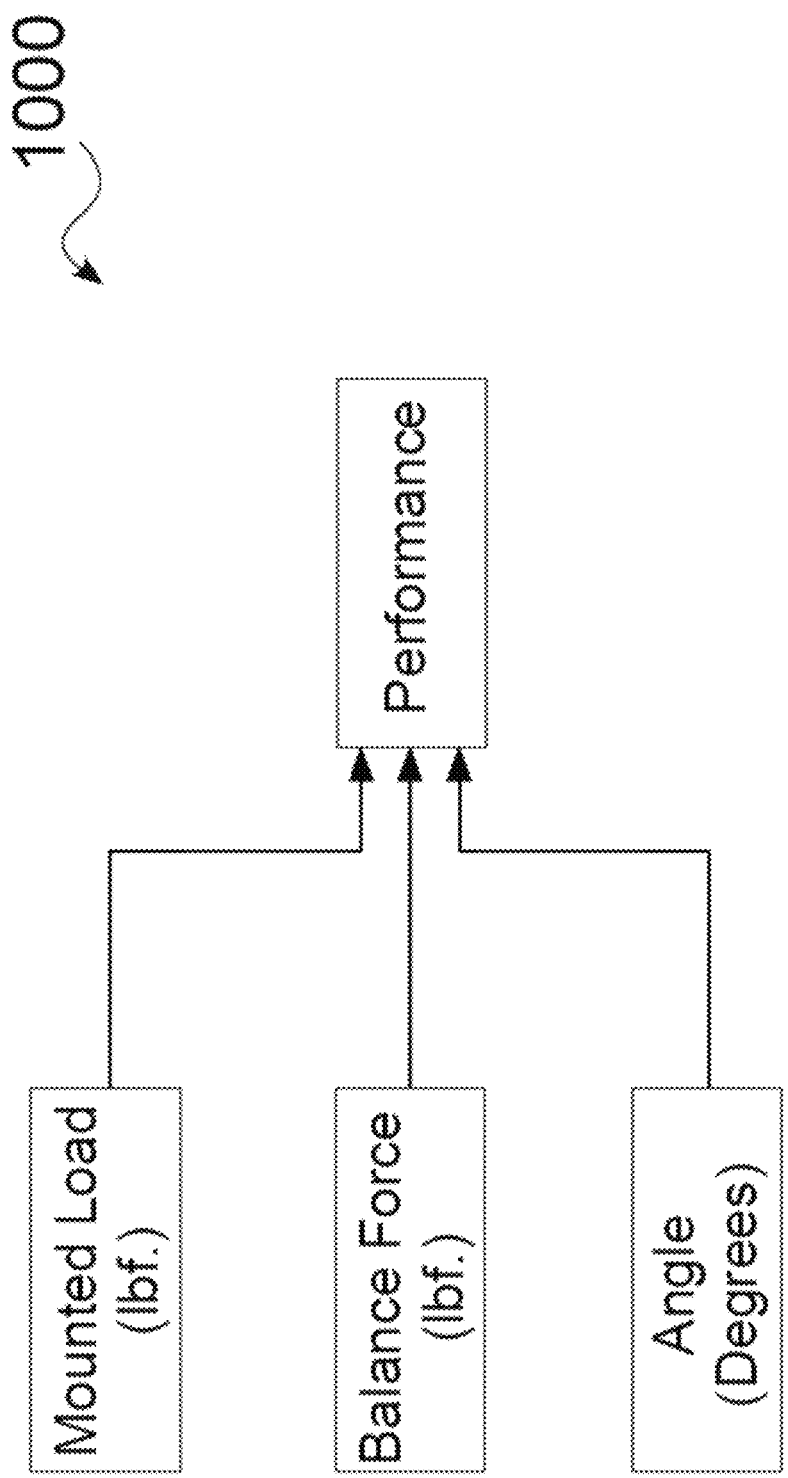
FIG. 10 is a schematic diagram hat illustrates design parameters to be considered for different mounted loads, in accordance with various embodiments.

FIG. 10 is a schematic diagram 1000 that illustrates design parameters to be considered for different mounted loads, in accordance with various embodiments. A design parameter to be consider can be based on a user force required to move a mounted tablet up or down within a range of motion. For example, if too little force is needed to move the mounted tablet up or down from one angle to another, the mounted screen may undesirably sink or float, creating a functional issue. As well, if too much force is needed to move the mounted tablet up or down from one angle to another, such movement may also be undesirable. As such, embodiments of the support arm can be configured to provide acceptable movement performance for an intended load, with a combination of precise friction and spring force.

Tablet Arm Counterbalance Design

Illustrative embodiments of the tablet core arm disclosed herein can be configured to use a non-adjustable gas spring counterbalance force with a non-adjustable friction pack element for up/down resistance to support a range of payloads.

The gas spring counterbalance can be set for about the middle of the payload range, and then the friction can be used to offset the sink or float that would occur for lighter or heavier payloads. With this design there is relatively more friction in the arm, which can result in different user experience and engineering considerations. Understanding desirable User Force preferences can be a critical design input.

In a first theoretical case, it can be assumed that there is a mid-range payload, with the arm perfectly gas spring counterbalanced, and with equal friction resistance up and down. In this case, the amount of force to move the arm up and down can comprise friction resistance and the amount of force required to move the arm up and down can be the same.

As an example, the User Force to move up is +2 lb and down is −2 lb. The Differential User Force is then +(+2 lb)+(−2 lb)=0. In this example, the differential User Force has no bias. With a payload that weighs 1 lb more than the mid-range, the friction holds the arm up. The User Force to move up would be 3 lb and down would be −1 lb. The Differential User Force is +(+3 lb)+(−1 lb)=2 lb. Therefore, 2 lbf more would be needed to move up vs. down. There is a +(up) bias.

With a payload that weighs 1 lb less than the mid-range, the friction can hold the arm down. The User Force to move up would be +1 lb and down would be −3 lb. The Differential User Force is +(+1 lb)+(−3 lb)=−2 lb. In this example, the user can need 2 lb more to move down vs. up. There is a −(down) bias.

Note that in the case where friction up and down is perfectly equal, the Differential User Force is simply twice (2×) that of the gas spring counterbalance mismatch, because the friction zero's out in the equation.

The scenario used above to explain user forces is a simplified theoretical situation. The gas spring counter balance can vary in mismatch over the arm travel. Also, the spring force can have a manufacturing tolerance, so the mid-range will be different from arm to arm. The internal friction pack also can have a manufacturing tolerance so the resistance will vary from arm to arm, although in a given arm the up/down amount from a given friction pack may generally be the same. In addition, the gas spring can have its own linear friction and the pivoting joints of the arm at the axles, link bar pins, and to a lesser degree the gas spring pivots, also have friction with kinematic relationships with arm position. The stack-up of mismatches and tolerances can be accounted for in the engineering design.

For "counter balance," it can be a fundamental requirement that the arm supports a mounted payload in any static position when the mounted payload is within the specified product limits. This can be true for all combinations of mismatches and tolerances and needed vertical positions. The approach can include a worst-case total stack-up analysis including all element tolerances. For "User Forces," as with the counter balance analysis, the worst-case mismatch and tolerance stack-up can be used. However, when analyzing User Differential Force, it can be recognized that for a given arm the friction is symmetrical up and down at given height and therefore the friction tolerance does not influence the Differential force, although it does affect the overall force. It is likewise for the gas spring tolerance. However, the mismatch of all the support forces vs. the perfect balance forces does result in a variation of the differential force to over the arm travel, to a high degree because of the arm geometry (e.g., friction torque vs. linear force) so the case is not as simple as the idealized case used in the Explanation of User Forces. Calculations for the analysis of arm balance can include the requirements below.

Example User Force Requirements

Studies have been performed to learn user preferences that were analyzed to define desirable functional requirements, based on an exemplary design goals. It should be understood that, while the following specifications are generally pertinent to the goals of one or more products, the acceptable and preferred specifications may, and likely would, vary for other products with different payloads, etc. For example, the disclosed design parameters can be scaled "up" for heavier, bulkier, devices, where the specific numbers will be different, and similarly can be scaled down for light and/or compact embodiments.

For instance, a user force to move the arm UP may include any of feels "good" equaling to +0.5 lbf to +4.5 lbf (most to least desirable), feels "okay" equaling to +0.5 lbf to +5.5 lbf, and/or feels "bad" being outside of the "okay" range.

As another example, a user force to move the arm DOWN may include any of feels "good" equaling to −1.0 lbf to −5.5 lbf, feels "okay" equaling to −0.5 lbf to −6.5 lbf, and/or feels "bad" equaling to outside the "okay" range.

As another example, an example User Differential Force that is >=0, then +8.5 lbf to 0 lbf (that is If User Force |UP| is more than or equal to |DOWN|). Similarly, if the User Differential Force<0, then 0 lbf to −4.0 lbf (that is If User Force |UP| is less than |DOWN|).

Figure 11:
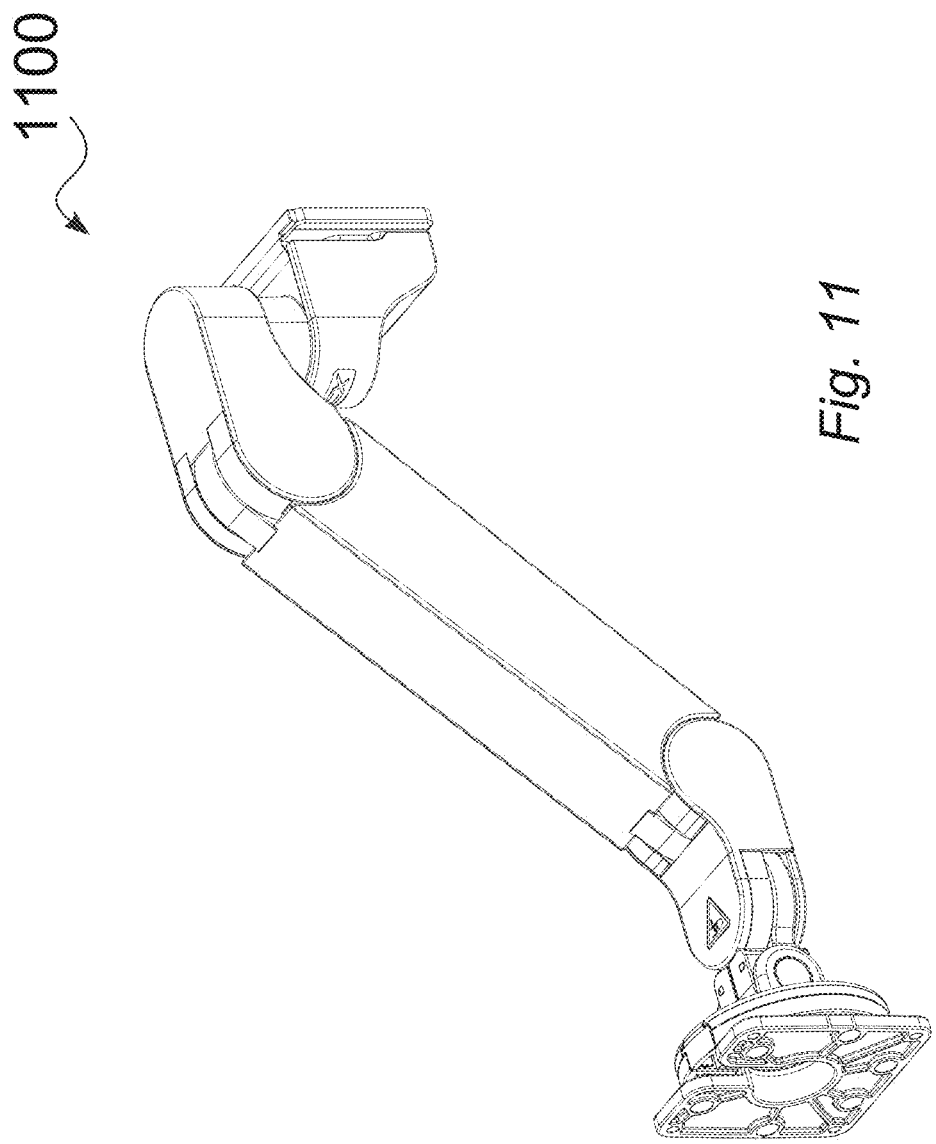
FIG. 11 is a front perspective view of an illustrative tablet arm without extension, in a downward position, in accordance with various embodiments.

FIG. 11 is a front perspective view of an illustrative tablet arm 1100, without extension, in a downward position, in accordance with various embodiments.

Figure 12:
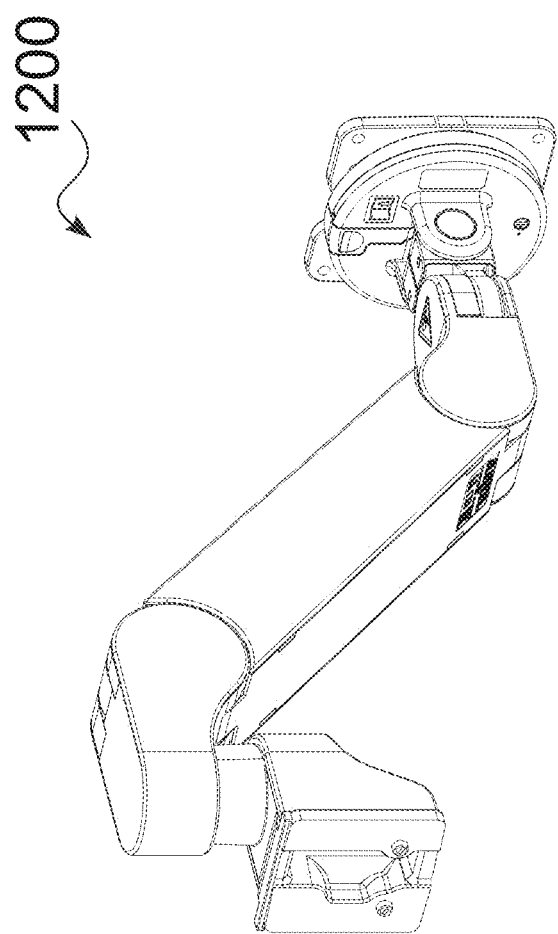
FIG. 12 is a rear perspective view of an illustrative tablet arm, without extension, in a downward position, in accordance with various embodiments.

FIG. 12 is a rear perspective view of an illustrative tablet arm 1200, without extension, in a downward position, in accordance with various embodiments.

Figure 13:
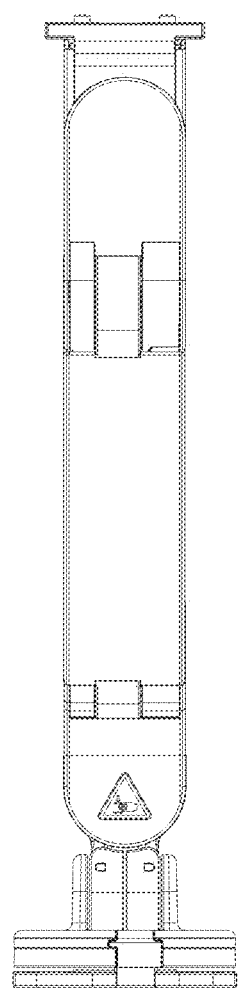
FIG. 13 is a top view of an illustrative tablet arm, without extension, in a downward position, in accordance with various embodiments.

FIG. 13 is a top view of an illustrative tablet arm 1300, without extension, in a downward position, in accordance with various embodiments.

Figure 14:
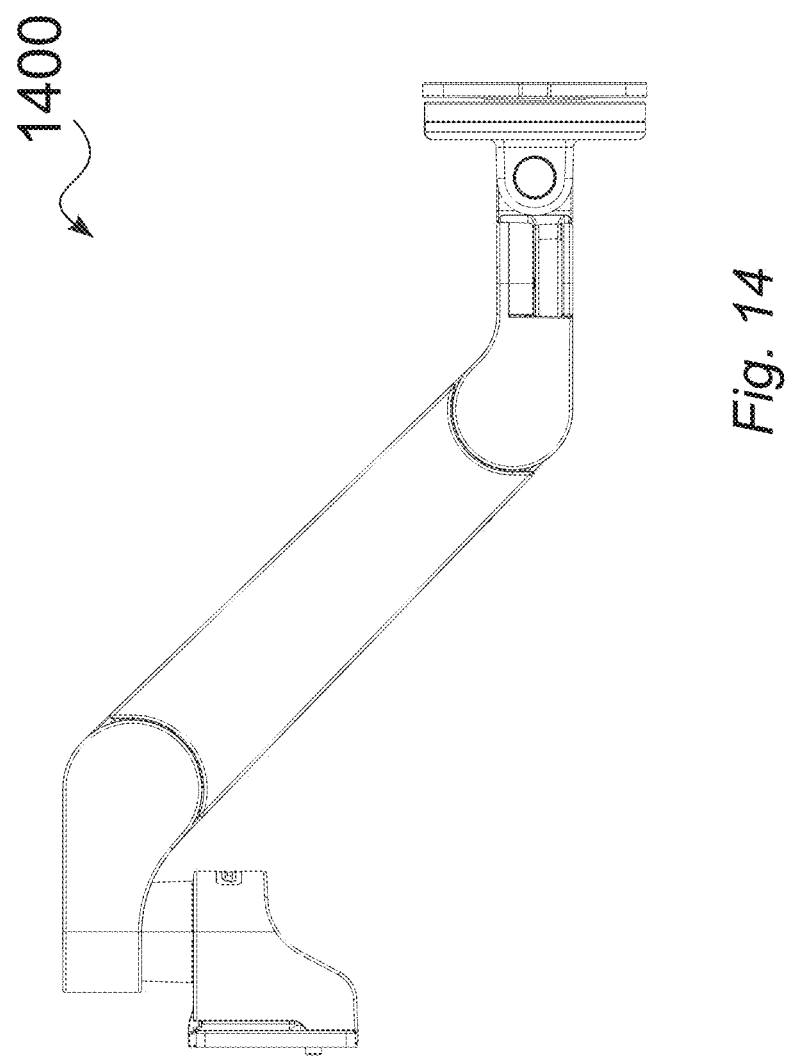
FIG. 14 is a right side view of an illustrative tablet arm, without extension, in a downward position, in accordance with various embodiments.

FIG. 14 is a right-side view of an illustrative tablet arm 1400, without extension, in a downward position, in accordance with various embodiments.

Figure 15:
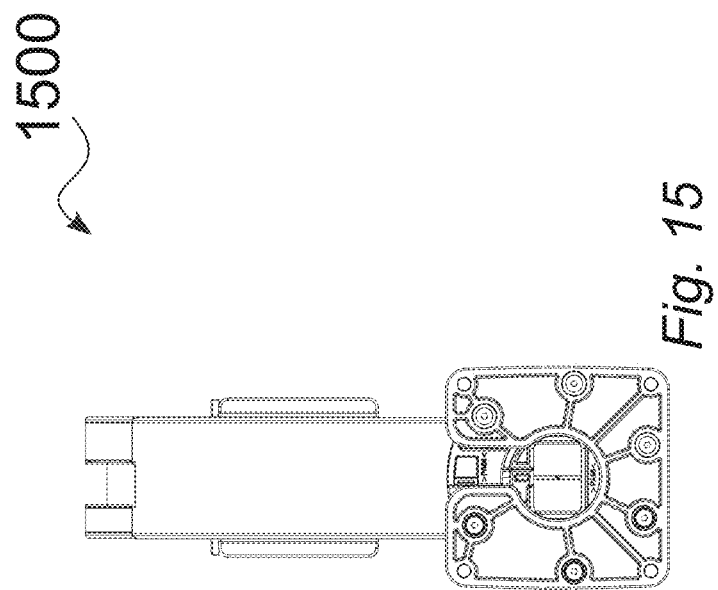
FIG. 15 is a front (tablet-side) view of an illustrative tablet arm, without extension, in a downward position, in accordance with various embodiments.

FIG. 15 is a front (tablet-side) view of an illustrative tablet arm 1500, without extension, in a downward position, in accordance with various embodiments.

Figure 16:
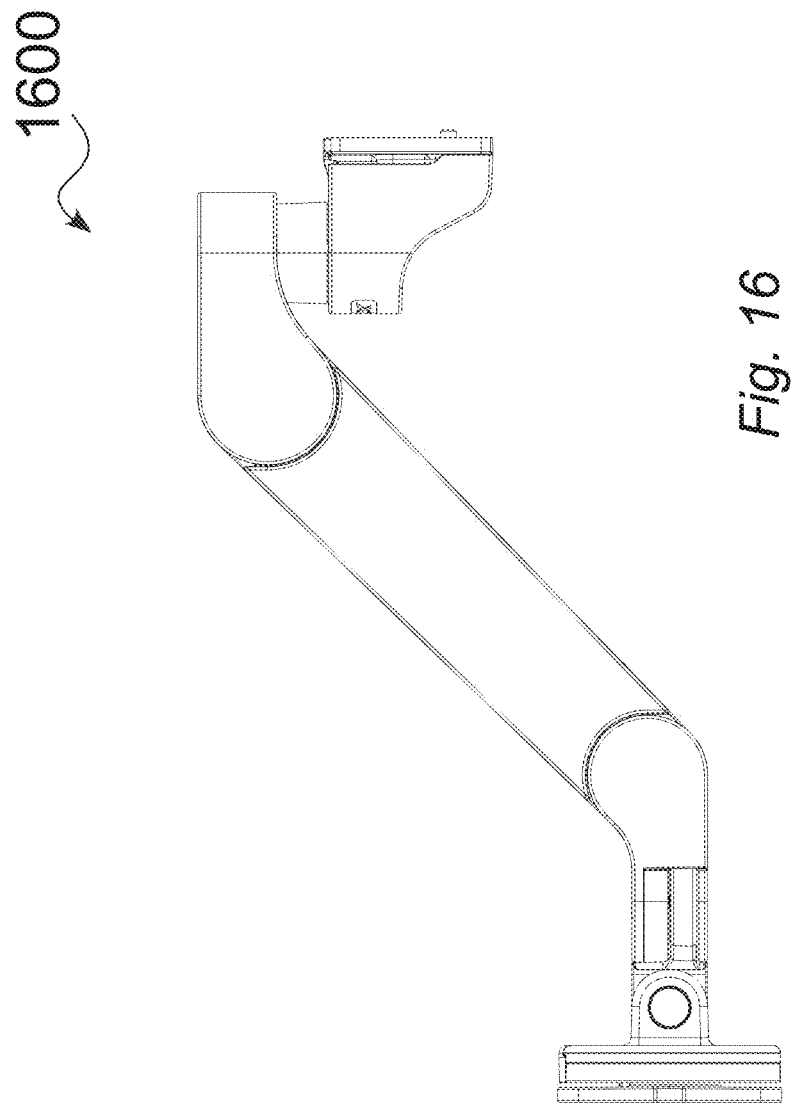
FIG. 16 is a left side view of an illustrative tablet arm, without extension, in a downward position, in accordance with various embodiments.

FIG. 16 is a left side view of an illustrative tablet arm 1600, without extension, in a downward position, in accordance with various embodiments.

Figure 17:
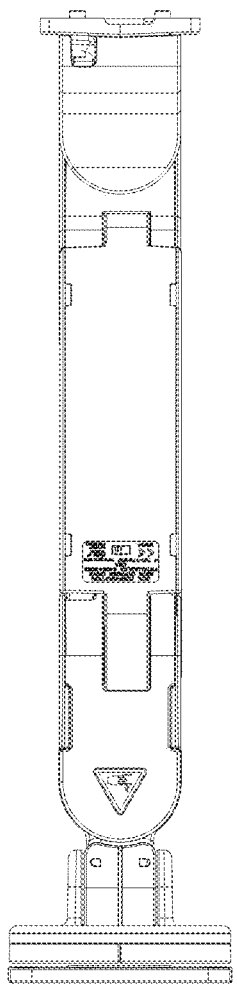
FIG. 17 is a bottom view of an illustrative tablet arm, without extension, in a downward position, in accordance with various embodiments.

FIG. 17 is a bottom view of an illustrative tablet arm 1700, without extension, in a downward position, in accordance with various embodiments.

Figure 18:
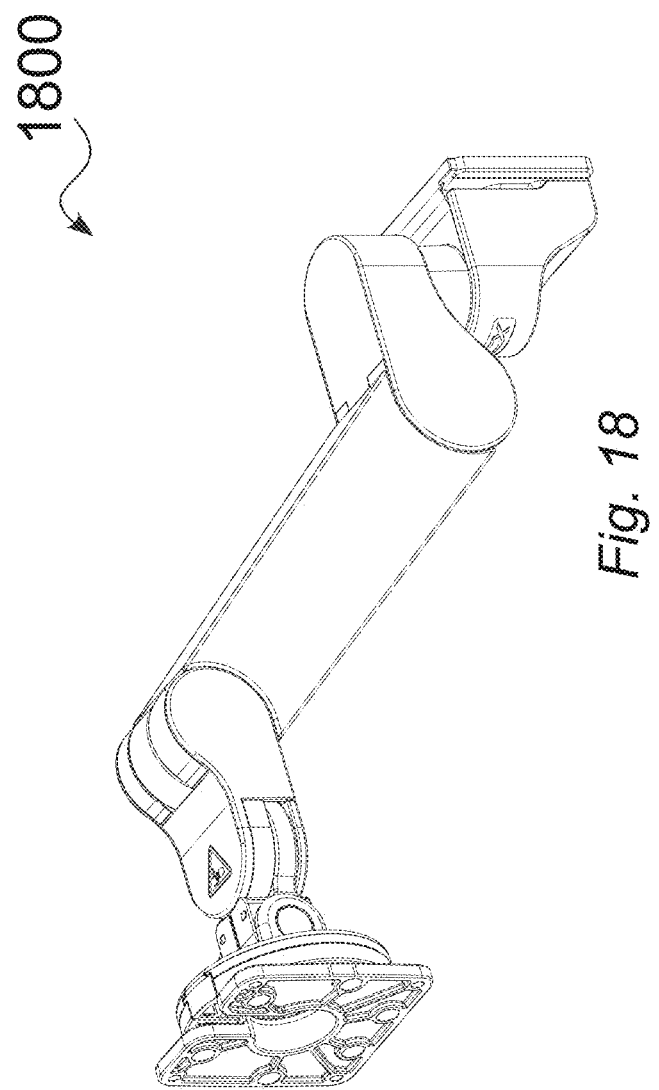
FIG. 18 is a front perspective view of an illustrative tablet arm, without extension, in an upward position, in accordance with various embodiments.

FIG. 18 is a front perspective view of an illustrative tablet arm 1800, without extension, in an upward position, in accordance with various embodiments.

Figure 19:
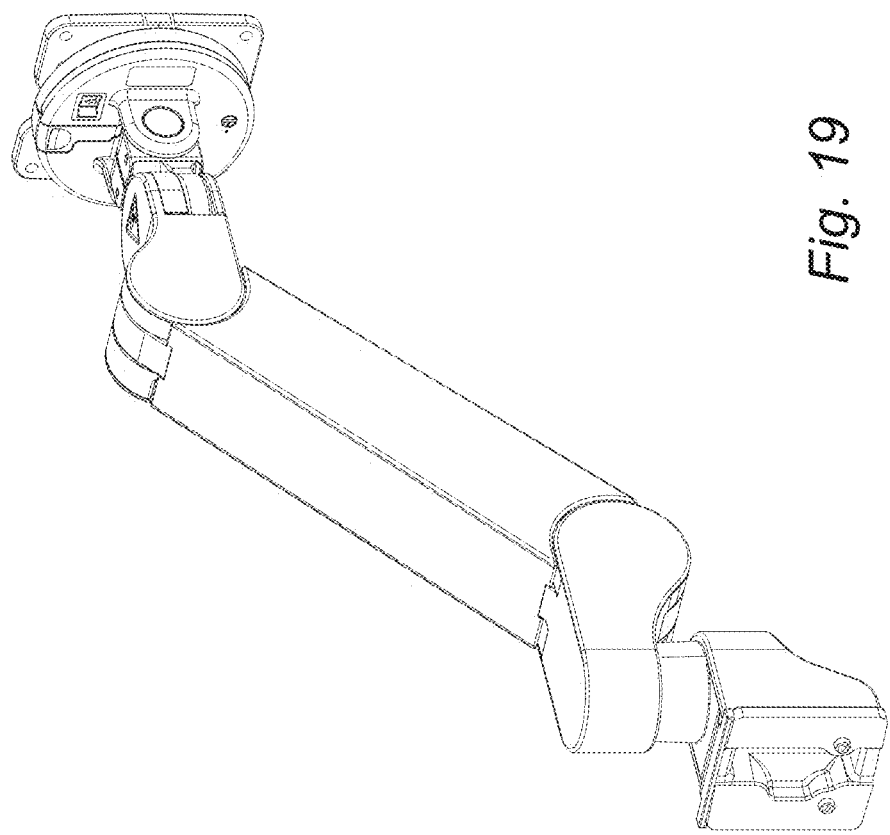
FIG. 19 is a rear perspective view of an illustrative tablet arm, without extension, in an upward position, in accordance with various embodiments.

FIG. 19 is a rear perspective view of an illustrative tablet arm 1900, without extension, in an upward position, in accordance with various embodiments.

Figure 20:
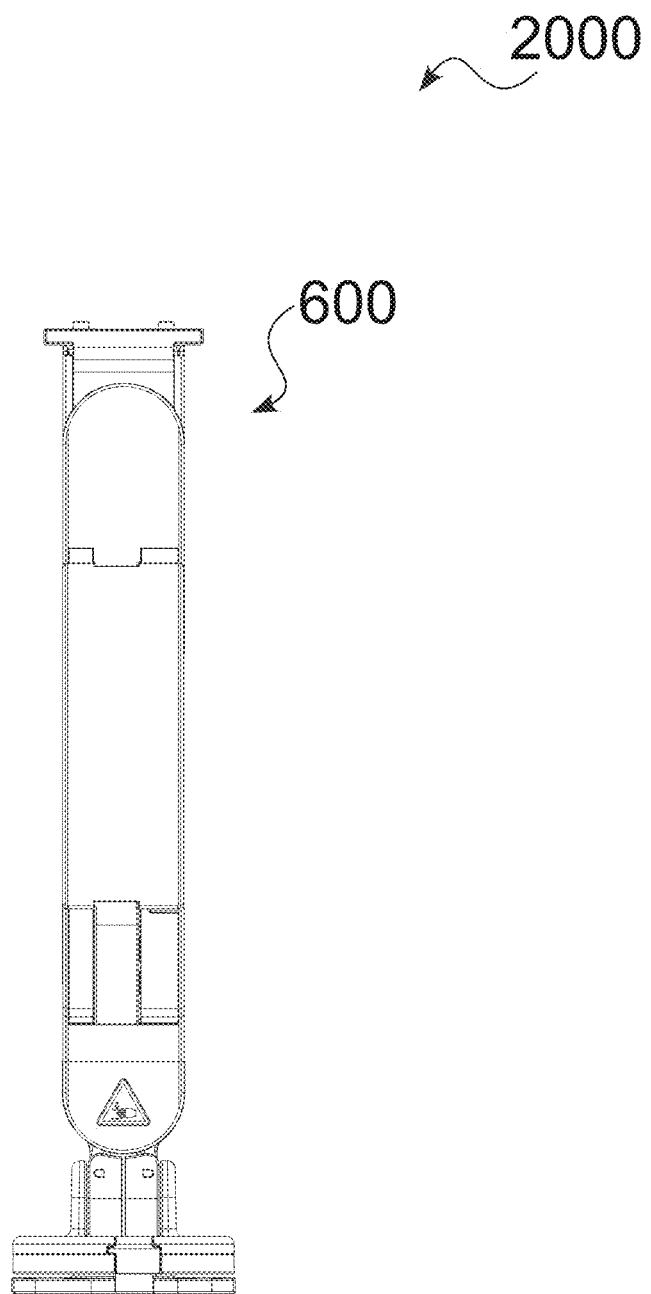
FIG. 20 is a top view of an illustrative tablet arm, without extension, in an upward position, in accordance with various embodiments.

FIG. 20 is a top view of an illustrative tablet arm 2000, without extension, in an upward position, in accordance with various embodiments.

Figure 21:
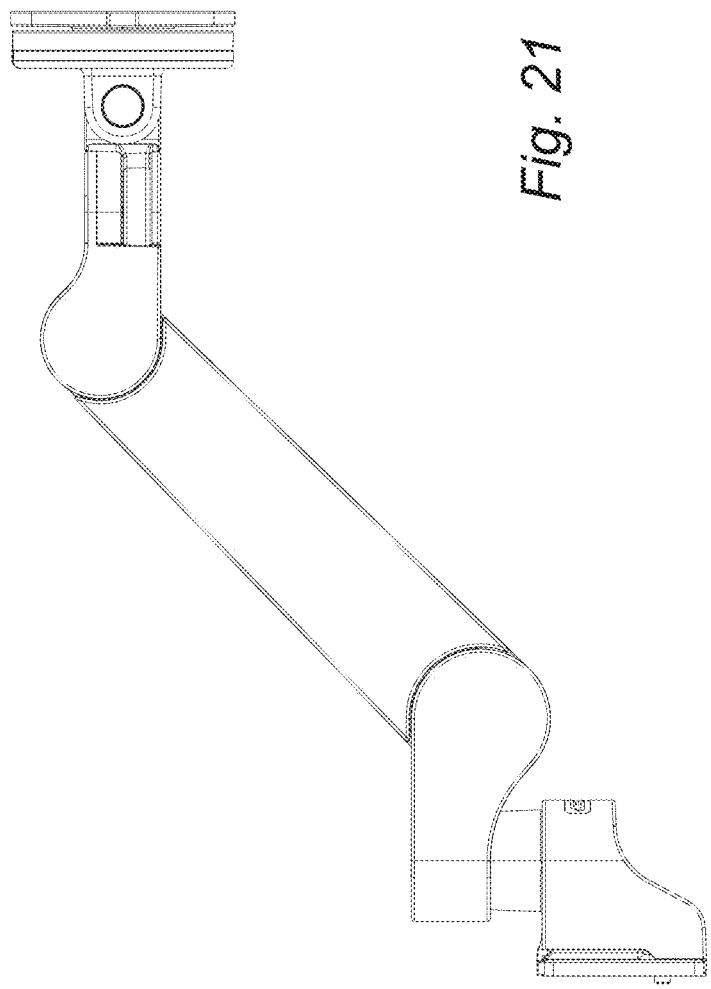
FIG. 21 is a right side view of an illustrative tablet arm, without extension, in an upward position, in accordance with various embodiments.

FIG. 21 is a right-side view of an illustrative tablet arm 2100, without extension, in an upward position, in accordance with various embodiments.

Figure 22:
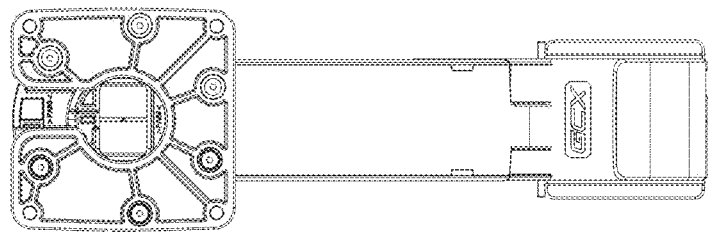
FIG. 22 is a front (tablet-side) view of an illustrative tablet arm, without extension, in an upward position, in accordance with various embodiments.

FIG. 22 is a front (tablet-side) view of an illustrative tablet arm 2200, without extension, in an upward position, in accordance with various embodiments.

Figure 23:
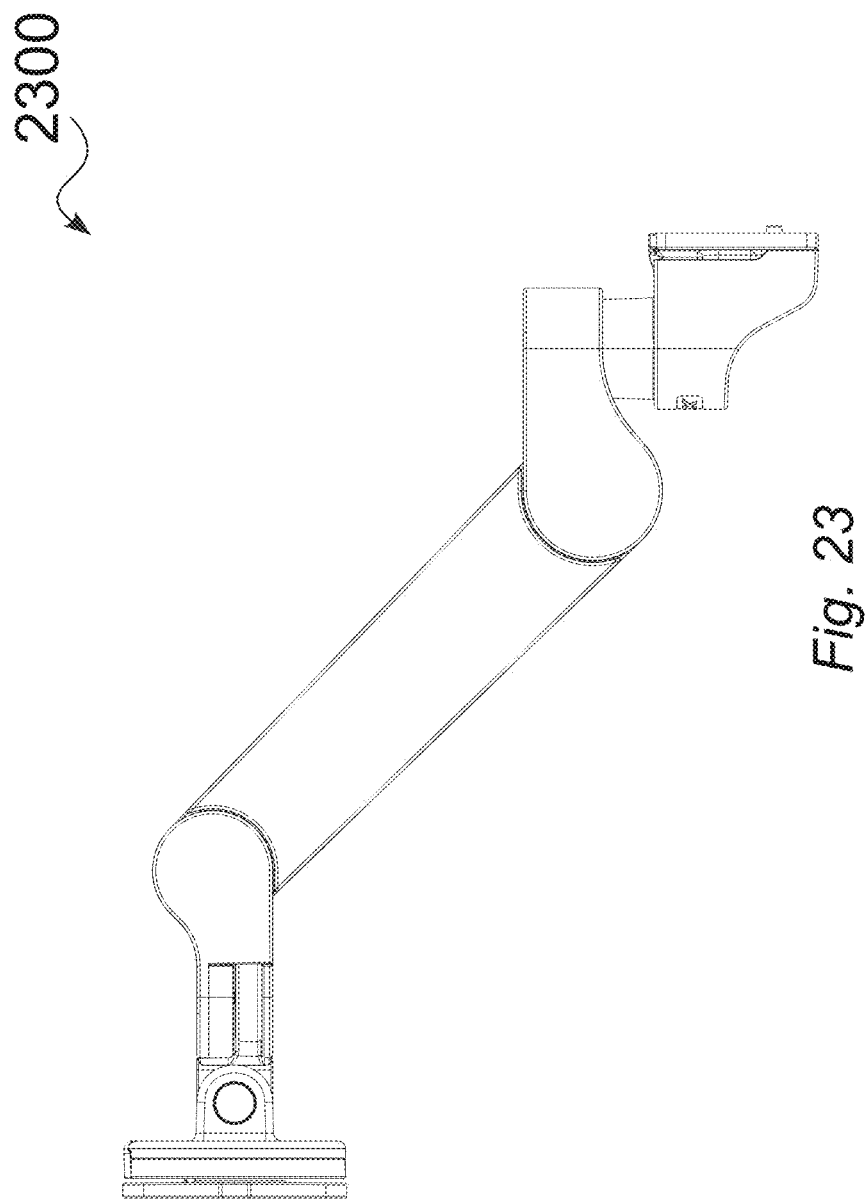
FIG. 23 is a left side view of an illustrative tablet arm, without extension, in an upward position, in accordance with various embodiments.

FIG. 23 is a left side view of an illustrative tablet arm, without extension 2300, in an upward position, in accordance with various embodiments.

Figure 24:
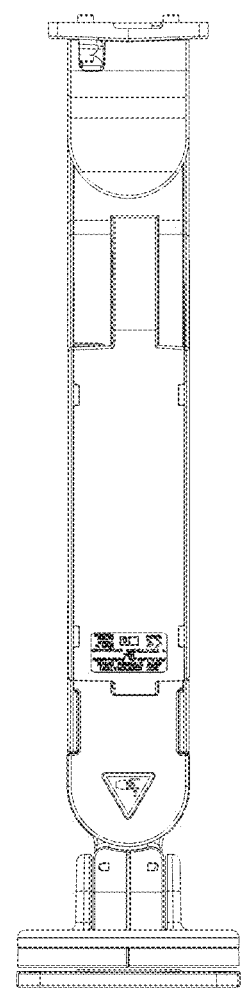
FIG. 24 is a bottom view of an illustrative tablet arm, without extension, in an upward position, in accordance with various embodiments.

FIG. 24 is a bottom view of an illustrative tablet arm 2400, without extension, in an upward position, in accordance with various embodiments.

Figure 25:
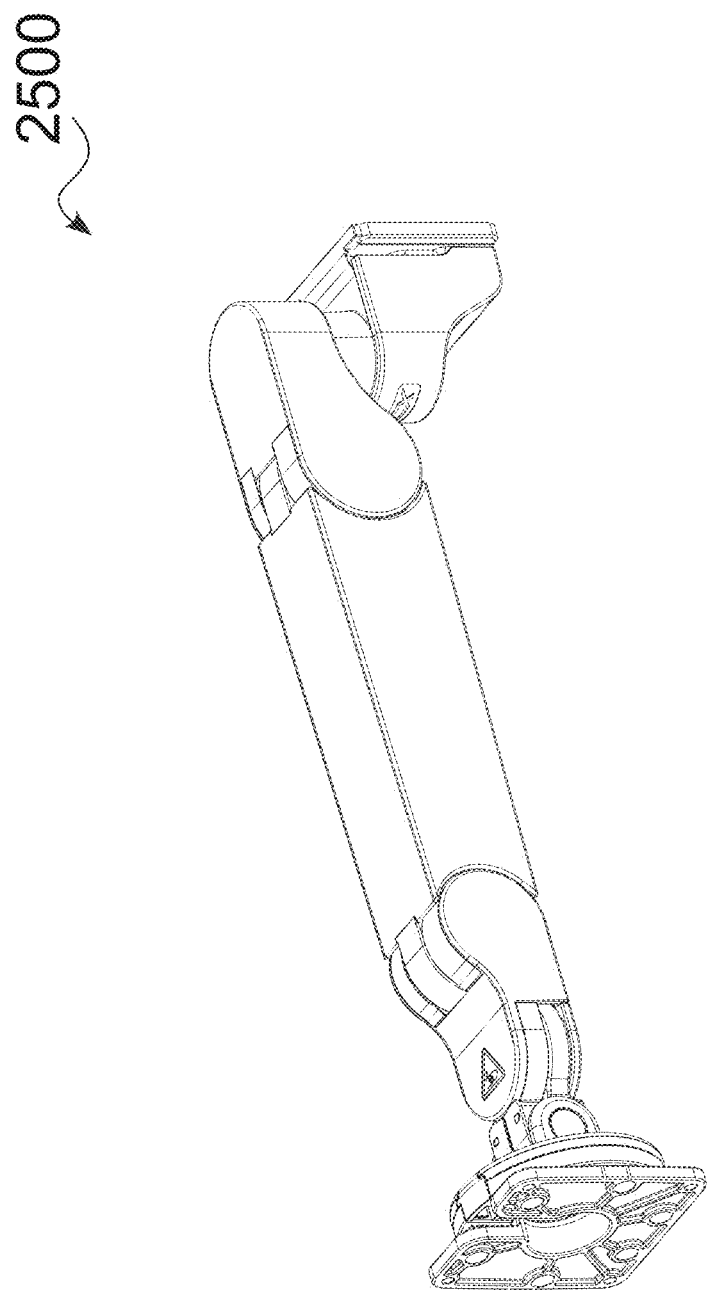
FIG. 25 is a front perspective view of an illustrative tablet arm, without extension, in a horizontal position, in accordance with various embodiments.

FIG. 25 is a front perspective view of an illustrative tablet arm 2500, without extension, in a horizontal position, in accordance with various embodiments.

Figure 26:
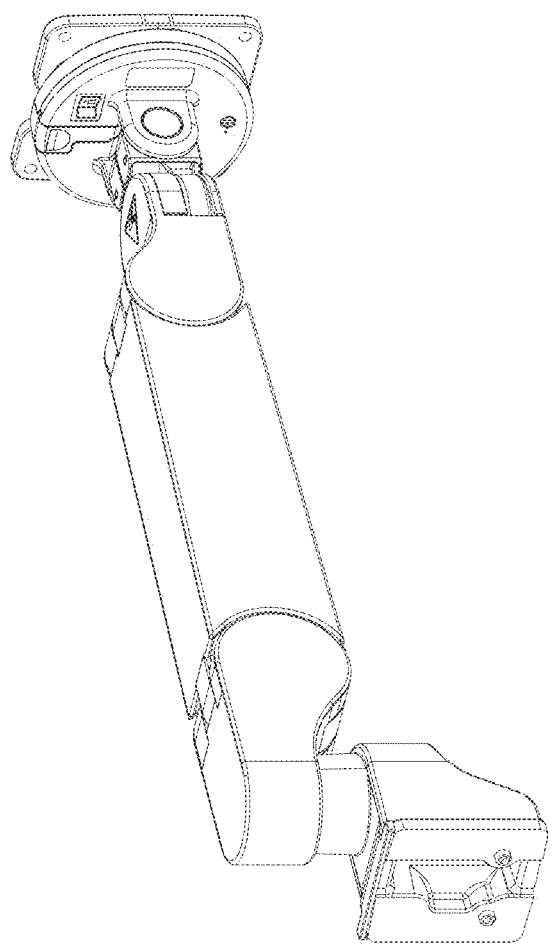
FIG. 26 is a rear perspective view of an illustrative tablet arm, without extension, in a horizontal position, in accordance with various embodiments.

FIG. 26 is a rear perspective view of an illustrative tablet arm 2600, without extension, in a horizontal position, in accordance with various embodiments.

Figure 27:
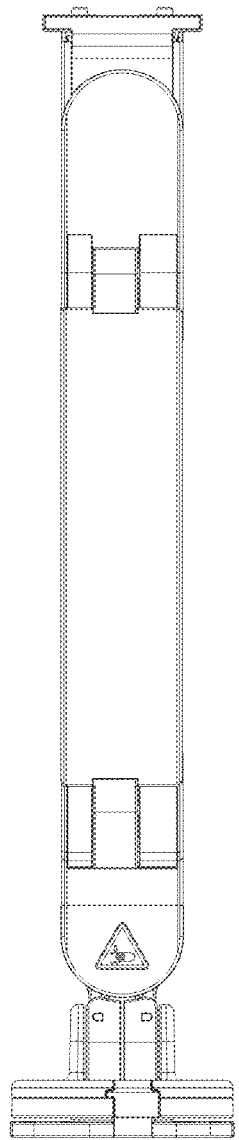
FIG. 27 is a top view of an illustrative tablet arm, without extension, in a horizontal position, in accordance with various embodiments.

FIG. 27 is a top view of an illustrative tablet arm 2700, without extension, in a horizontal position, in accordance with various embodiments.

Figure 28:
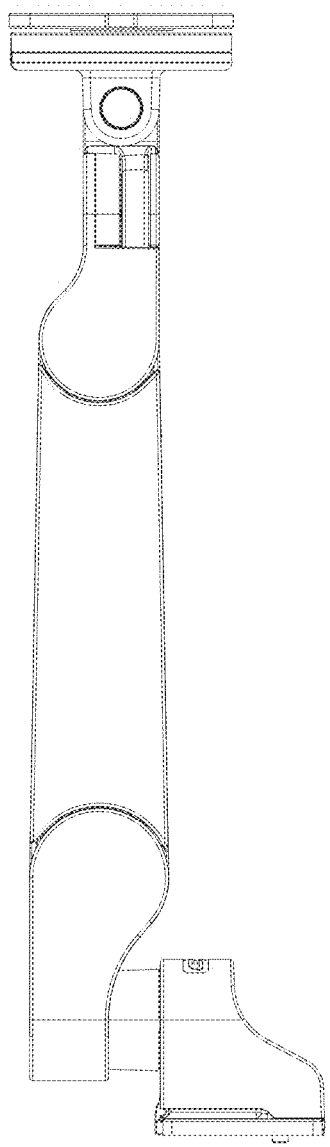
FIG. 28 is a right side view of an illustrative tablet arm, without extension, in a horizontal position, in accordance with various embodiments.

FIG. 28 is a right-side view of an illustrative tablet arm 2800, without extension, in a horizontal position, in accordance with various embodiments.

Figure 29:
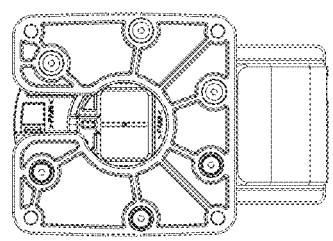
FIG. 29 is a front (tablet-side) view of an illustrative tablet arm, without extension, in a horizontal position, in accordance with various embodiments.

FIG. 29 is a front (tablet-side) view of an illustrative tablet arm 2900, without extension, in a horizontal position, in accordance with various embodiments.

Figure 30:
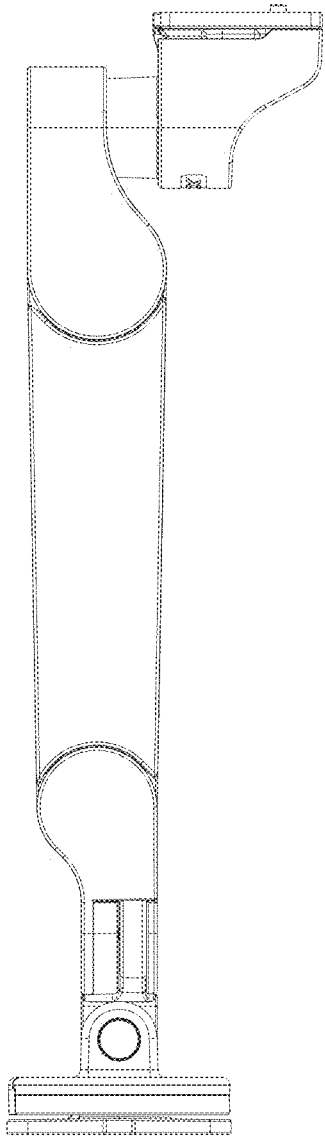
FIG. 30 is a left side view of an illustrative tablet arm, without extension, in a horizontal position, in accordance with various embodiments.

FIG. 30 is a left side view of an illustrative tablet arm 3000, without extension, in a horizontal position, in accordance with various embodiments.

Figure 31:
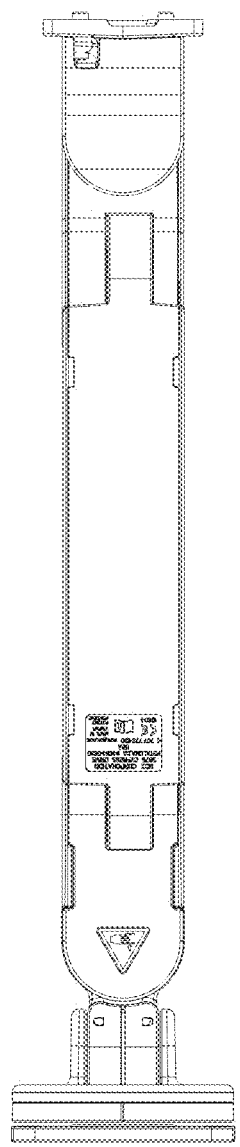
FIG. 31 is a bottom view of an illustrative tablet arm, without extension, in a horizontal position, in accordance with various embodiments.

FIG. 31 is a bottom view of an illustrative tablet arm 3100, without extension, in a horizontal position, in accordance with various embodiments.

Figure 32:
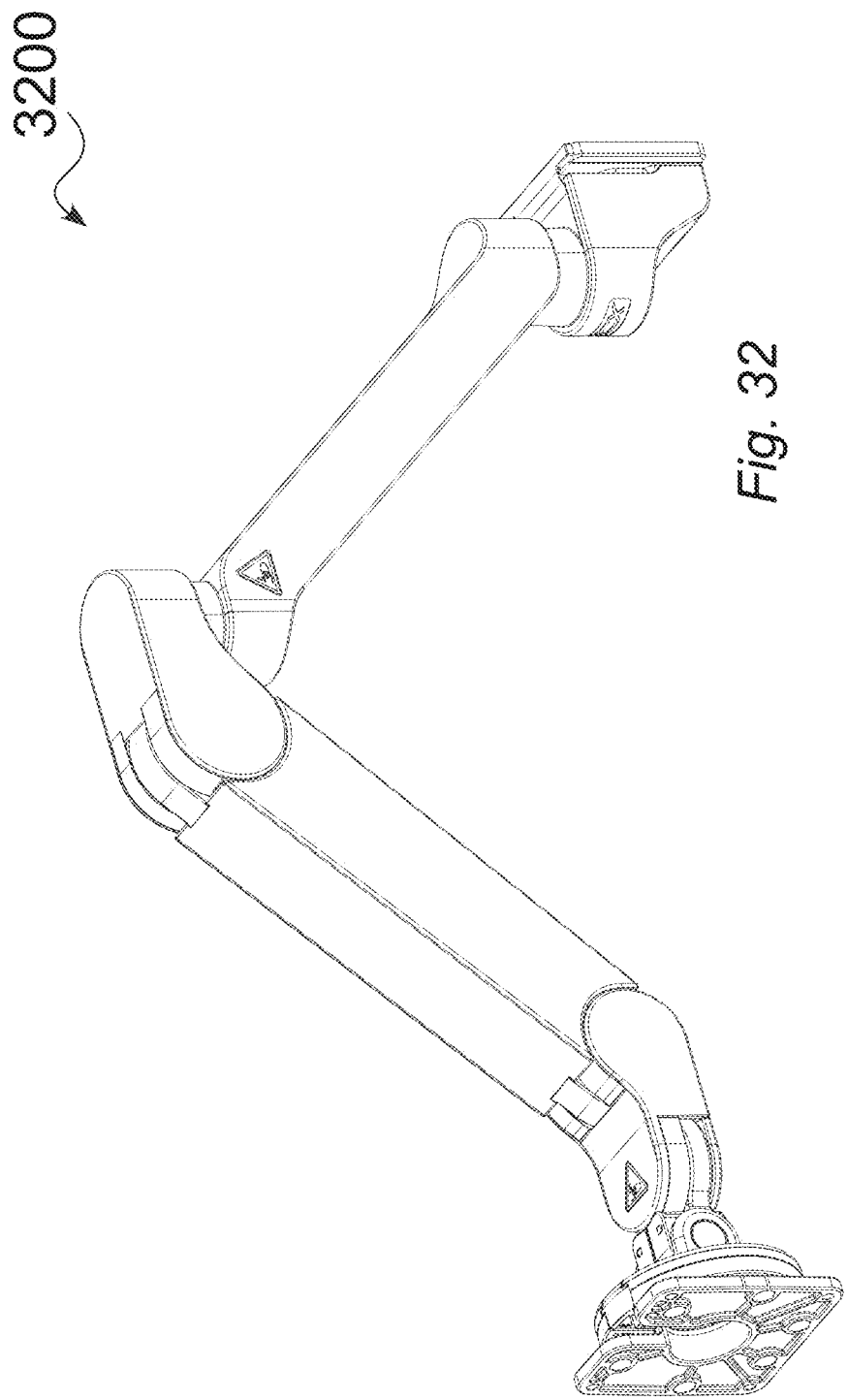
FIG. 32 is a front perspective view of an illustrative tablet arm, with extension, in a downward position, in accordance with various embodiments.

FIG. 32 is a front perspective view of an illustrative tablet arm 3200, with extension, in a downward position, in accordance with various embodiments.

Figure 33:
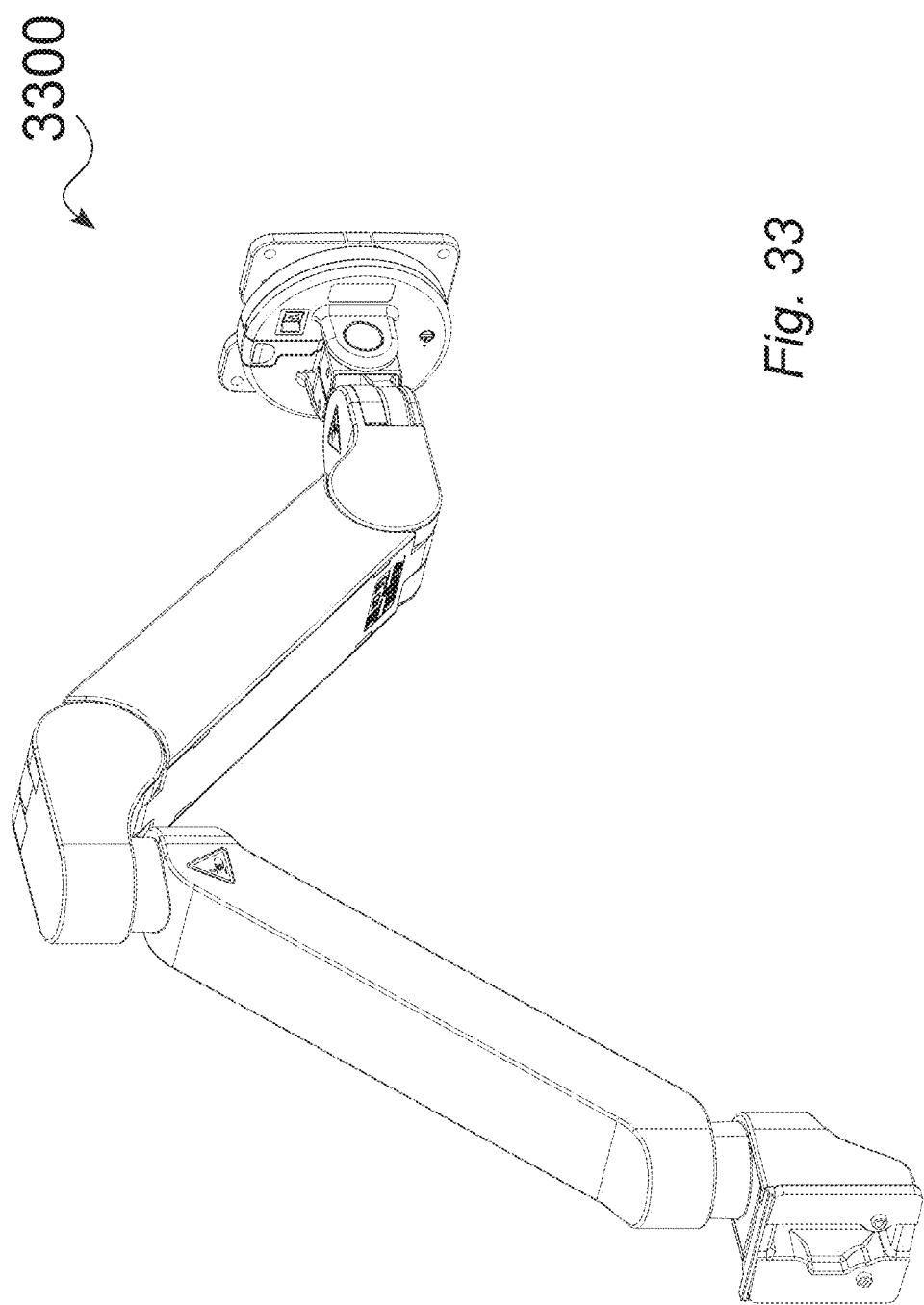
FIG. 33 is a rear perspective view of an illustrative tablet arm, with extension, in a downward position, in accordance with various embodiments.

FIG. 33 is a rear perspective view of an illustrative tablet arm 3300, with extension, in a downward position, in accordance with various embodiments.

Figure 34:
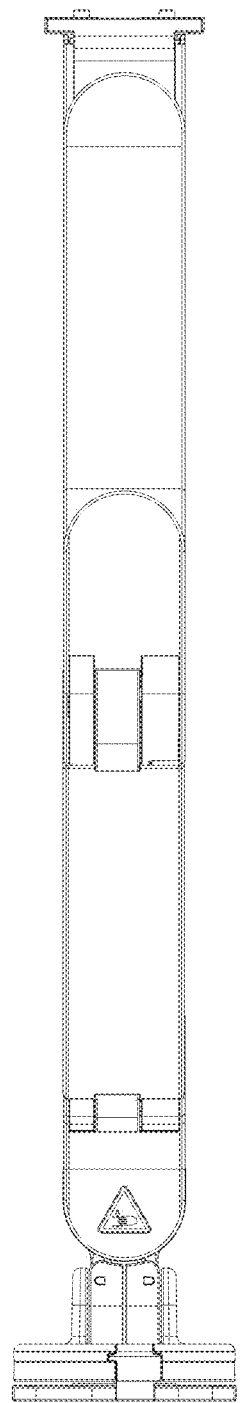
FIG. 34 is a top view of an illustrative tablet arm, with extension, in a downward position, in accordance with various embodiments.

FIG. 34 is a top view of an illustrative tablet arm 3400, with extension, in a downward position, in accordance with various embodiments.

Figure 35:
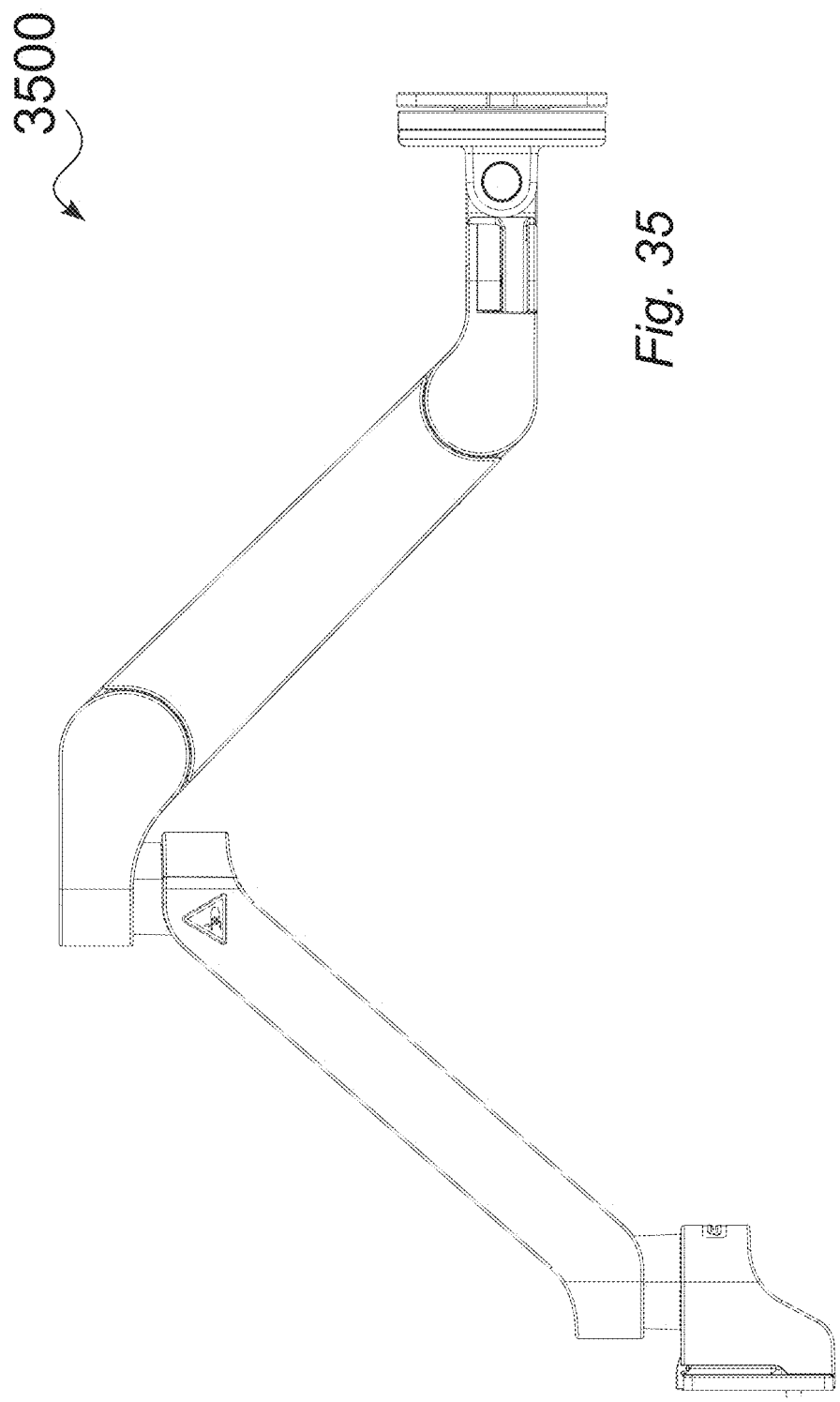
FIG. 35 is a right side view of an illustrative tablet arm, with extension, in a downward position, in accordance with various embodiments.

FIG. 35 is a right-side view of an illustrative tablet arm 3500, with extension, in a downward position, in accordance with various embodiments.

Figure 36:
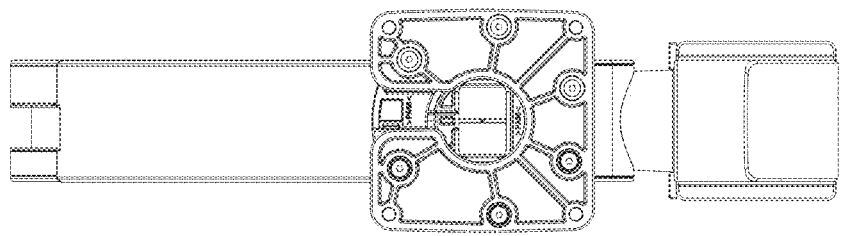
FIG. 36 is a front (tablet-side) view of an illustrative tablet arm, with extension, in a downward position, in accordance with various embodiments.

FIG. 36 is a front (tablet-side) view of an illustrative tablet arm 3600, with extension, in a downward position, in accordance with various embodiments.

Figure 37:
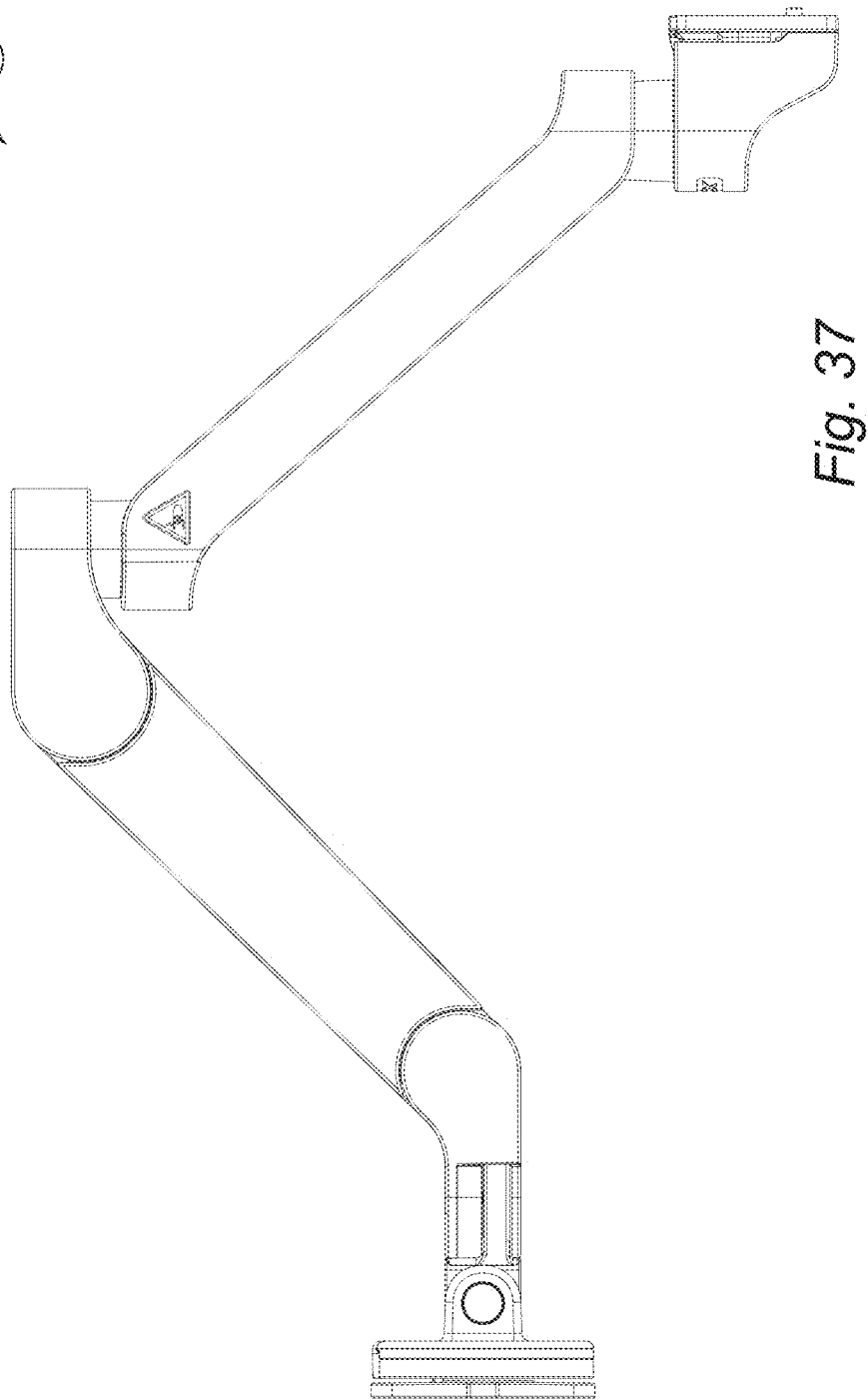
FIG. 37 is a left side view of an illustrative tablet arm, with extension, in a downward position, in accordance with various embodiments.

FIG. 37 is a left side view of an illustrative tablet arm 3700, with extension, in a downward position, in accordance with various embodiments.

Figure 38:
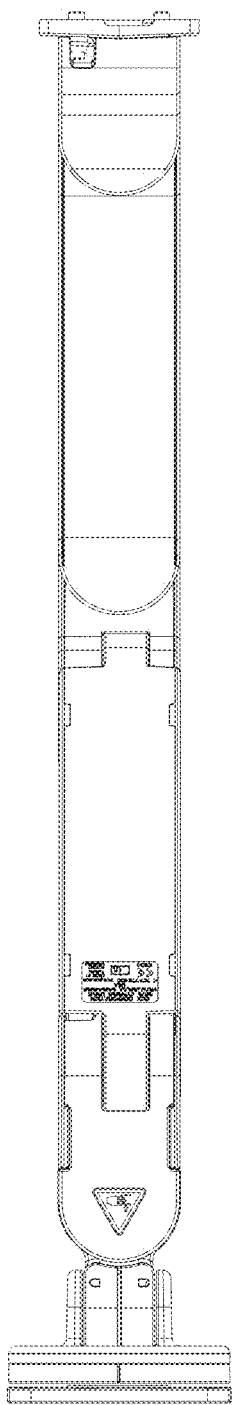
FIG. 38 is a bottom view of an illustrative tablet arm, with extension, in a downward position, in accordance with various embodiments.

FIG. 38 is a bottom view of an illustrative tablet arm 3800, with extension, in a downward position, in accordance with various embodiments.

Figure 39:
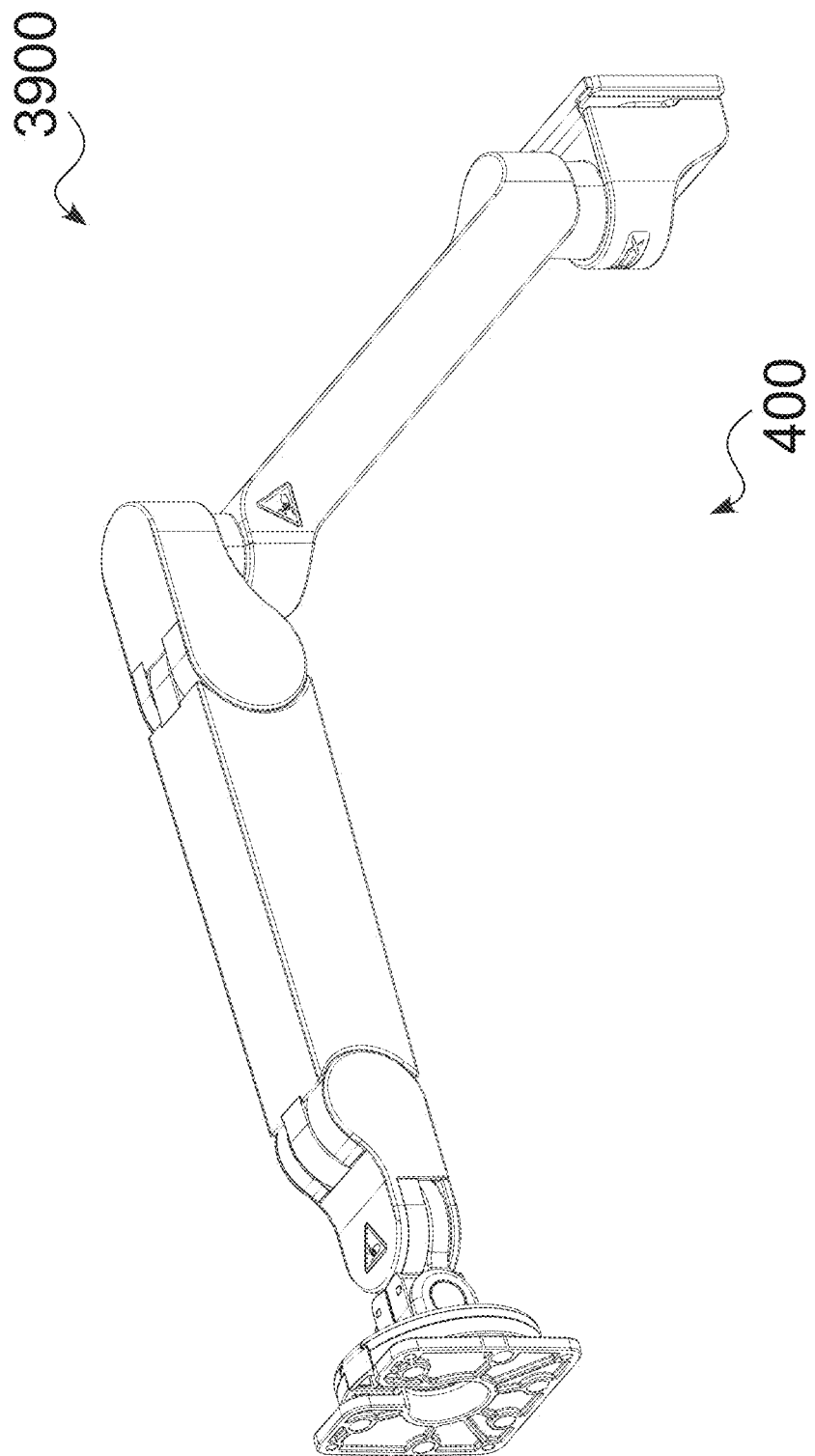
FIG. 39 is a front perspective view of an illustrative tablet arm, with extension, in a horizontal position, in accordance with various embodiments.

FIG. 39 is a front perspective view of an illustrative tablet arm 3900, with extension, in a horizontal position, in accordance with various embodiments.

Figure 40:
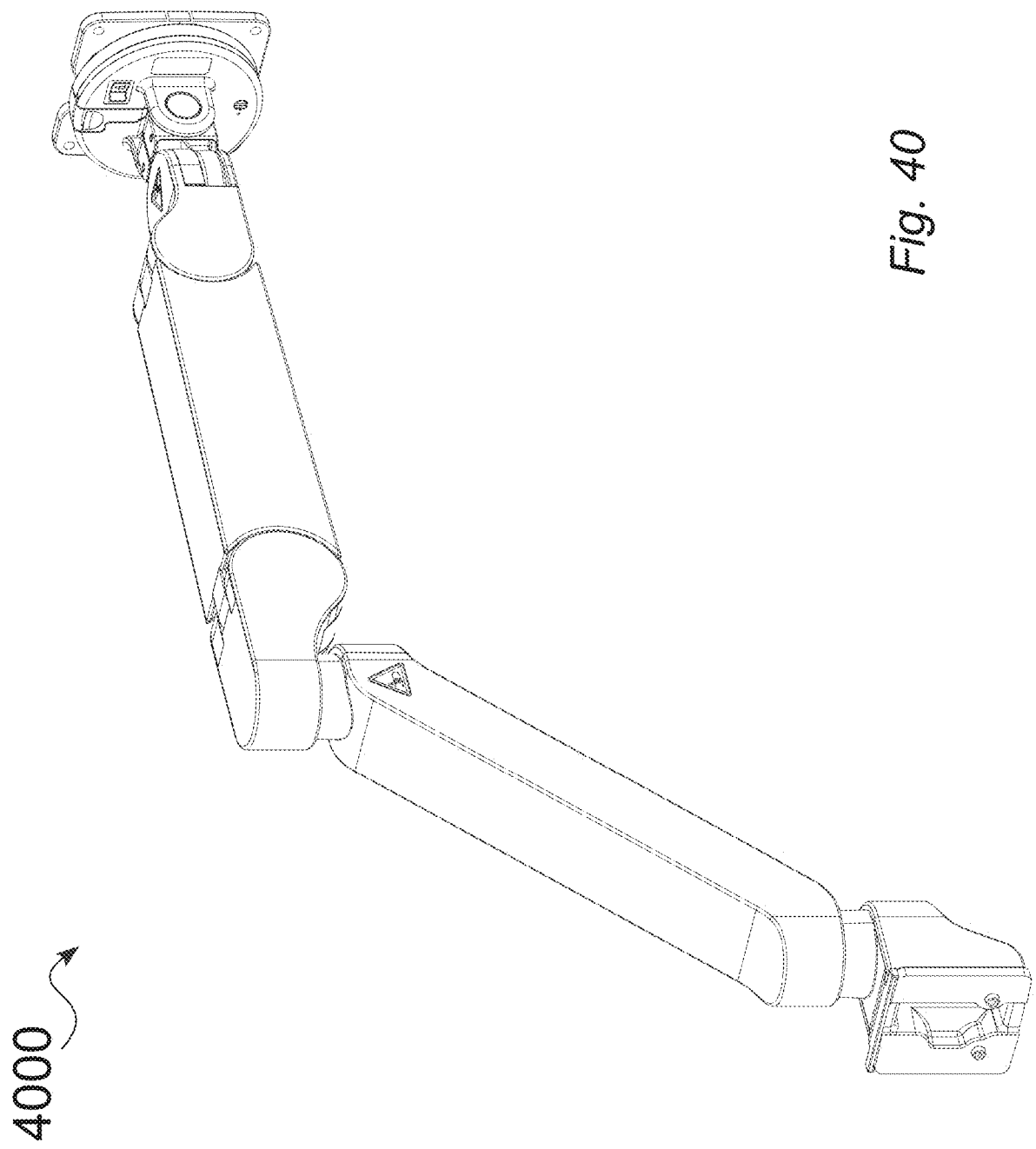
FIG. 40 is a rear perspective view of an illustrative tablet arm, with extension, in a horizontal position, in accordance with various embodiments.

FIG. 40 is a rear perspective view of an illustrative tablet arm 4000, with extension, in a horizontal position, in accordance with various embodiments.

Figure 41:
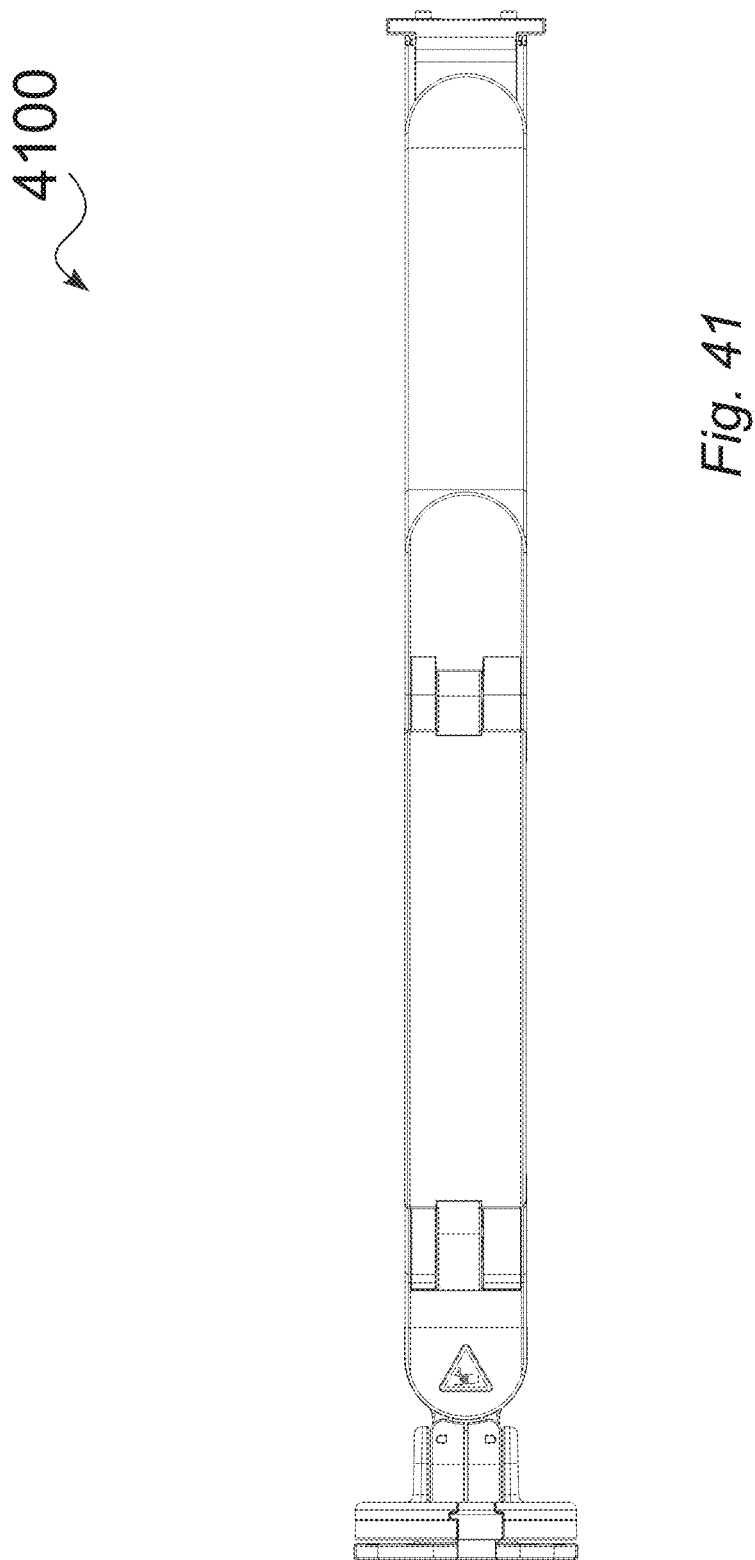
FIG. 41 is a top view of an illustrative tablet arm, with extension, in a horizontal position, in accordance with various embodiments.

FIG. 41 is a top view of an illustrative tablet arm 4100, with extension, in a horizontal position, in accordance with various embodiments.

Figure 42:
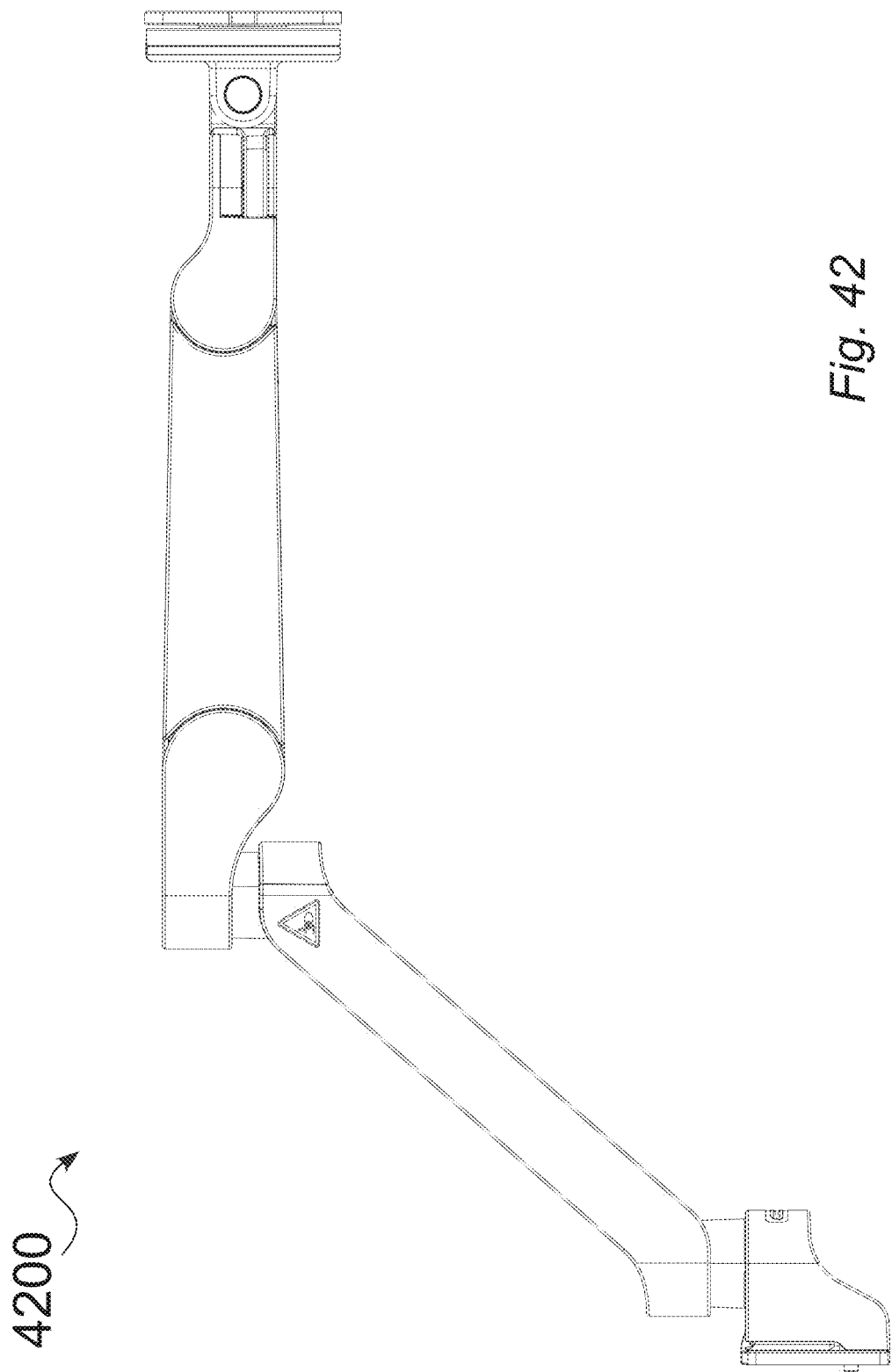
FIG. 42 is a right side view of an illustrative tablet arm, with extension, in a horizontal position, in accordance with various embodiments.

FIG. 42 is a right-side view of an illustrative tablet arm 4200, with extension, in a horizontal position, in accordance with various embodiments.

Figure 43:
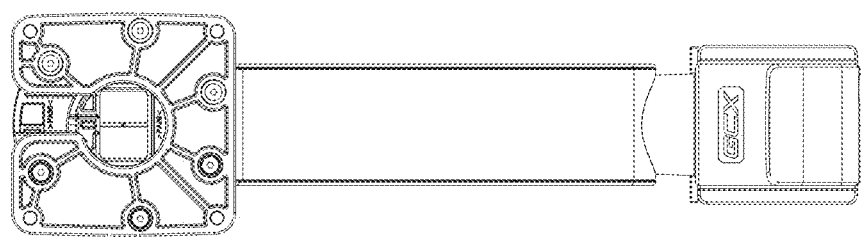
FIG. 43 is a front (tablet-side) view of an illustrative tablet arm, with extension, in a horizontal position, in accordance with various embodiments.

FIG. 43 is a front (tablet-side) view of an illustrative tablet arm 4300, with extension, in a horizontal position, in accordance with various embodiments.

Figure 44:
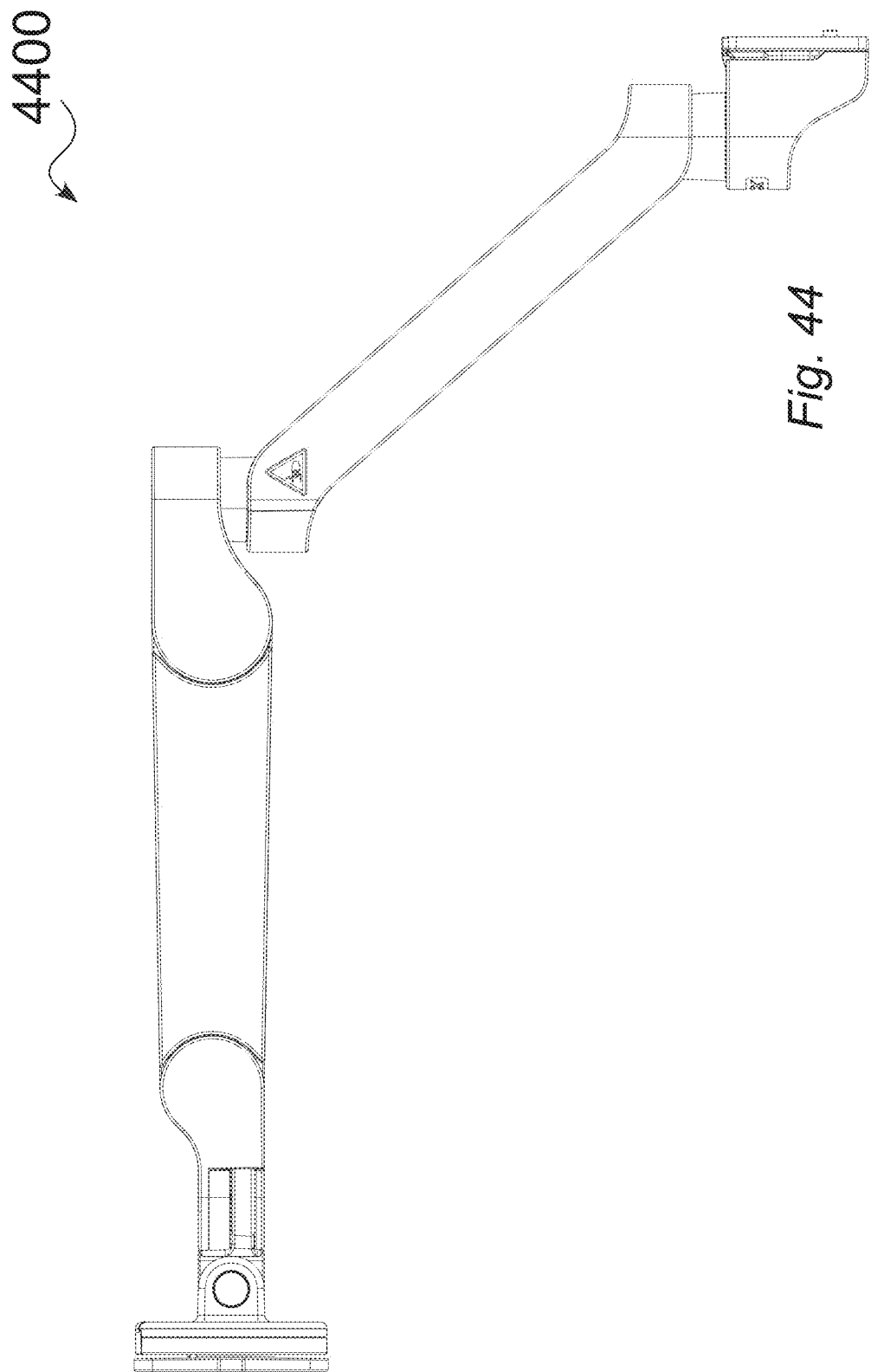
FIG. 44 is a left side view of an illustrative tablet arm, with extension, in a horizontal position, in accordance with various embodiments.

FIG. 44 is a left side view of an illustrative tablet arm 4400, with extension, in a horizontal position, in accordance with various embodiments.

Figure 45:
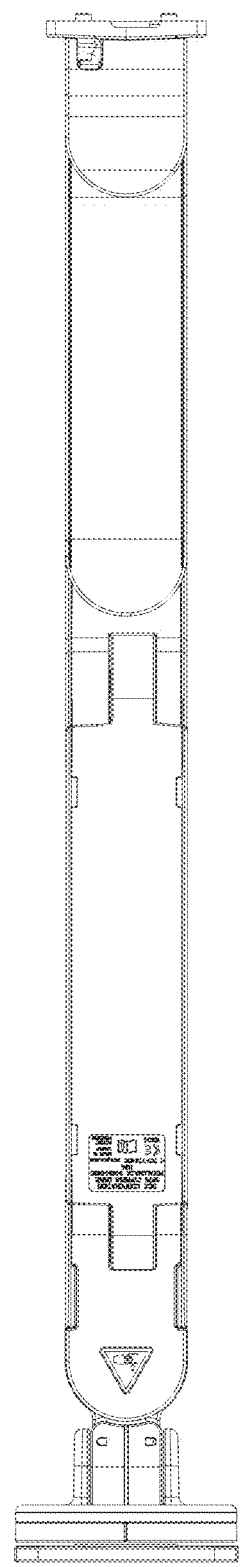
FIG. 45 is a bottom view of an illustrative tablet arm, with extension, in a horizontal position, in accordance with various embodiments.

FIG. 45 is a bottom view of an illustrative tablet arm 4500, with extension, in a horizontal position, in accordance with various embodiments.

Figure 46:
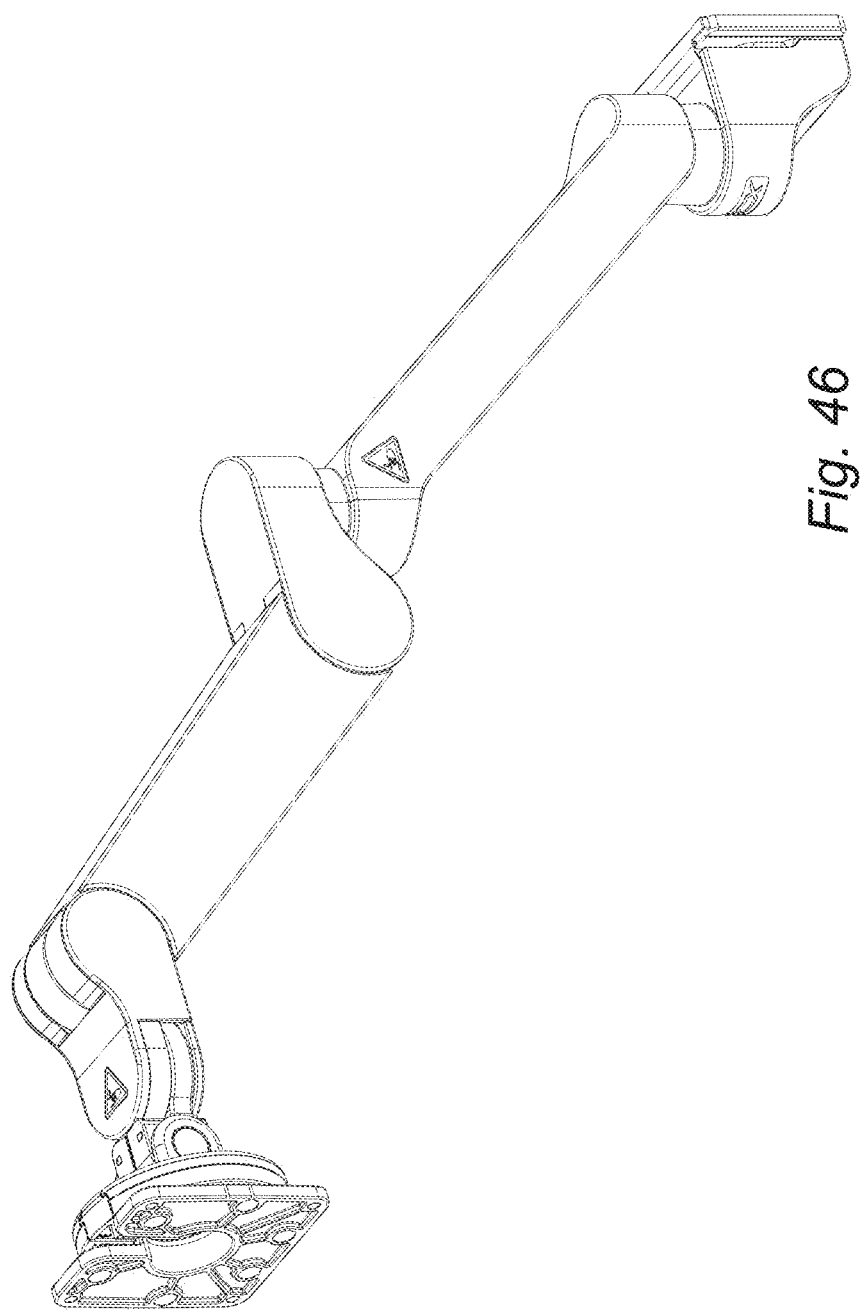
FIG. 46 is a front perspective view of an illustrative tablet arm, with extension, in an upward position.

FIG. 46 is a front perspective view of an illustrative tablet arm 4600, with extension, in an upward position.

Figure 47:
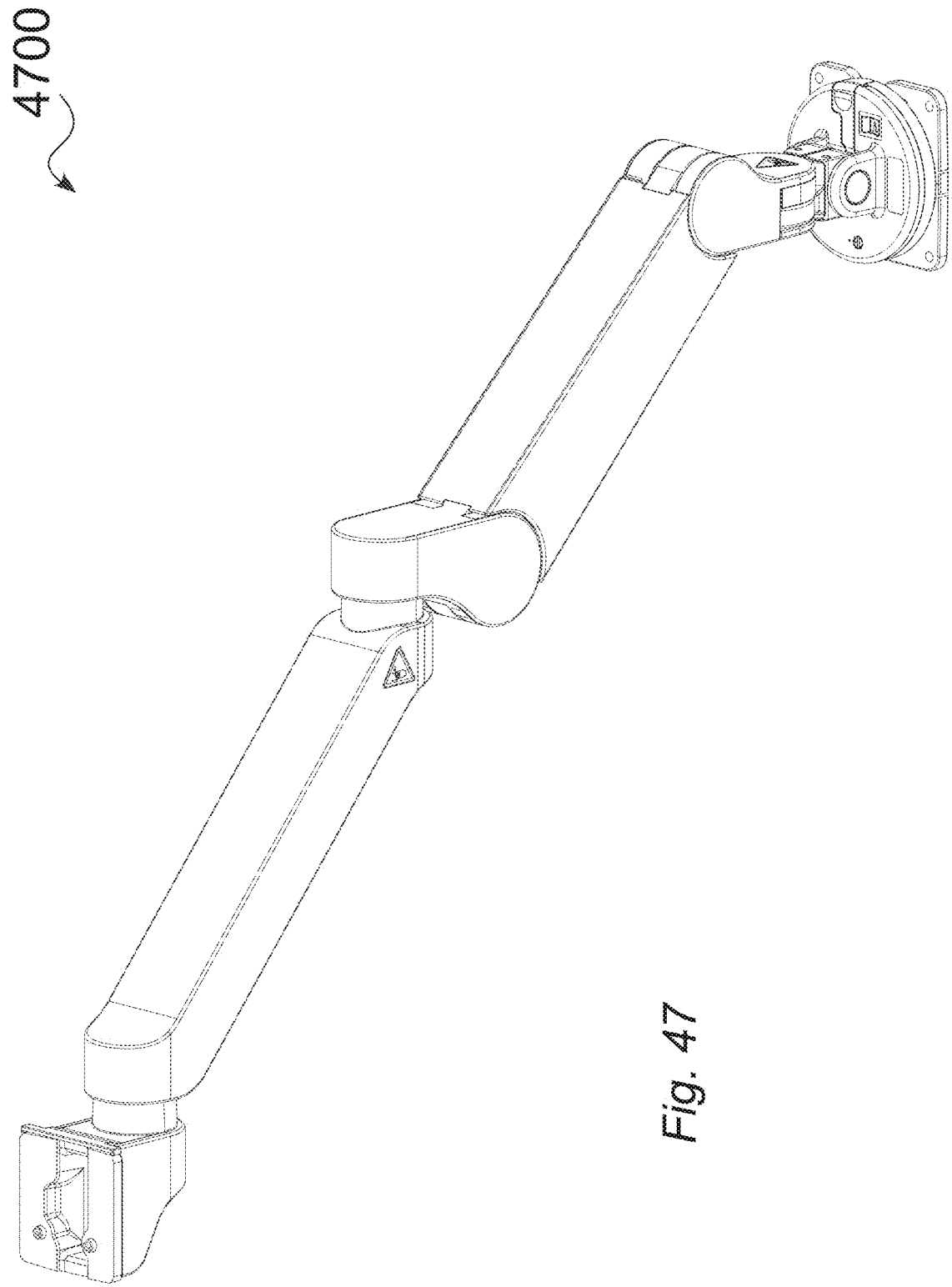
FIG. 47 is a rear perspective view of an illustrative tablet arm, with extension, in an upward position, in accordance with various embodiments.

FIG. 47 is a rear perspective view of an illustrative tablet arm 4700, with extension, in an upward position, in accordance with various embodiments.

Figure 48:
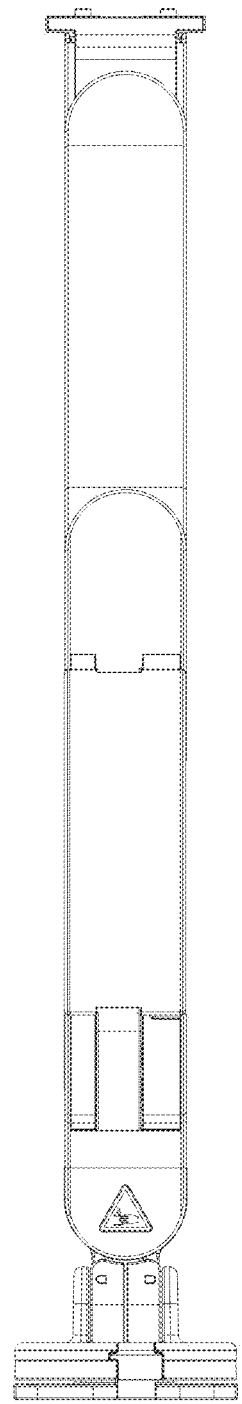
FIG. 48 is a top view of an illustrative tablet arm, with extension, in an upward position, in accordance with various embodiments.

FIG. 48 is a top view of an illustrative tablet arm 4800, with extension, in an upward position, in accordance with various embodiments.

Figure 49:
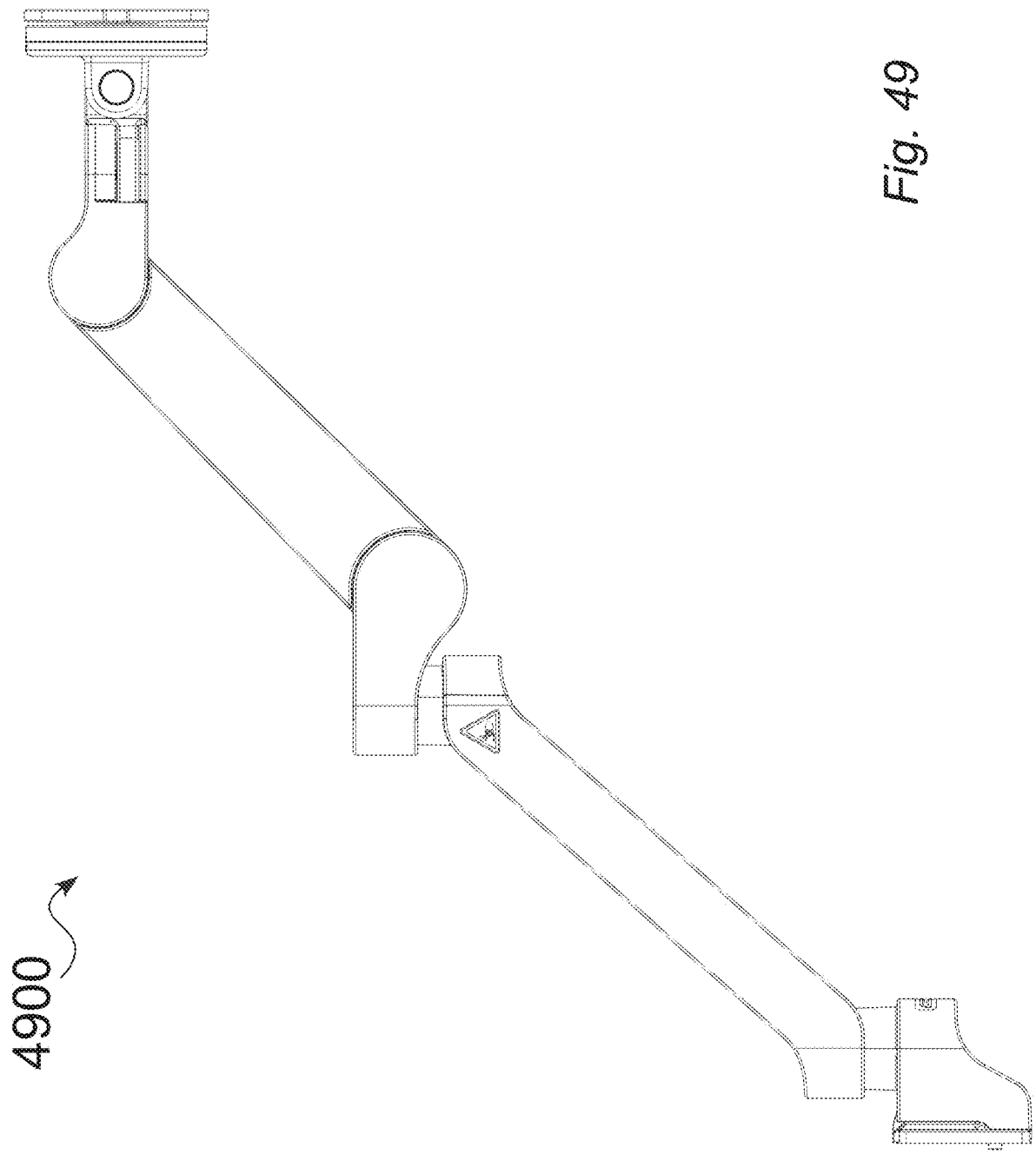
FIG. 49 is a right side view of an illustrative tablet arm, with extension, in an upward position, in accordance with various embodiments.

FIG. 49 is a right-side view of an illustrative tablet arm 4900, with extension, in an upward position, in accordance with various embodiments.

Figure 50:
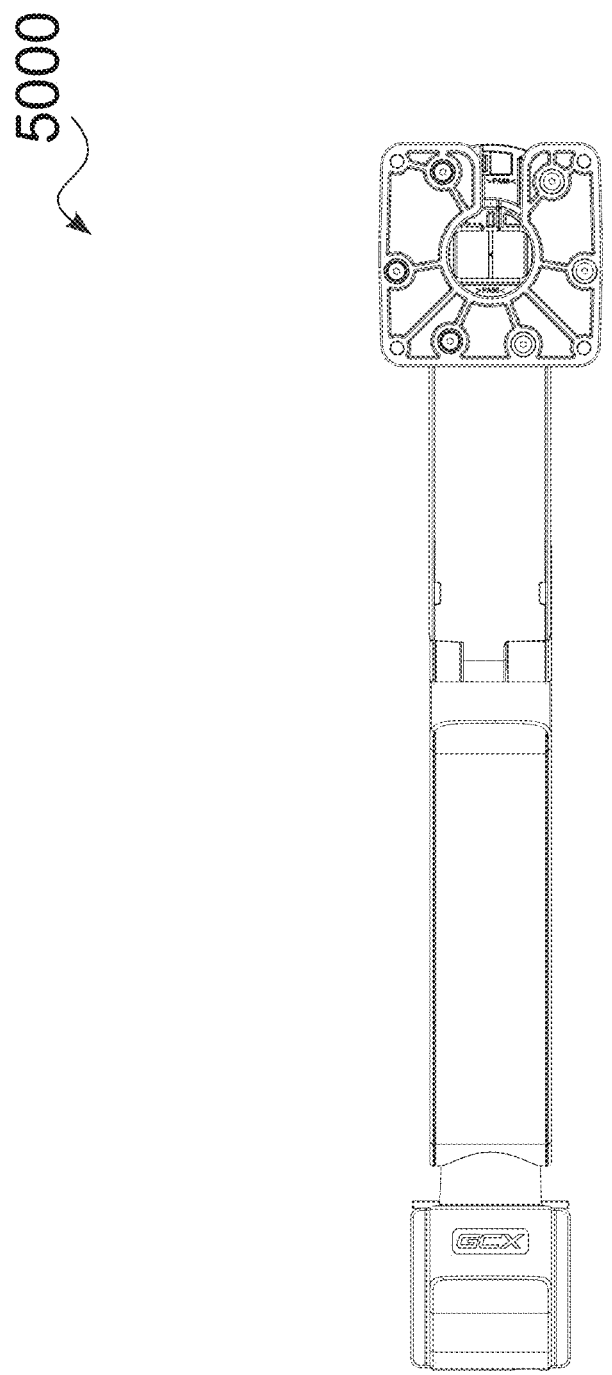
FIG. 50 is a front (tablet-side) view of an illustrative tablet arm, with extension, in an upward position, in accordance with various embodiments.

FIG. 50 is a front (tablet-side) view of an illustrative tablet arm 5000, with extension, in an upward position, in accordance with various embodiments.

Figure 51:
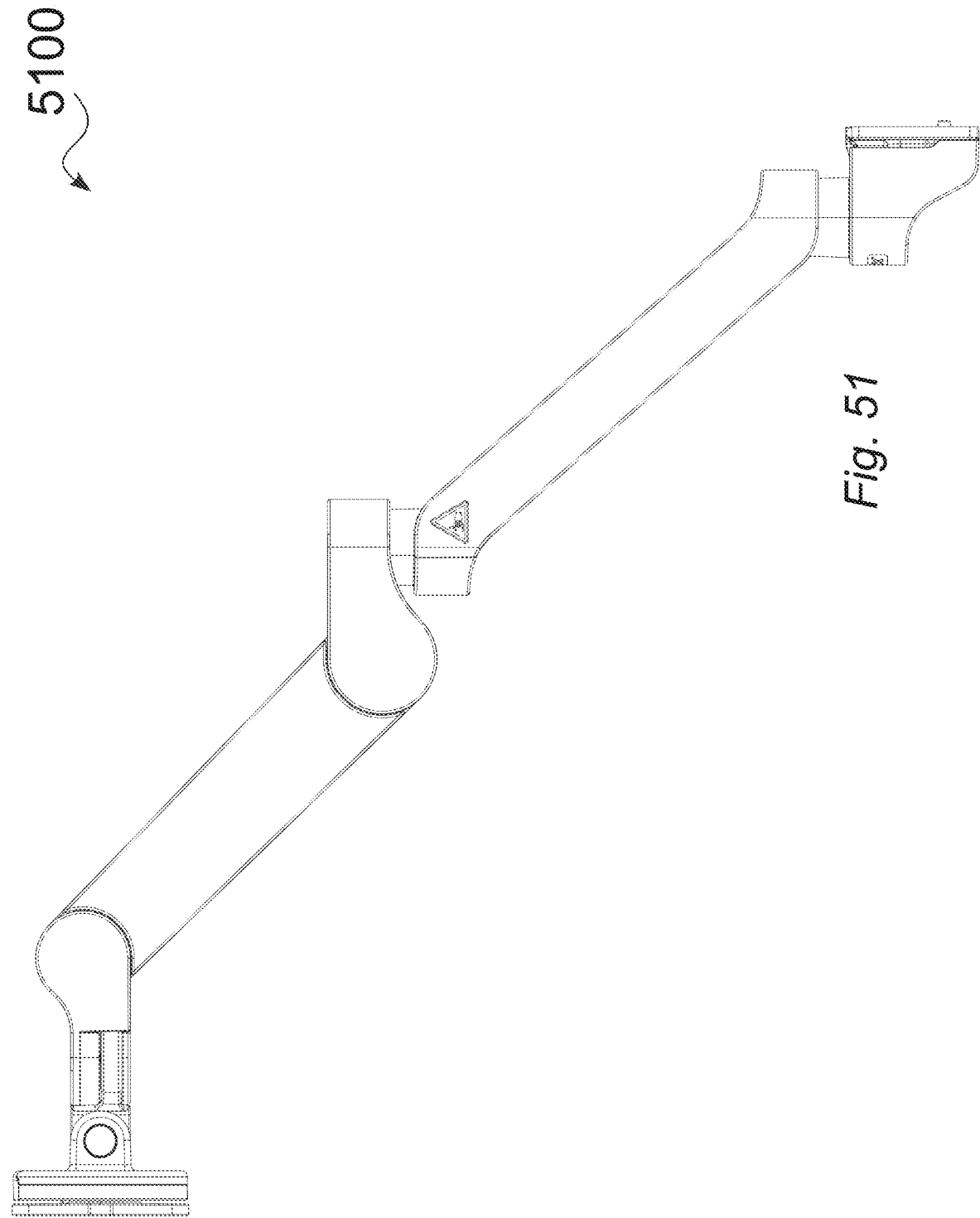
FIG. 51 is a left side view of an illustrative tablet arm, with extension, in an upward position, in accordance with various embodiments.

FIG. 51 is a left side view of an illustrative tablet arm, with extension 5100, in an upward position, in accordance with various embodiments.

Figure 52:
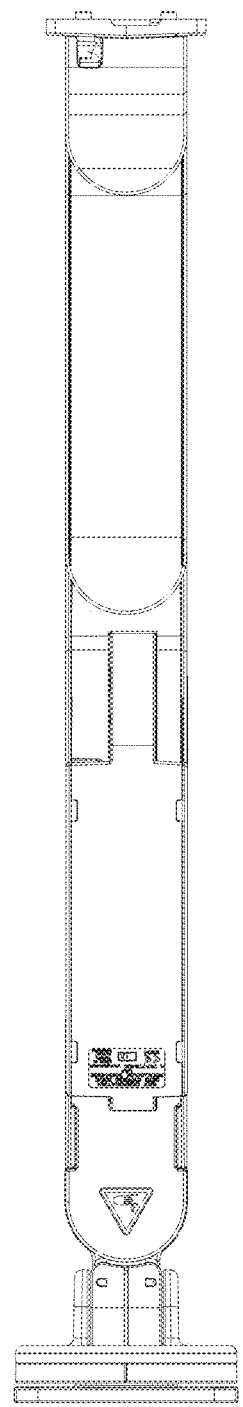
FIG. 52 is a bottom view of an illustrative tablet arm, with extension, in an upward position, in accordance with various embodiments.

FIG. 52 is a bottom view of an illustrative tablet arm 5200, with extension, in an upward position, in accordance with various embodiments.

FIG. 53 shows core support arm details related to counterbalance and friction, in accordance with various embodiments. As shown in FIG. 53, the core support arm can include any of a torque insert body/rear axle 5302, section rear hinge axis rear hinge axis 5304, torque insert end fitting 5306, torque insert body/rear axle 5308, and/or a rear gas spring pivot 5310 that can allow for free rotation and be translationally fixed to rear hinge of arm.

The core support arm can include any of a front gas spring pivot 5312 that allows for free rotation and be translationally fixed to body structure of arm, front axle 5314, rear hinge of arm 5316, body structure of arm 5318, rear link bar pivot 5320, gas spring 5322, top side of arm 5324, link bar 5326, 4-bar link parallelogram 5328, front link bar pivot 5330, and/or front knuckle of arm (device mount end of arm) 5332.

Figure 54:
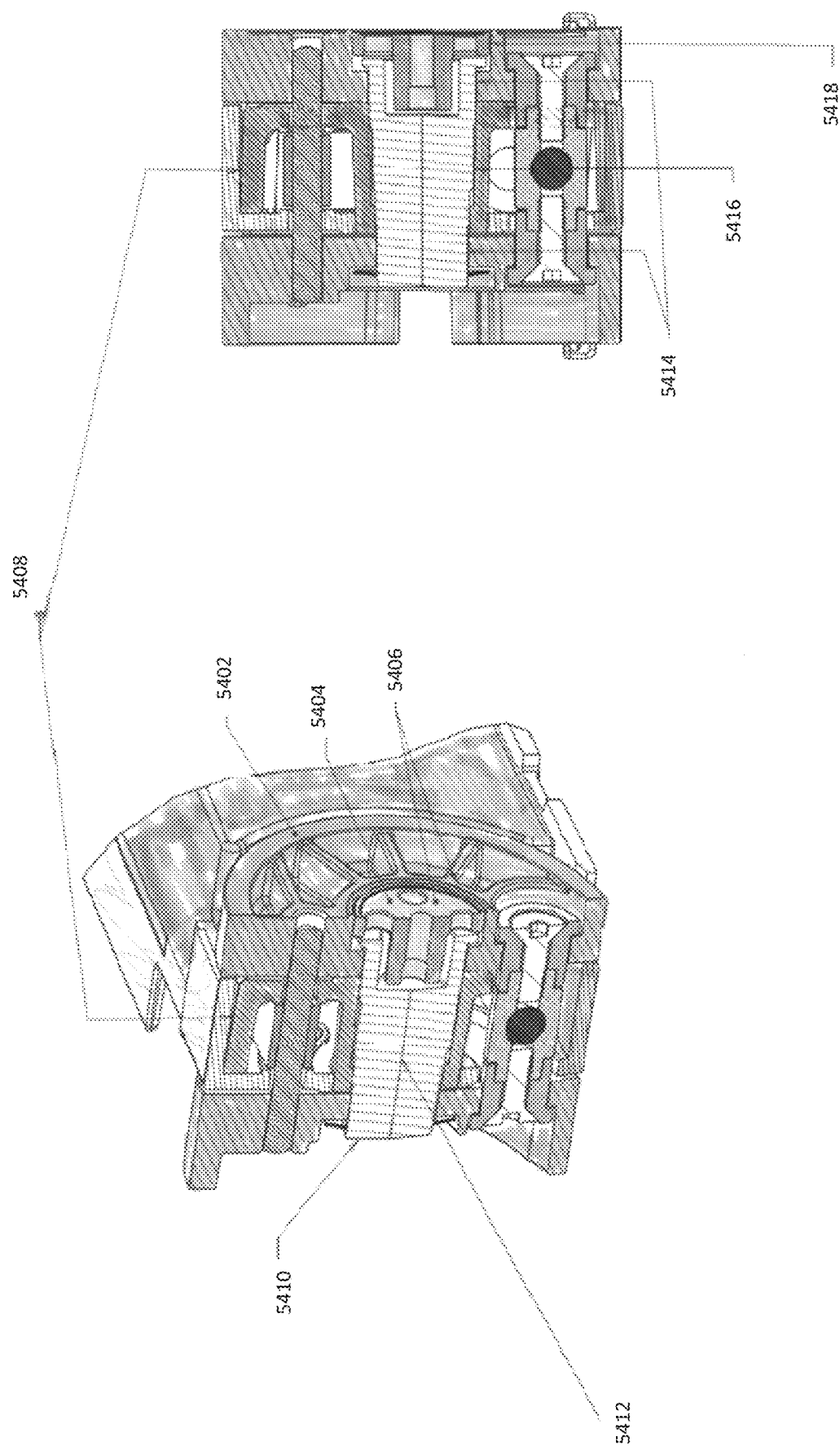
FIG. 54 show partial cutaway views of an illustrative torque insert body in relation to the rear hinge of a core support arm, in accordance with various embodiments.

FIG. 54 show partial cutaway views of an illustrative torque insert body in relation to the rear hinge of a core support arm, in accordance with various embodiments.

As shown in FIG. 54, the core support arm can include any of a rear hinge of arm 5402, torque insert end fitting 5404, fixed together in assembly 5406, body structure of arm 5408, torque insert body 5410 that also can function as a rear axle, and/or internal friction elements 5412.

The torque insert can include internal friction elements. A shaft can be engaged in the friction elements. The shaft can rotate in the housing only after a specific amount of minimum torque is applied. A differential rotation of the housing and end shaft can result in pivoting friction of a specific torque between the two. A housing and end fitting can allow for the housing to also function as an axle to the support arm. The end fitting can be held fixed as the housing is rotated and results in a specific amount of friction torque in the rear axle joint.

Torque body end sections 5414 can function as rear axle. The rear hinge of arm can pivot on the outer diameter surfaces of the torque insert body. The torque insert body middle section 5416 can be fixed to the body structure of arm. The friction insert body can be driven rotationally by levee action when the arm is moved up or down. The end fitting remains can be fixed in the rear hinge, which can be pivoting concentrically on the torque insert body. The core arm support can include a torque insert end fitting 5418 that is fixed to rear arm hinge.

As shown in FIG. 54, a torque insert body can include an end section that can function as a rear axle. The rear hinge of the arm can pivot on the outer diameter surfaces of the torque insert body. The torque insert body middle section can be fixed to the body structure of the arm. As such, the friction insert body is driven rotationally, by lever action, when the arm is moved up or down. The end fitting remains fixed in the rear hinge, which is configured to pivot concentrically on the torque insert body. The torque insert end fitting is fixed to the rear arm hinge.

In some embodiments, the torque insert can contain internal friction elements. A shaft can be engaged to the friction elements. The shaft can be configured to rotate in the housing only after a specific amount of minimum torque is applied. That is, differential rotation of the housing and end shaft can result in pivoting friction at a specific torque between the two. Some of the unique features about the implementation of the torque insert can include the design of the housing and end fitting, which can allow the housing to also function as an axle (the rear axle) of the support arm. The end fitting may be held fixed as the housing is rotated, and this can result in a specific amount of friction torque in the rear axle joint.

Figure 55:
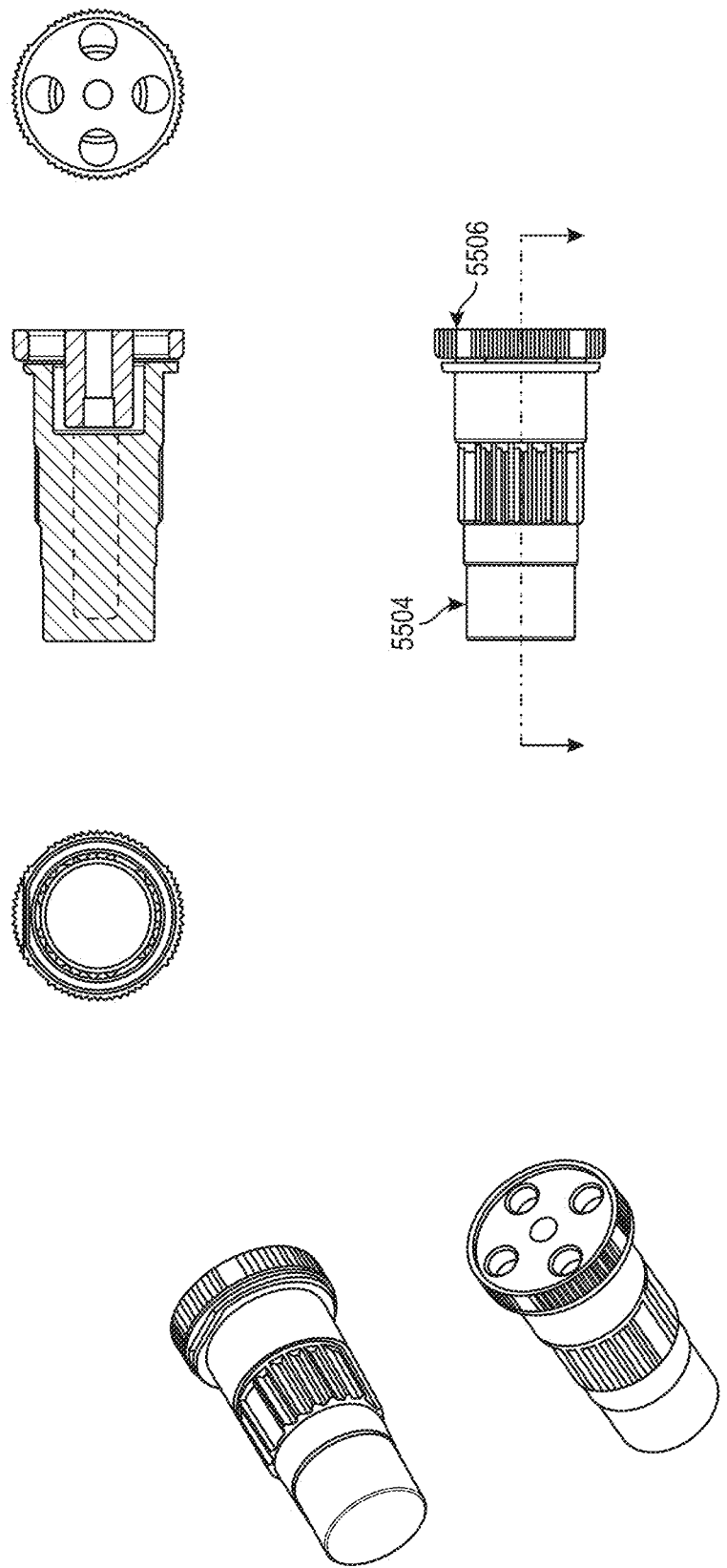
FIG. 55 provides detailed views of an illustrative torque insert for a core support arm, in accordance with various embodiments.

FIG. 55 provides detailed views of an illustrative torque insert for a core support arm, in accordance with various embodiments. As shown in FIG. 55, the core support arm can include a torque insert body 5504 and/or a torque insert end fitting 5506.

Figure 56:
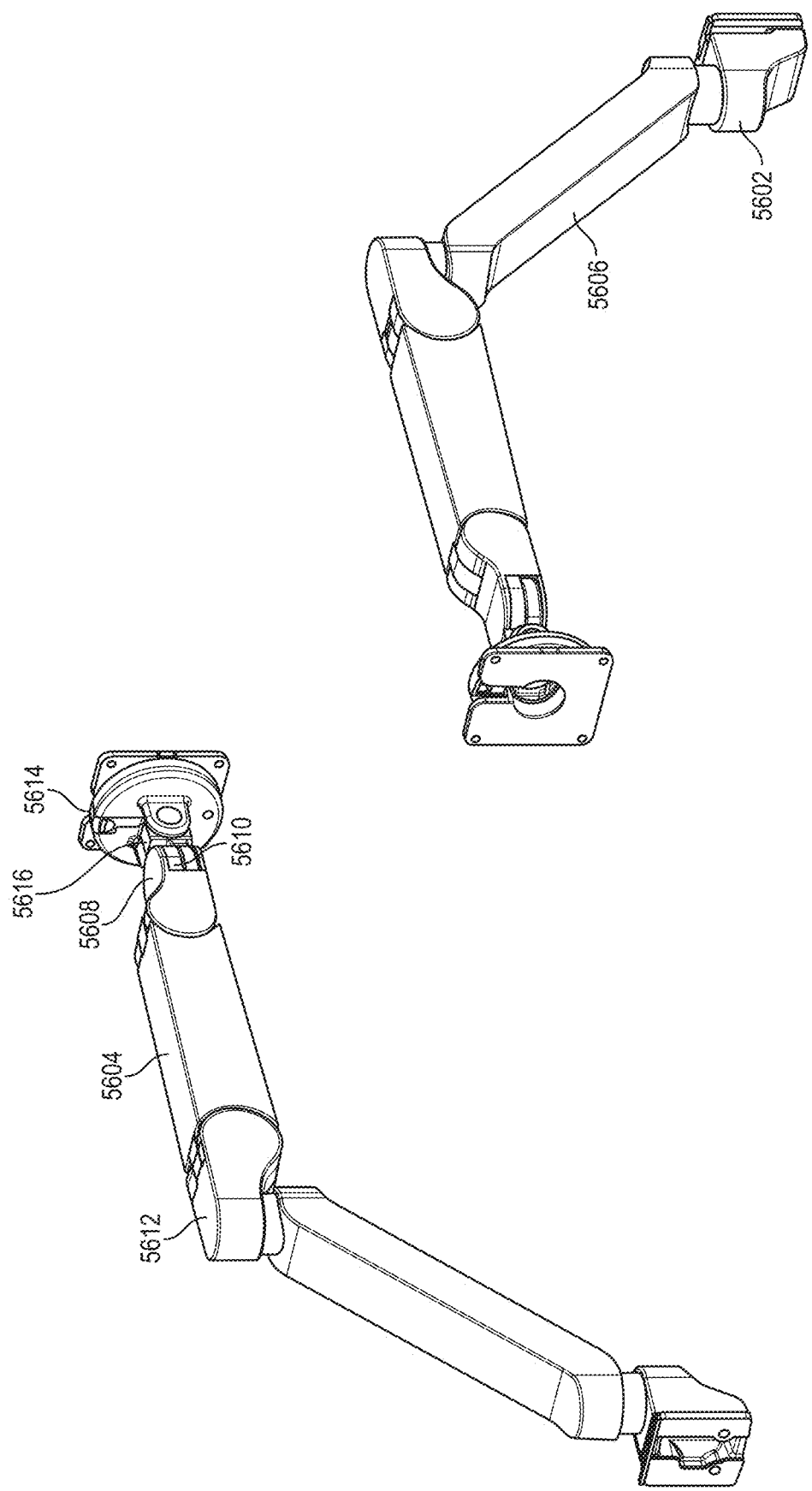
FIG. 56 shows perspective views and components related to an illustrative embodiment of a tablet arm that includes a rear extension and a channel mount, in accordance with various embodiments.

FIG. 56 shows perspective views and components related to an illustrative embodiment of a tablet arm that includes a rear extension and a channel mount, in accordance with various embodiments.

As shown in FIG. 56, the tablet arm can include any of rear mount 5602, core arm 5604, extension arm 5606, mount structure 5608, rotational mount 5610, core arm to extension arm mount 5612, rear mount support structure 5614, and/or rear mount support 5616.

Figure 57:
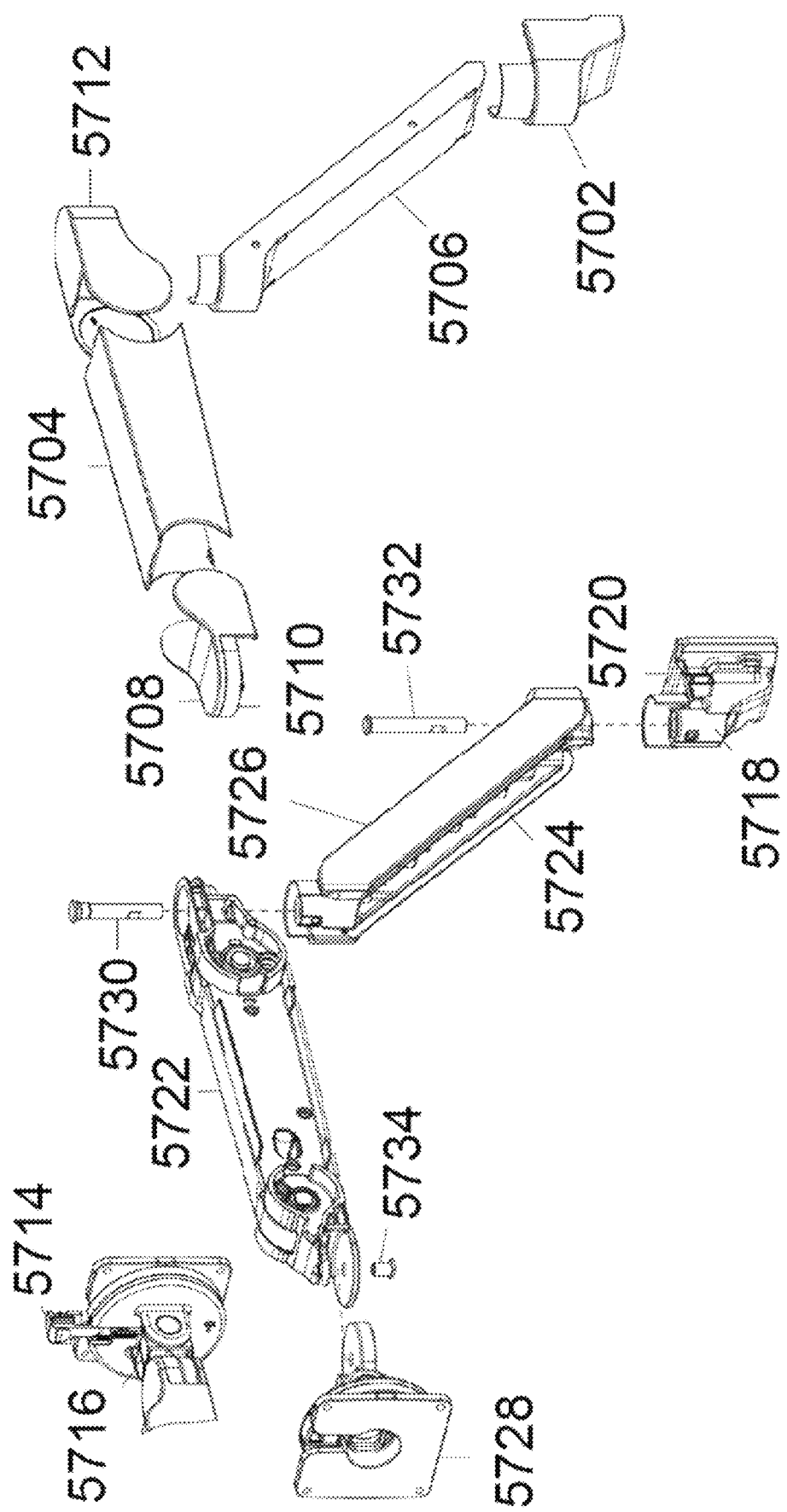
FIG. 57 shows expanded structural and out cover assembly views for an illustrative embodiment of a tablet arm that includes a rear extension and a channel mount, in accordance with various embodiments.

FIG. 57 shows expanded structural and out cover assembly views for an illustrative embodiment of a tablet arm that includes a rear extension and a channel mount, in accordance with various embodiments.

As shown in FIG. 57, the tablet arm can include multiple cable covers. For instance, the tablet arm can include any of a channel mount cable cover 5702, core arm cable cover 5704, extension cable cover 5706, front hinge cable cover 5708, front hinge seal cable cover 5710, rear hinge cable cover 5712, tilt plug cable cover 5714, tilt seals cable cover 5716. The tablet arm can include channel mount structure 5718 and/or channel mount structure cover 5720.

The tablet arm can include core arm 5722, extension structure 5724, and/or extension structure cover 5726, where the tablet arm can include a front end 5728. The tablet arm can include a core arm rear pivot post 5730, extension rear pivot post 5732, and/or a front end swivel post 5734.

Figure 58:
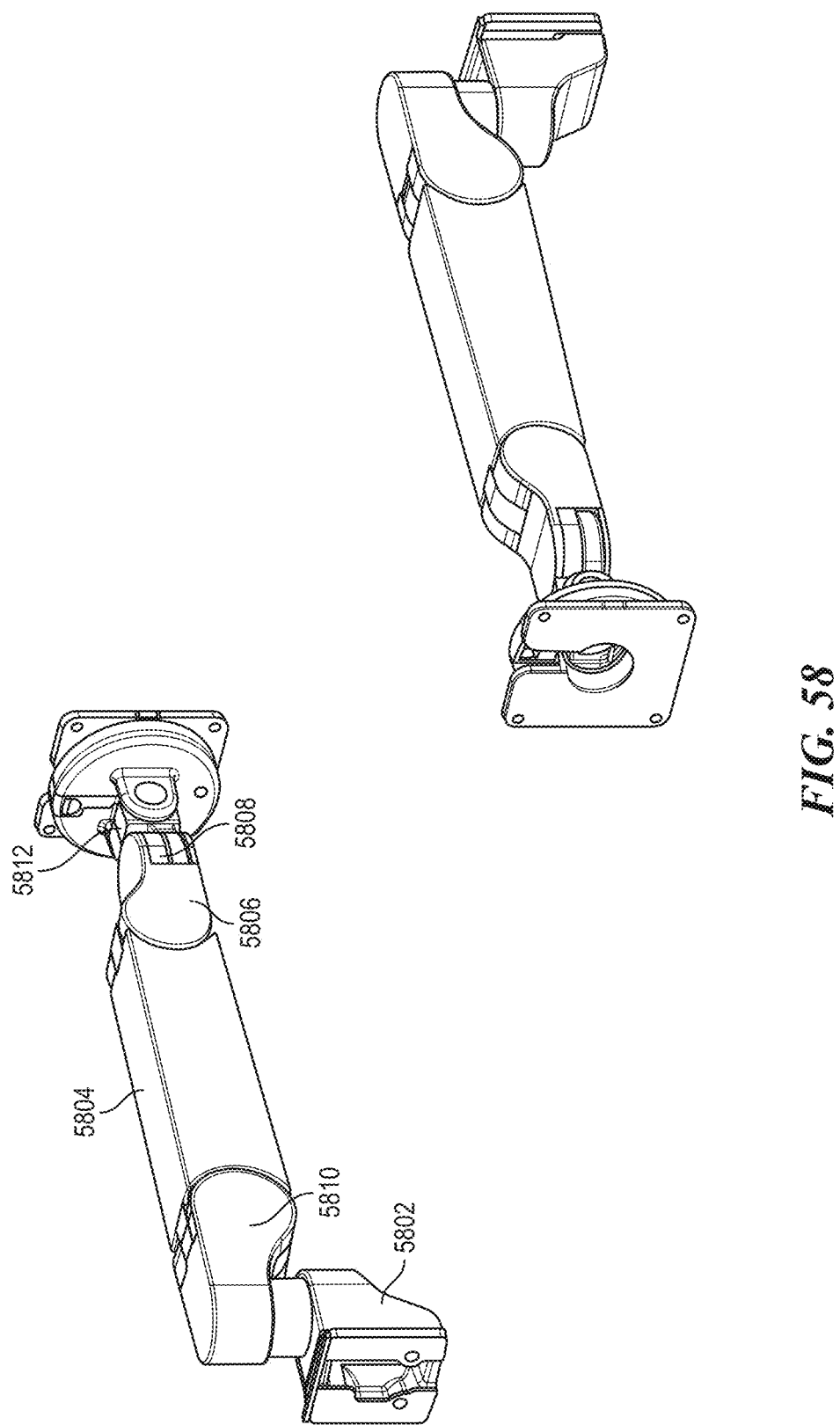
FIG. 58 shows expanded structural and out cover assembly views for an illustrative embodiment of a tablet arm, without a rear extension, having a channel mount, in accordance with various embodiments.

FIG. 58 shows expanded structural and out cover assembly views for an illustrative embodiment of a tablet arm, without a rear extension, having a channel mount, in accordance with various embodiments.

As shown in FIG. 58, the tablet arm can include any of front mount 5802, core arm 5804, rear mount 5806, rear mount rotational element 5808, front mount 5810, and/or rear mount support 5812

Figure 59:
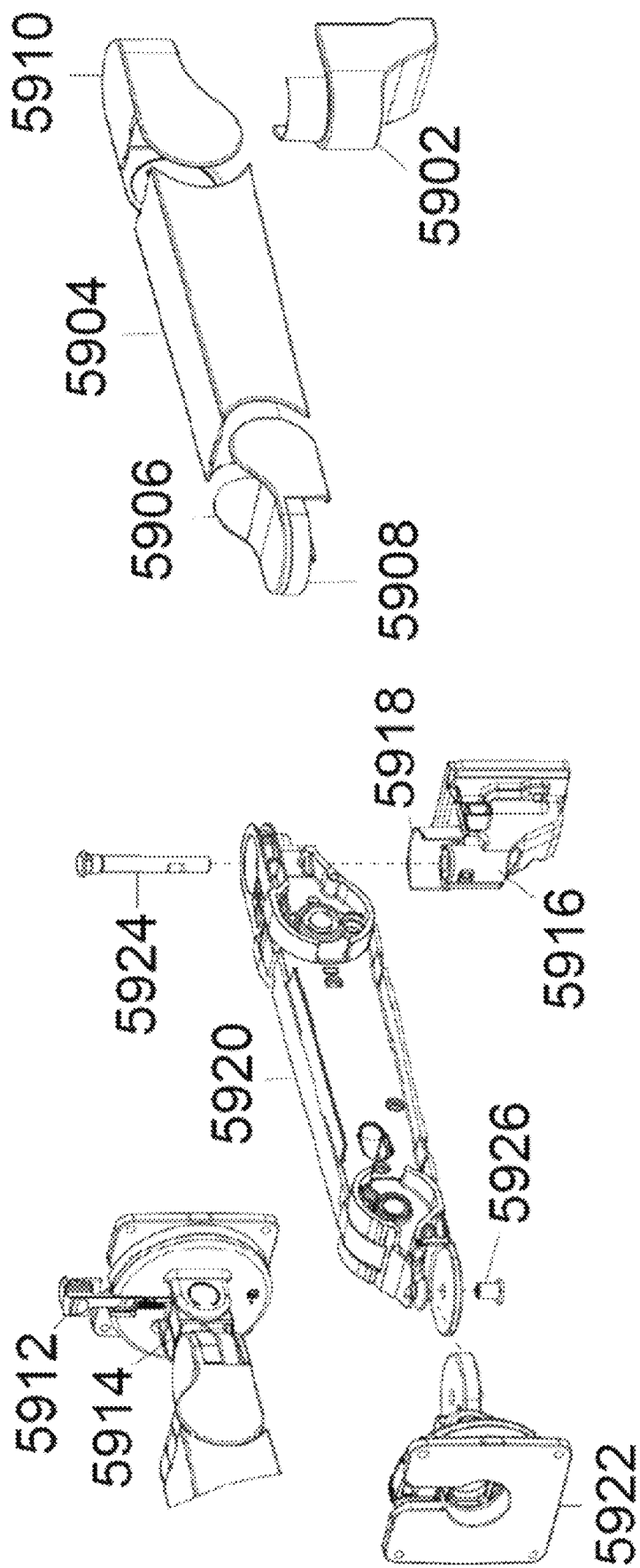
FIG. 59 shows perspective views and components related to an illustrative embodiment of a tablet arm, without a rear extension, having a channel mount, in accordance with various embodiments.

FIG. 59 shows perspective views and components related to an illustrative embodiment of a tablet arm, without a rear extension, having a channel mount, in accordance with various embodiments.

As shown in FIG. 59, the tablet arm can include any of a series of cable covers. For instance, the tablet arm can include channel mount cable cover 5902, core arm cable cover 5904, front hinge cable cover 5906, front hinge seal cable cover 5908, rear hinge cable cover 5910, tilt plug cable cover 5912, and/or tilt seals cable cover 5914.

The tablet arm can include any of a channel mount structure 5916, channel mount structure cover 5918, core arm 5920, front end 5922, rear core pivot post 5924, and/or front end swivel post 5926.

Figure 60:
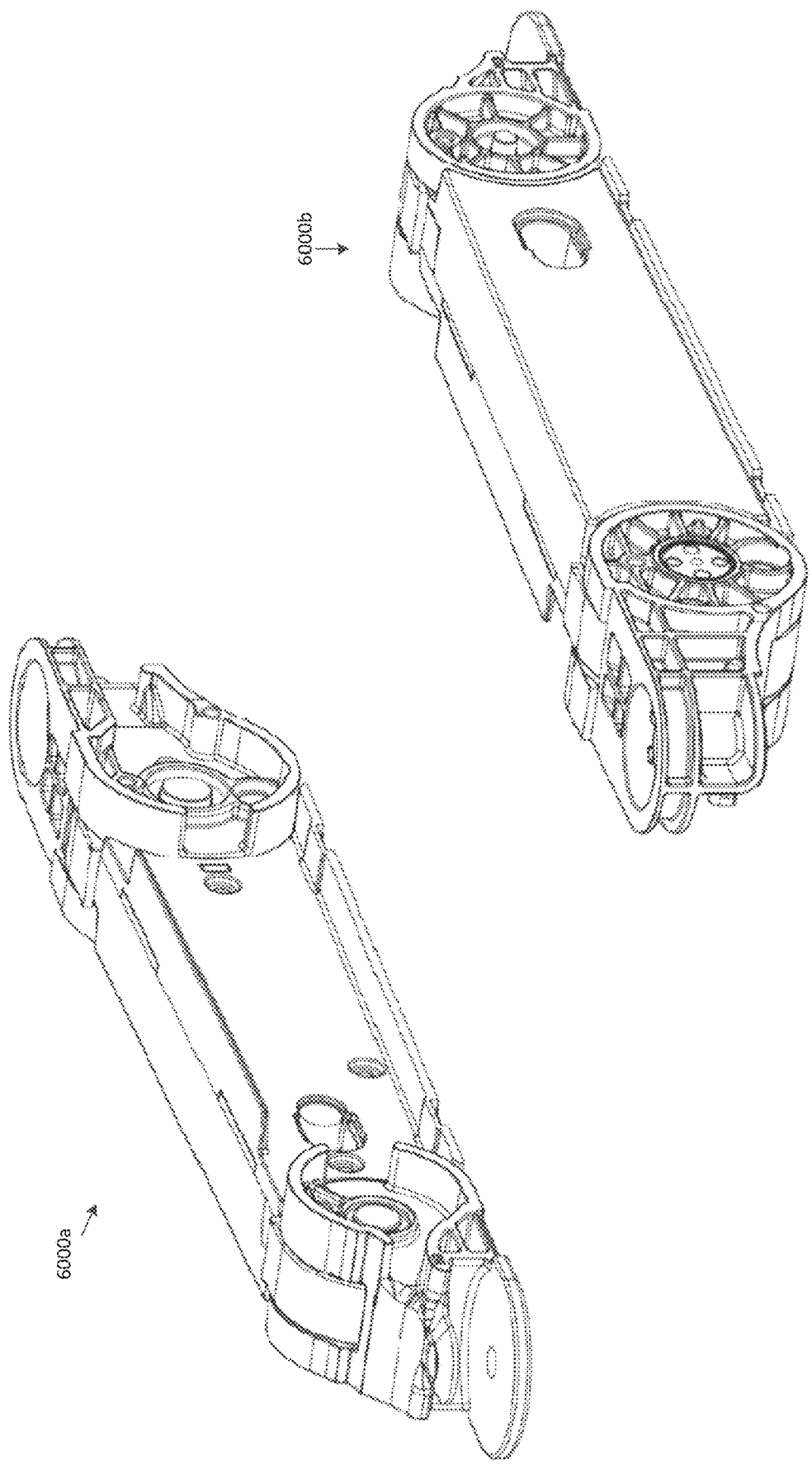
FIG. 60 shows completed assembly views of an illustrative core arm, in accordance with various embodiments.

FIG. 60 shows completed assembly views of an illustrative core arm 6000a, 6000b, in accordance with various embodiments.

Figure 61:
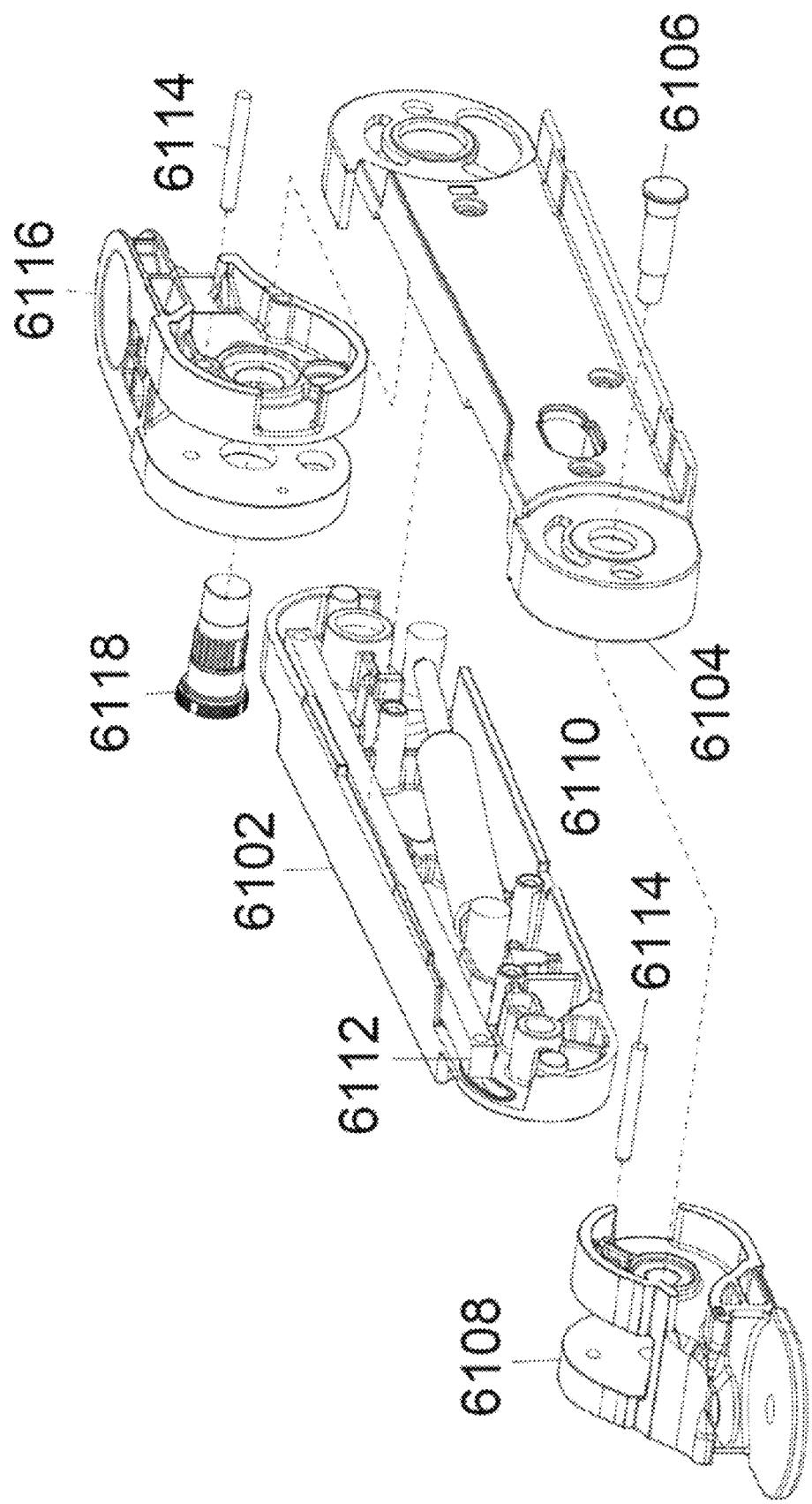
FIG. 61 is an expanded assembly view of an illustrative embodiment of a core arm, in accordance with various embodiments.

FIG. 61 is an expanded assembly view of an illustrative embodiment of a core arm, in accordance with various embodiments. As shown in FIG. 61, the core arm can include a core arm body structure 6102, the core arm body structure cover 6104, a front axle 6106, front hinge 6108, gas spring assist 6110, link bar 6112, link bar pin 6114, rear hinge 6116, and/or a torque insert 6118.

Figure 62:
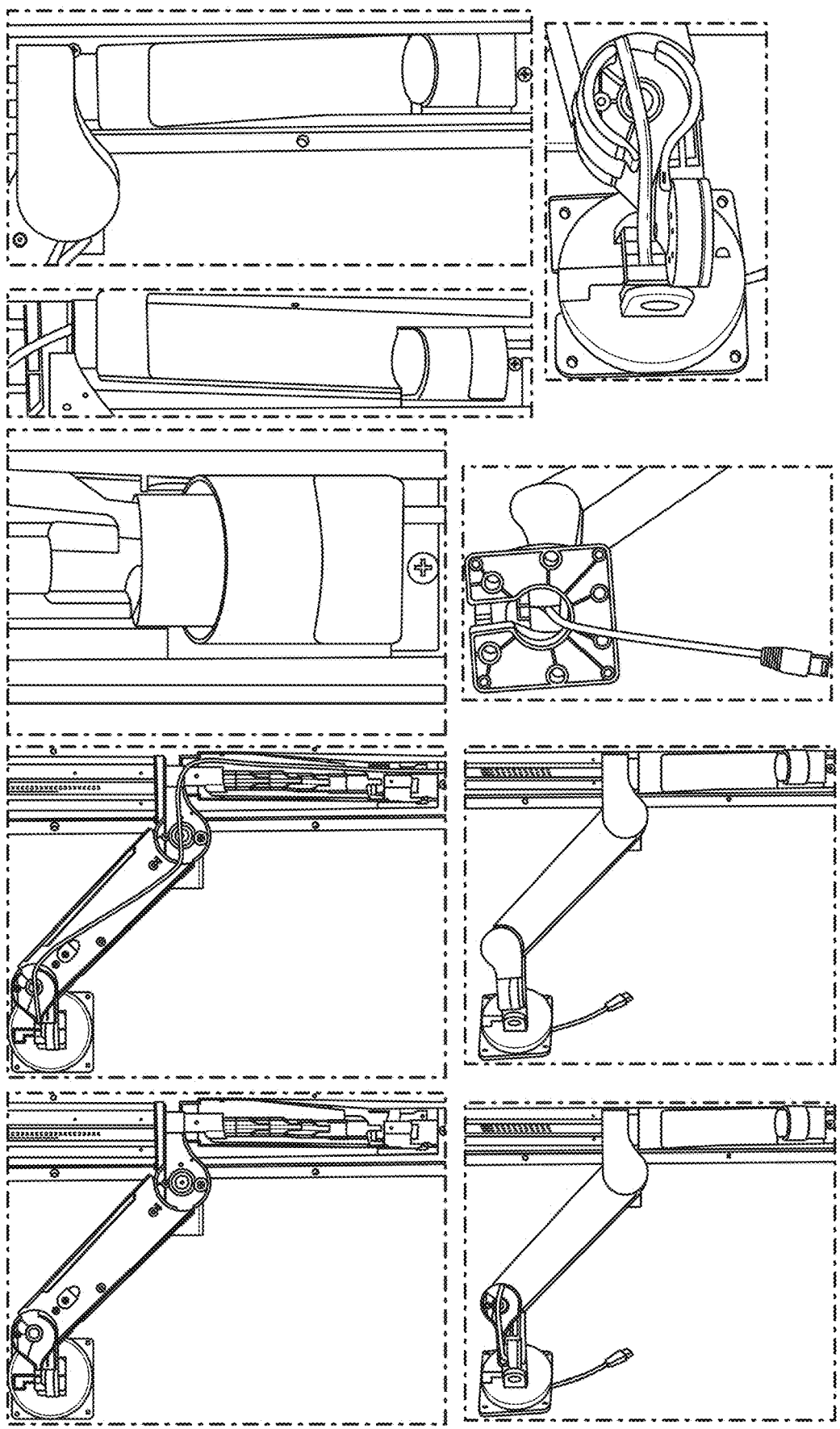
FIG. 62 shows sequential views showing cable management and concealment, including illustrative cable and outer cover installation, in accordance with various embodiments.

FIG. 62 shows sequential views showing cable management and concealment, including illustrative cable and outer cover installation, in accordance with various embodiments. One or more components can include compliant rubber or polymer seals, such as around the rotating edges of the covers, and/or in relation to the routing of one or more cables. As seen in FIG. 62, a user, such as during manufacturing or on site, can readily install a cable through a mount arm structure, for either embodiments that include an extension arm, as shown, or similarly for embodiments that do not include an extension arm. In FIG. 62, a wall-channel mounted support arm readily provides access to install or remove an interconnecting cable, when the outer covers are removed. As seen in FIG. 62, the user can position the cable between the front, i.e., tablet end of the support structure and the rear, i.e., mounting end of the support structure. The user can then readily install the outer covers as shown. In current embodiments, the outer covers can snap in place, without fasteners, and can be configured to prevent or resist contamination within the environment in which the support arm is used.

In some embodiments, the cables can generally pass through the axes of joint rotation (or as near to as possible within other design constraints). In some embodiments, there are no exposed cable service loops, which can keep them clean, out of harm's way, out of patients' (especially children's) reach allowing more effective and safe technology deployment to a broader demographic.

In some embodiments, the asymmetrical arrangement of gas spring mechanism can allow space on "side" to run the cables (this was a more challenging system engineering design); Easily attachable/detachable covers allow efficient installation and maintenance. This access and maintenance can happen in minutes. In contrast, for embodiments of structural arms that have all-internal cabling, the process of installing or replacing cable is so onerous that it is restricted to factory work or hours of field work. Embodiments having an asymmetrical arrangement disclosed herein can effectively isolate the cables from the "works" of the arm, so as to minimize their exposure to harm/damage.

Figure 63:
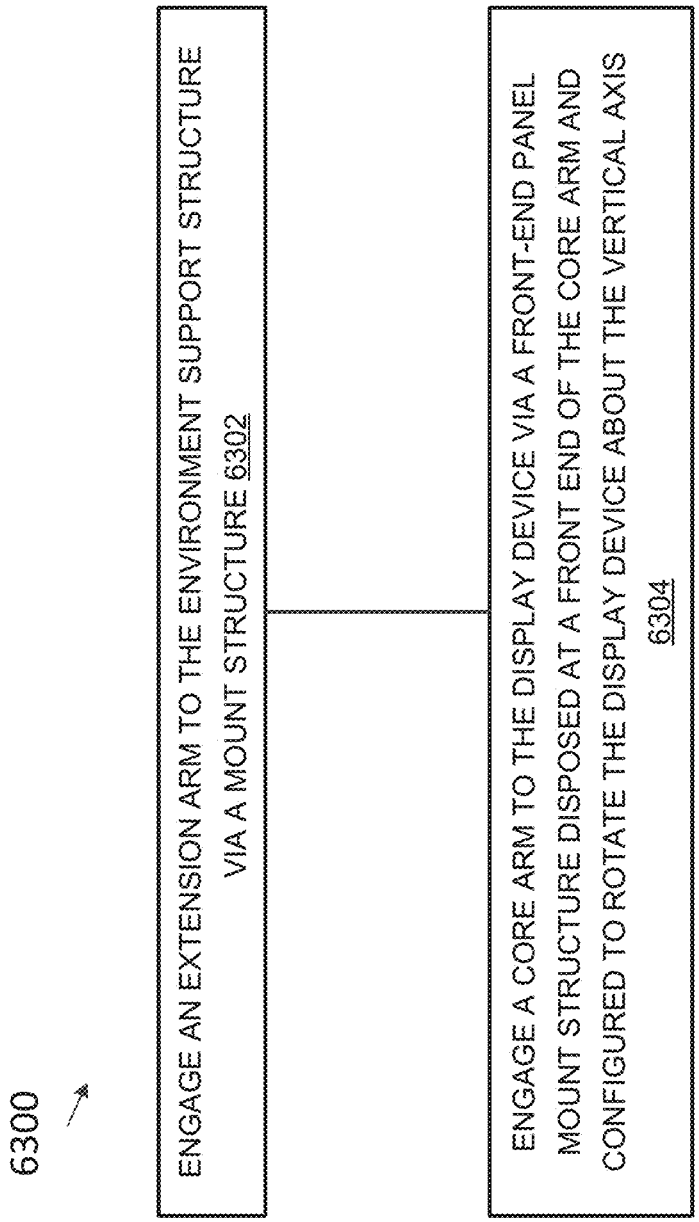
FIG. 63 is a block diagram of an example method for engaging a support arm to both a display device and an environmental support structure, in accordance with various embodiments.

FIG. 63 is a block diagram of an example method 6300 for engaging a support arm to both a display device and an environmental support structure. The method may include engaging an extension arm to the environment support structure via a mount structure (block 6302). The rear mount can be configured to rotate the extension arm about a vertical axis.

The method can also include engaging a core arm to the display device via a front-end panel mount structure disposed at a front end of the core arm and configured to rotate the display device about the vertical axis (block 6304). The core arm may be engaged to the extension arm via a mount structure. The core arm may be configured to rotate about the vertical axis via a rear axle disposed on a rear end, a front axle disposed on the front end, and a linkage assembly that includes a spring element extending from the rear end to the front end.

In some embodiments, the method can include engaging the core arm with the extension arm at the mount structure via a suitable fastener. The method can also include disposing a rear mount to the extension arm and disposing the front-end panel mount structure to the core arm.

In some embodiments, the mount structure is engaged to the first end includes a joint rotation stop structure that limits rotation of the mount structure to a defined rotation range relative to the vertical axis. The joint rotation stop structure can include a pivot stop floating key configured to facilitate rotating of the joint rotation stop structure about a pivot stop rotation range relative to the vertical axis. The joint rotation stop structure can include a pivot stop disc disposed interior of the pivot stop floating key, wherein the pivot stop disc includes a protruded surface that, when engaged with the pivot stop floating key at a position at an end of the pivot stop rotation range, prevents rotation of the pivot stop floating key. The joint rotation stop structure can include a pivot post disposed interior to the pivot stop disc and engaged to both the pivot stop floating key and the pivot stop disc. The method can include rotating any of the core arm, extendable arm, and the front end panel mount structure as described herein.

In some embodiments, the method includes disposing at least one cable through an opening formed within the core arm body and the extension arm via the mount structure. Rotation of the mount structure can be limited to the defined rotation range relative to the vertical axis so as to prevent binding of the at least cable.

CONCLUSION

Unless contrary to physical possibility, it is envisioned that (i) the methods/steps described above may be performed in any sequence and/or in any combination, and that (ii) the components of respective embodiments may be combined in any manner.

Note that any and all of the embodiments described above can be combined with each other, except to the extent that it may be stated otherwise above or to the extent that any such embodiments might be mutually exclusive in function and/or structure.

Although the present invention has been described with reference to specific exemplary embodiments, it will be recognized that the invention is not limited to the embodiments described but can be practiced with modification and alteration within the spirit and scope of the examples disclosed herein. Accordingly, the specification and drawings are to be regarded in an illustrative sense rather than a restrictive sense.

What is claimed is:

1. A support arm comprising:
   a core arm body pivotably mounted to a mount structure comprising a joint rotation stop structure configured to limit rotation of the mount structure to a defined rotation range relative to a vertical axis,
   wherein the joint rotation stop structure comprises:
   a pivot stop floating key configured to facilitate rotating of the joint rotation stop structure about a pivot stop rotation range relative to the vertical axis;

a pivot stop disc disposed interior to the pivot stop floating key,
wherein the pivot stop disc comprises a protruded surface that, when engaged with the pivot stop floating key at a position at an end of the pivot stop rotation range, prevents rotation of the pivot stop floating key; and
a pivot post disposed interior to the pivot stop disc and engaged to both the pivot stop floating key and the pivot stop disc.

2. The support arm of claim 1, wherein the core arm body extends from a first end of the core arm body to a second end opposite to the first end, and
wherein the second end is pivotably mounted to a front-end panel mount structure.

3. The support arm of claim 2, wherein the front-end panel mount structure is configured to engage with a display device, and
wherein the front-end panel mount structure is configured to rotate about the vertical axis.

4. The support arm of claim 1, comprising a spring element extending from a first end to a second end of the core arm body,
wherein the spring element provides a gas spring counterbalance force.

5. The support arm of claim 4, wherein the gas spring counterbalance force is non-adjustable, and
wherein the spring element is configured to be set for multiple counterbalance values within a payload range.

6. The support arm of claim 1, comprising a friction pack element disposed at a second end of the core arm body,
wherein the friction pack element is non-adjustable, and
wherein the friction pack element supports multiple payloads within a range of payloads.

7. The support arm of claim 1, comprising an extension arm mounted to the mount structure at a first end of the core arm body,
wherein the extension arm extends to a rear mount configured to engage to an environmental support structure.

8. The support arm of claim 1, comprising:
an extension arm disposed subjacent to the core arm body,
wherein the mount structure facilitates rotation of the core arm body about the vertical axis; and
a rear mount facilitating rotation of the extension arm about the vertical axis.

9. The support arm of claim 1, wherein the core arm body defines an opening interior to the core arm body, and
wherein the core arm body is configured to receive cabling for a display device.

10. The support arm of claim 1, comprising a front-end panel mount structure whose rotation range relative to the vertical axis prevents binding of cabling for a display device disposed in the core arm body through the front-end panel mount structure.

11. The support arm of claim 1, comprising:
a rear axle disposed at a first end of the core arm body; and
a front axle disposed at a second end of the core arm body.

12. An apparatus configured to provide support and rotational movement to a display device, the apparatus comprising:
a support arm extending from a rear end of the support arm to a front end opposite to the rear end, the support arm comprising:
a mount structure disposed at the rear end,
wherein the mount structure comprises a joint rotation stop structure configured to limit rotation of the mount structure to a defined rotation range relative to a vertical axis, and
wherein the joint rotation stop structure comprises:
a pivot stop floating key configured to facilitate rotating of the joint rotation stop structure about a pivot stop rotation range relative to the vertical axis;
a pivot stop disc disposed interior to the pivot stop floating key,
wherein the pivot stop disc comprises a protruded surface that, when engaged with the pivot stop floating key at a position at an end of the pivot stop rotation range, prevents rotation of the pivot stop floating key; and
a pivot post disposed interior to the pivot stop disc and engaged to both the pivot stop floating key and the pivot stop disc.

13. The apparatus of claim 12, comprising a front-end panel mount structure disposed at the front end,
wherein the front-end panel mount structure is configured to:
engage with the display device; and
rotate about the vertical axis.

14. The apparatus of claim 13, wherein the support arm defines an opening interior to the support arm,
wherein the support arm is configured to receive cabling for the display device, and
wherein the cabling is exposed at the front-end panel mount structure.

15. The apparatus of claim 12, comprising an extension arm engaged to the support arm at the mount structure,
wherein the extension arm comprises a rear mount configured to engage to an environmental support structure and rotate the extension arm about the vertical axis.

16. The apparatus of claim 12, comprising a spring element configured to provide a gas spring counterbalance force that is non-adjustable,
wherein the spring element is configured to be set for multiple counterbalance values that are within a payload range.

17. The apparatus of claim 12, comprising a friction pack element disposed within the front end of the support arm,
wherein the friction pack element provides upward resistance and downward resistance.

18. A method for engaging a support arm to a display device and an environmental support structure, the method comprising:
engaging an extension arm to the environmental support structure via a mount structure,
wherein the extension arm is configured to rotate about a vertical axis using a rear mount;
engaging a core arm to the display device via a front-end panel mount structure disposed at a front end of the core arm,
wherein the front-end panel mount structure is configured to rotate the display device about the vertical axis,
wherein the mount structure comprises a joint rotation stop structure that limits rotation of the mount structure to a defined rotation range relative to the vertical axis, and
wherein the joint rotation stop structure comprises:
a pivot stop floating key configured to facilitate rotating of the joint rotation stop structure about a pivot stop rotation range relative to the vertical axis, a pivot stop disc disposed interior of the pivot stop floating key, wherein the pivot stop disc comprises a protruded surface that, when engaged with the pivot stop floating key at a position at an end of the pivot stop rotation range, prevents rotation of the pivot stop floating key, and a pivot post disposed interior to the pivot stop disc and engaged to both the pivot stop floating key and the pivot stop disc.

19. The method of claim 18, comprising disposing at least one cable through an opening defined by the core arm and the extension arm via the mount structure, wherein rotation of the mount structure is limited to the defined rotation range relative to the vertical axis to prevent binding of the at least one cable.

20. The method of claim 18, wherein the core arm is configured to rotate about the vertical axis via a rear axle disposed on a rear end of the core arm, a front axle disposed on the front end, and a linkage assembly that comprises a spring element extending from the rear end to the front end.

* * * * *